(12) United States Patent
Steward et al.

(10) Patent No.: US 7,709,608 B2
(45) Date of Patent: *May 4, 2010

(54) SUBSTRATES USEFUL FOR FRET PROTEASE ASSAYS FOR BOTULINUM SEROTYPE A/E TOXINS

(75) Inventors: Lance E. Steward, Irvine, CA (US); Ester Fernandez-Salas, Fullerton, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 379 days.

This patent is subject to a terminal disclaimer.

(21) Appl. No.: 11/609,226

(22) Filed: Dec. 11, 2006

(65) Prior Publication Data

US 2010/0069610 A1 Mar. 18, 2010

Related U.S. Application Data

(62) Division of application No. 09/942,024, filed on Aug. 28, 2001, now Pat. No. 7,208,285.

(51) Int. Cl.
*C07K 1/00* (2006.01)
*C07K 2/00* (2006.01)

(52) U.S. Cl. .................. 530/350; 435/23; 435/69.1; 435/400

(58) Field of Classification Search .................. None
See application file for complete search history.

(56) References Cited

U.S. PATENT DOCUMENTS

| 5,962,637 | A | 10/1999 | Shone et al. |
| 5,965,699 | A | 10/1999 | Schmidt et al. |
| 5,981,200 | A | 11/1999 | Tsien et al. |
| 5,989,545 | A | 11/1999 | Foster et al. |
| 6,043,042 | A | 3/2000 | Shone et al. |
| 6,762,280 | B2 | 7/2004 | Schmidt et al. |
| 7,183,066 | B2 | 2/2007 | Fernandez-Salas et al. |
| 7,208,285 | B2 | 4/2007 | Steward et al. |
| 7,332,567 | B2 | 2/2008 | Steward et al. |
| 7,374,896 | B2 | 5/2008 | Steward et al. |
| 7,399,607 | B2 | 7/2008 | Williams et al. |
| 7,495,069 | B2 | 2/2009 | Steward et al. |
| 2003/0077685 | A1 | 4/2003 | Schmidt et al. |
| 2003/0104975 | A1 | 6/2003 | Auwerz et al. |
| 2007/0122858 | A1 | 5/2007 | Fernandez-Salas et al. |
| 2007/0275477 | A1 | 11/2007 | Gilmore et al. |
| 2008/0003240 | A1 | 1/2008 | Fernandez-Salas |
| 2008/0166739 | A1 | 7/2008 | Steward et al. |
| 2008/0171348 | A1 | 7/2008 | Steward et al. |
| 2008/0176249 | A1 | 7/2008 | Steward et al. |
| 2008/0182799 | A1 | 7/2008 | Fernandez-Salas et al. |
| 2008/0213796 | A1 | 9/2008 | Steward et al. |
| 2008/0220456 | A1 | 9/2008 | Williams et al. |
| 2008/0293084 | A1 | 11/2008 | Williams et al. |
| 2008/0293085 | A1 | 11/2008 | Williams et al. |
| 2008/0305509 | A1 | 12/2008 | Williams et al. |
| 2008/0305510 | A1 | 12/2008 | Williams et al. |
| 2009/0042231 | A1 | 2/2009 | Steward et al. |
| 2009/0053746 | A1 | 2/2009 | Steward et al. |

FOREIGN PATENT DOCUMENTS

| WO | WO 95/33850 | 12/1995 |
| WO | WO 02/25284 | 3/2002 |

OTHER PUBLICATIONS

Mitra et al, Gene 173:13-17, 1996.*
Office Action Date Mailed Jun. 20, 2008 in U.S. Appl. No. 10/598,073.
Keller, James E. et al, FEBS Letters, vol. 456, 1999, pp. 137-142, Persistence of botulinum neurotoxin action in cultured spinal cord cells.
Vadakkanchery V. et al, "Proteolysis of SNAP-25 isoforms by botulinum neurotoxin types A, C, and E: Domains and amino acid residues controlling the formation of enzyme-substrate complexes and cleavage", J. Neurochem, vol. 72, 1999, pp. 327-337.
Siegel R. et al, "Measurement of molecular interactions in living cells by fluorescence resonance energy transfer between variants of green fluorescent protein", STKE, Jun. 27, 2000, pp. 1-6.
Anne et al., "High-Throughput Fluorogenic Assay for Determination of Botulinum Type B Neurotoxin Protease Activity," *Analytical Biochemistry* 291:253-261 (2001).
Clegg, "Fluorescence Resonance Energy Transfer," *Current Opinion in Biotechnology* 6:103-110 (1995).
Cornille et al., "Solid-Phase Synthesis, Conformational Analysis and In Vitro Cleavage of Synthetic Human Synaptobrevin II 1-93 by Tetanus Toxin L Chain," *Eur. J. Biochem.* 222:173-181 (1994).
Ekong et al., "Recombinant SNAP-25 is an Effective Substrate for *Clostridium botulinum* Type A Toxin Endopeptidase Activity in vitro," *Microbiology* 143:3337-3347 (1997).
Florentin et al., "A Highly Sensitive Fluorometric Assay for 'Enkephalinase,' a Neutral Metalloendopeptidase That Releases Tyrosine-Glycine-Glycine from Enkephalins," *Analytical Biochemistry* 141:62-69 (1984).
Foran et al., "Differences in the Protease Activities of Tetanus and Botulinum B Toxins Revealed by the Cleavage of Vesicle-Associated Membrane Protein and Various Sized Fragments," *Biochemistry* 33:15365-15374 (1994).

(Continued)

*Primary Examiner*—Patricia A Duffy
(74) *Attorney, Agent, or Firm*—Dean G. Stathakis; Joel B. German; Allergan, Inc.

(57) ABSTRACT

The present invention provides clostridial toxin substrates useful in assaying for the protease activity of any clostridial toxin, including botulinum toxins of all serotypes as well as tetanus toxins. A clostridial toxin substrate of the invention contains a donor fluorophore; an acceptor having an absorbance spectrum overlapping the emission spectrum of the donor fluorophore; and a clostridial toxin recognition sequence that includes a cleavage site, where the cleavage site intervenes between the donor fluorophore and the acceptor and where, under the appropriate conditions, resonance energy transfer is exhibited between the donor fluorophore and the acceptor.

33 Claims, 8 Drawing Sheets

OTHER PUBLICATIONS

Geoghegan et al., "Fluorescence-based Continuous Assay for the Aspartyl Protease of Human Immunodeficiency Virus-1," *FEBS* 262:119-122 (1990).

Goudreau et al., "Dns-Gly-(*p*-NO$_2$)Phe-βAla, a Specific Fluorogenic Substrate for Neutral Endopeptidase 24.11," *Analytical Biochemistry* 219:87-95 (1994).

Hallis et al., "Development of Novel Assays for Botulinum Type A and B Neurotoxins Based on Their Endopeptidase Activities," *J. Clin. Microbiol.* 34:1934-1938 (1996).

Hanson and Stevens, "Cocrystal Structure of Synaptobrevin-II Bound to Botulinum Neurotoxin Type B at 2.0 Resolution," *Nature Structural Biology* 7:687-692 (2000).

Hodel, "Molecules in Focus: SNAP-25," *J. Biochem. & Cell Biol.* 30:1069-1073 (1998).

Holskin et al., "A Continuous Fluorescence-Based Assay of Human Cytomegalovirus Protease Using a Peptide Substrate," *Analytical Biochemistry* 226:148-155 (1995).

Humeau et al., "How Botulinum and Tetanus Neurotoxins Block Neurotransmitter Release," *Biochimie* 82:427-446 (2000).

Kakiuchi et al., "A High Throughput Assay of the Hepatitis C Virus Nonstructural Protein 3 Serine Proteinase," *Journal of Virological Methods* 80:77-84 (1999).

Knapp et al., The Crystal Structure of Botulinum Toxin A zinc Protease Domain, 37$^{th}$ *Annual Meeting of the Interagency Botulism Research Coordinating Committee* Asilomar, CA (2000).

Lacy et al., "Crystal Structure of Botulinum Neurotoxin Type A and Implications for Toxicity," *Nature Structural Biology* 5:898-902 (1998).

Le Bonniec et al., "Characterization of the P$_2$' and P$_3$' Specificities of Thrombin Using Fluorescence-Quenched Substrates and Mapping of the Subsites by Mutagenesis," *Biochemistry* 35:7114-7122 (1996).

Matayoshi et al., "Novel Fluorogenic Substrates for Assaying Retroviral Proteases by Resonance Energy Transfer," *Science* 247:954-958 (1990).

Matsumoto et al., "A High-Throughput Screening Utilizing Intramolecular Fluorescence Resonance Energy Transfer for the Discovery of the Molecules that Bind HIV-1 TAR RNA Specifically," *Bioorganic & Medicinal Chemistry Letters* 10:1857-1861 (2000).

Mahajan et al., "Novel Mutant Green Fluorescent Protein Protease Substrates Reveal the Activation of Specific Caspases During Apoptosis," *Chemistry & Biology* 6:401-409 (1999).

Montecucco and Schiavo, "Structure and Function of Tetanus and Botulinum Neurotoxins," *Quarterly Reviews of Biophysics* 28:423-472 (1995).

Niemann et al., "Clostridial Neurotoxins: New Tools for Dissecting Exocytosis," *Trends in Cell Biology* 4:179-185 (1994).

Olsen et al., "High-throughput Screening of Enzyme Libraries," *Curr. Opin. Biotechnol.* 11:331-337 (2000).

Pellizzari et al., "Tetanus and Botulinum Neurotoxins: Mechanism of Action and Therapeutic Uses," *Phil. Trans. R. Soc. Lond.* 354:259-268 (1999).

Rossetto et al., "Tetanus and Botulinum Neurotoxins: Turning Bad Guys Into Good by Research," *Toxicon* 39:27-41 (2001).

Schmidt et al., "Type A Botulinum Neurotoxin Proteolytic Activity: Development of Competitive Inhibitors and Implications for Substrate Specificity at the S$_1$' Binding Subsite," *FEBS Lett.* 435:61-64 (1998).

Schmidt and Bostian, "Proteolysis of Synthetic Peptides by Type A Botulinum Neurotoxin," *Journal of Protein Chemistry* 14:703-708 (1995).

Schmidt and Bostian, "Endoproteinase Activity of Type A Botulinum Neurotoxin: Substrate Requirements and Activation by Serum Albumin," *Journal of Protein Chemistry* 16:19-26 (1997).

Selvin, "The Renaissance of Fluorescence Resonance Energy Transfer," *Nature Structural Biology* 7:730-734 (2000).

Shone et al., "Proteolytic Cleavage of Synthetic Fragments of Vesicle-Associated Membrane Protein, Isoform-2 by Botulinum Type B Neurotoxin," *Eur. J. Biochem.* 217:965-971 (1993).

Sittampalam et al., "High-Throughput Screening: Advances in Assay Technologies," *Current Opinion in Chemical Biology* 1:384-391 (1997).

Swaminathan and Eswaramoorthy, "Structural Analysis of the Catalytic and Binding Sites of *Clostridium botulinum* Neurotoxin B," *Nature Structural Biology* 7:693-699 (2000).

Tawa et al., "Quantitative Analysis of Fluorescent Caspase Substrate Cleavage in Intact Cells and Identification of Novel Inhibitors of Apoptosis," *Cell Death and Differentiation* 8:30-37 (2001).

Vaidyanathan et al., "Proteolysis of SNAP-25 Isoforms by Botulinum Neurotoxin Types A, C and E: Domains and Amino Acid Residues Controlling the Formation of Enzyme-Substrate Complexes and Cleavage," *J. Neurochem.* 72:327-337 (1999).

Vitiello et al., "Intracellular Ribozyme-Catalyzed *Trans*-Cleavage of RNA Monitored by Fluorescence Resonance Energy Transfer," *RNA* 6:628-637 (2000).

Wang et al., "A Continuous Fluorescence Assay of Renin Activity," *Analytical Biochemistry* 210:351-359 (1993).

Wu and Brand, "Resonance Energy Transfer: Methods and Applications," *Analytical Biochemistry* 218:1-13 (1994).

Yamasaki et al., "Cleavage of Members of the Synaptobrevin/VAMP Family by Types D and F Botulinal Neurotoxins and Tetanus Toxin," *J. Biol. Chem.* 269:12764-12772 (1994).

Davydov et al, "Association of Cytochromes P450 with Their Reductases: Opposite Sign of the Electrostatis Interactions in P450BM-3 As Compared with the Microsomal 2B4 System", Biochemistry 39, 6489-6497, 2000.

Gorbenko, "Structure of cytochrome c complexes with phospholipids as revealed by resonance energy transfer", Biochimica et Biophysica Acta 1420, 1-13, 1999.

Gorbenko, "Resonance energy transfer study of hemoglobin complexes with model phospholipid membranes", Biophysical Chemistry 81, 93-105, 1999.

Hanbury et al, "Fiber-optic immunosensor for measurement of myoglobin", Clinical Chemistry, 43:11, 2128-2136, 1997.

Lepesheva et al, "Conformational dynamics and molecular interaction reactions of recombinant cytochrome P450scc (CYP11A1) detected by fluorescence energy transfer", Biochimical et Biophysica Acta 1434, 31-43, 1999.

Taylor et al, "Cascade Blue as a Donor for Resonance Energy Transfer Studies of Heme-Containing Proteins", Analytical Biochemistry 302, 19-27, 2002.

Tuominen et al, "ATP Induces a Conformational Change in Lipid-bound Cytochrome C*", The Journal of Biological Chemistry, 276, 22, 19356-19362, 2001.

* cited by examiner

```
                   1
VAMP-1 HUMAN    (1) MSAPAQPPAEGTEGTAPGGGPPGPPPNMTSNRRLQQTQAQVEEVDDIRVNVDKVLERDQKLSELDDRADALQ  75
VAMP-2 HUMAN    (1) ---NSATAAPPAAPAGEGGPPAPPPNLTSNRRLQQTQAQVDEVVDIMRVNVDKVLERDQKLSELDDRADALQ
VAMP-2 MOUSE    (1) ---NSATAAVPPAAPAGEGGPPAPPPNLTSNRRLQQTQAQVDEVVDIMRVNVDKVLERDQKLSELDDRADALQ
VAMP Bovine     (1) ---NSATAAPPAAPAGEGGPPAPPPNLTSNRRLQQTQAQVDEVVDIMRVNVDKVLERDQKLSELDDRADALQ
VAMP-2 Frog     (1) ---MSAPAAGPPAAPAQGDPAQQGPP-NLTSNRRLQQTQAQVDEVVDIMRVNVDKVLERDQKLSELDDRADALQ
VAMP Sea Urchin (1) ---------------MAALPPPQPAPSNKRLQQTQAQVEEVVDIMRVNVDKVLERDTALSVLDDRADALQQ 76
VAMP-1 HUMAN   (75) GASQFESSAAKLKRKYWWKNCKMMIMLGAICAIIVVVIVIFH--       123
VAMP-2 HUMAN   (73) GASQFETSAAKLKRKYWWKNLKMMIILGVICAIILIIIIVYFSS-
VAMP-2 MOUSE   (73) GASQFETSAAKLKRKYWWKNLKMMIILGVICAIILIIIIVYFSS-
VAMP Bovine    (73) GASQFETSAAKLKRKYWWKNLKMMIILGVICAIILIIIIVYFSS-
VAMP-2 Frog    (71) GASQFETSAAKLKRKYWWKNLKMMIMLGVICAIIVIIIIVYFST-
VAMP Sea Urchin(57) GASQFEINAGKLKRKYWWKNCKMMINLATIIVLLIAIVQSQKK
```

FIG. 7 sequence that includes a cleavage site, where the cleavage site intervenes between the donor fluorophore and the acceptor and where, under the appropriate conditions, resonance energy transfer is exhibited between the donor fluorophore and the acceptor. Such a clostridial toxin substrate can include, for example, a botulinum toxin recognition sequence. In one embodiment, a clostridial toxin substrate of the invention includes a botulinum toxin recognition sequence which is not a botulinum toxin serotype B (BoNT/B) recognition sequence.

SEQUENCE LISTING

<160> NUMBER OF SEQ ID NOS: 96

<210> SEQ ID NO 1
<211> LENGTH: 8
<212> TYPE: PRT
<213> ORGANISM: Artificial Sequence
<220> FEATURE:
<223> OTHER INFORMATION: synthetic construct

<400> SEQUENCE: 1

Glu Ala Asn Gln Arg Ala Thr Lys
 1               5

<210> SEQ ID NO 2
<211> LENGTH: 206
<212> TYPE: PRT
<213> ORGANISM: Homo sapiens

<400> SEQUENCE: 2

Met Ala Glu Asp Ala Asp Met Arg Asn Glu Leu Glu Met Gln Arg
 1               5                  10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
        50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 3
<211> LENGTH: 8
<212> TYPE: PRT
<213> ORGANISM: Artificial Sequence
<220> FEATURE:
<223> OTHER INFORMATION: synthetic construct

<400> SEQUENCE: 3

Gly Ala Ser Gln Phe Glu Thr Ser
 1               5

```
<210> SEQ ID NO 4
<211> LENGTH: 116
<212> TYPE: PRT
<213> ORGANISM: Homo sapiens

<400> SEQUENCE: 4

Met Ser Ala Thr Ala Ala Thr Ala Pro Pro Ala Ala Pro Ala Gly Glu
 1               5                  10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
 50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                 85                  90                  95

Ile Ile Leu Gly Val Ile Cys Ala Ile Ile Leu Ile Ile Ile Ile Val
            100                 105                 110

Tyr Phe Ser Ser
        115

<210> SEQ ID NO 5
<211> LENGTH: 8
<212> TYPE: PRT
<213> ORGANISM: Artificial Sequence
<220> FEATURE:
<223> OTHER INFORMATION: synthetic construct

<400> SEQUENCE: 5

Asp Thr Lys Lys Ala Val Lys Trp
 1               5

<210> SEQ ID NO 6
<211> LENGTH: 8
<212> TYPE: PRT
<213> ORGANISM: Artificial Sequence
<220> FEATURE:
<223> OTHER INFORMATION: synthetic construct

<400> SEQUENCE: 6

Arg Asp Gln Lys Leu Ser Glu Leu
 1               5

<210> SEQ ID NO 7
<211> LENGTH: 206
<212> TYPE: PRT
<213> ORGANISM: Rattus sp.

<400> SEQUENCE: 7

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
 50                  55                  60

Asp Gln Ile Asn Lys Asp Met Lys Glu Ala Glu Lys Asn Leu Thr Asp
 65                  70                  75                  80
```

```
Leu Gly Lys Phe Cys Gly Leu Cys Val Cys Pro Cys Asn Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205

<210> SEQ ID NO 8
<211> LENGTH: 8
<212> TYPE: PRT
<213> ORGANISM: Artificial Sequence
<220> FEATURE:
<223> OTHER INFORMATION: synthetic construct

<400> SEQUENCE: 8

Gln Ile Asp Arg Ile Met Glu Lys
 1               5

<210> SEQ ID NO 9
<211> LENGTH: 8
<212> TYPE: PRT
<213> ORGANISM: Artificial Sequence
<220> FEATURE:
<223> OTHER INFORMATION: synthetic construct

<400> SEQUENCE: 9

Glu Arg Asp Gln Lys Leu Ser Glu
 1               5

<210> SEQ ID NO 10
<211> LENGTH: 8
<212> TYPE: PRT
<213> ORGANISM: Artificial Sequence
<220> FEATURE:
<223> OTHER INFORMATION: synthetic construct

<400> SEQUENCE: 10

Glu Thr Ser Ala Ala Lys Leu Lys
 1               5

<210> SEQ ID NO 11
<211> LENGTH: 8
<212> TYPE: PRT
<213> ORGANISM: Artificial Sequence
<220> FEATURE:
<223> OTHER INFORMATION: synthetic construct

<400> SEQUENCE: 11

Gly Ala Ser Gln Phe Glu Thr Ser
 1               5
```

<210> SEQ ID NO 12
<211> LENGTH: 206
<212> TYPE: PRT
<213> ORGANISM: Mus musculus

<400> SEQUENCE: 12

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 13
<211> LENGTH: 212
<212> TYPE: PRT
<213> ORGANISM: Drosophila sp.

<400> SEQUENCE: 13

Met Pro Ala Asp Pro Ser Glu Glu Val Ala Pro Gln Val Pro Lys Thr
1               5                   10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
    50                  55                  60

Asp Arg Ile Glu Glu Gly Met Asp Gln Ile Asn Ala Asp Met Arg Glu
65                  70                  75                  80

Ala Glu Lys Asn Leu Ser Gly Met Glu Lys Cys Cys Gly Ile Cys Val
                85                  90                  95

Leu Pro Cys Asn Lys Ser Gln Ser Phe Lys Glu Asp Asp Gly Thr Trp
            100                 105                 110

Lys Gly Asn Asp Asp Gly Lys Val Val Asn Asn Gln Pro Gln Arg Val
        115                 120                 125

```
Met Asp Asp Arg Asn Gly Met Met Ala Gln Ala Gly Tyr Ile Gly Arg
    130                 135                 140

Ile Thr Asn Asp Ala Arg Glu Asp Met Glu Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
    210

<210> SEQ ID NO 14
<211> LENGTH: 203
<212> TYPE: PRT
<213> ORGANISM: Carassius auratus

<400> SEQUENCE: 14

Met Ala Asp Glu Ala Asp Met Arg Asn Glu Leu Thr Asp Met Gln Ala
1               5                   10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200

<210> SEQ ID NO 15
<211> LENGTH: 212
<212> TYPE: PRT
<213> ORGANISM: Strongylocentrotus purpuratus

<400> SEQUENCE: 15

Met Glu Asp Gln Asn Asp Met Asn Met Arg Ser Glu Leu Glu Glu Ile
1               5                   10                  15

Gln Met Gln Ser Asn Met Gln Thr Asp Glu Ser Leu Glu Ser Thr Arg
            20                  25                  30
```

```
Arg Met Leu Gln Met Ala Glu Glu Ser Gln Asp Met Gly Ile Lys Thr
        35                  40                  45

Leu Val Met Leu Asp Glu Gln Gly Glu Gln Leu Asp Arg Ile Glu Glu
 50                  55                  60

Gly Met Asp Gln Ile Asn Thr Asp Met Arg Glu Ala Glu Lys Asn Leu
 65                  70                  75                  80

Thr Gly Leu Glu Lys Cys Cys Gly Ile Cys Val Cys Pro Trp Lys Lys
                 85                  90                  95

Leu Gly Asn Phe Glu Lys Gly Asp Asp Tyr Lys Lys Thr Trp Lys Gly
            100                 105                 110

Asn Asp Asp Gly Lys Val Asn Ser His Gln Pro Met Arg Met Glu Asp
        115                 120                 125

Asp Arg Asp Gly Cys Gly Gly Asn Ala Ser Met Ile Thr Arg Ile Thr
130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210

<210> SEQ ID NO 16
<211> LENGTH: 249
<212> TYPE: PRT
<213> ORGANISM: Gallus gallus

<400> SEQUENCE: 16

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
 50                  55                  60

Asn His Ile Asn Gln Asp Met Lys Glu Ala Glu Lys Asn Leu Lys Asp
 65                  70                  75                  80

Leu Gly Lys Cys Cys Gly Leu Phe Ile Cys Pro Cys Asn Lys Leu Lys
                 85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Leu Ile Pro Ile Lys Pro Gly Leu
            180                 185                 190
```

```
Met Lys Pro Thr Ser Val Gln Gln Arg Cys Ser Ala Val Val Lys Cys
            195                 200                 205

Ser Lys Val His Phe Leu Leu Met Leu Ser Gln Arg Ala Val Pro Ser
            210                 215                 220

Cys Phe Tyr His Gly Ile Tyr Leu Leu Gly Leu His Thr Cys Thr Tyr
225                 230                 235                 240

Gln Pro His Cys Lys Cys Cys Pro Val
                245
```

<210> SEQ ID NO 17
<211> LENGTH: 116
<212> TYPE: PRT
<213> ORGANISM: Mus musculus

<400> SEQUENCE: 17

```
Met Ser Ala Thr Ala Ala Thr Val Pro Pro Ala Ala Pro Ala Gly Glu
  1               5                  10                  15

Gly Gly Pro Pro Ala Pro Pro Pro Asn Leu Thr Ser Asn Arg Arg Leu
             20                  25                  30

Gln Gln Thr Gln Ala Gln Val Asp Glu Val Val Asp Ile Met Arg Val
         35                  40                  45

Asn Val Asp Lys Val Leu Glu Arg Asp Gln Lys Leu Ser Glu Leu Asp
 50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                 85                  90                  95

Ile Ile Leu Gly Val Ile Cys Ala Ile Ile Leu Ile Ile Ile Ile Val
            100                 105                 110

Tyr Phe Ser Thr
            115
```

<210> SEQ ID NO 18
<211> LENGTH: 116
<212> TYPE: PRT
<213> ORGANISM: Bos taurus

<400> SEQUENCE: 18

```
Met Ser Ala Thr Ala Ala Thr Ala Pro Pro Ala Ala Pro Ala Gly Glu
  1               5                  10                  15

Gly Gly Pro Pro Ala Pro Pro Pro Asn Leu Thr Ser Asn Arg Arg Leu
             20                  25                  30

Gln Gln Thr Gln Ala Gln Val Asp Glu Val Val Asp Ile Met Arg Val
         35                  40                  45

Asn Val Asp Lys Val Leu Glu Arg Asp Gln Lys Leu Ser Glu Leu Asp
 50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                 85                  90                  95

Ile Ile Leu Gly Val Ile Cys Ala Ile Ile Leu Ile Ile Ile Ile Val
            100                 105                 110

Tyr Phe Ser Ser
            115
```

<210> SEQ ID NO 19
<211> LENGTH: 114
<212> TYPE: PRT
<213> ORGANISM: Xenopus laevis

<400> SEQUENCE: 19

Met Ser Ala Pro Ala Gly Pro Pro Ala Ala Pro Gly Asp Gly
1               5                   10                  15

Ala Pro Gln Gly Pro Pro Asn Leu Thr Ser Asn Arg Arg Leu Gln Gln
            20                  25                  30

Thr Gln Ala Gln Val Asp Glu Val Val Asp Ile Met Arg Val Asn Val
        35                  40                  45

Asp Lys Val Leu Glu Arg Asp Thr Lys Leu Ser Glu Leu Asp Asp Arg
    50                  55                  60

Ala Asp Ala Leu Gln Ala Gly Ala Ser Gln Phe Glu Thr Ser Ala Ala
65                  70                  75                  80

Lys Leu Lys Arg Lys Tyr Trp Trp Lys Asn Met Lys Met Met Ile Ile
                85                  90                  95

Met Gly Val Ile Cys Ala Ile Ile Leu Ile Ile Ile Val Tyr Phe
            100                 105                 110

Ser Thr

<210> SEQ ID NO 20
<211> LENGTH: 104
<212> TYPE: PRT
<213> ORGANISM: Strongylocentrotus purpuratus

<400> SEQUENCE: 20

Met Ala Ala Pro Pro Pro Gln Pro Ala Pro Ser Asn Lys Arg Leu
1               5                   10                  15

Gln Gln Thr Gln Ala Gln Val Asp Glu Val Val Asp Ile Met Arg Val
            20                  25                  30

Asn Val Asp Lys Val Leu Glu Arg Asp Gln Ala Leu Ser Val Leu Asp
        35                  40                  45

Asp Arg Ala Asp Ala Leu Gln Gln Gly Ala Ser Gln Phe Glu Thr Asn
    50                  55                  60

Ala Gly Lys Leu Lys Arg Lys Tyr Trp Trp Lys Asn Cys Lys Met Met
65                  70                  75                  80

Ile Ile Leu Ala Ile Ile Ile Val Ile Leu Ile Ile Ile Val
                85                  90                  95

Ala Ile Val Gln Ser Gln Lys Lys
            100

<210> SEQ ID NO 21
<211> LENGTH: 288
<212> TYPE: PRT
<213> ORGANISM: Homo sapiens

<400> SEQUENCE: 21

Met Lys Asp Arg Thr Gln Glu Leu Arg Thr Ala Lys Asp Ser Asp Asp
1               5                   10                  15

Asp Asp Asp Val Ala Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
            115                 120                 125

Glu Val Met Ser Glu Tyr Asn Ala Thr Gln Ser Asp Tyr Arg Glu Arg
        130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
            195                 200                 205

Ile Arg Glu Leu His Asp Met Phe Met Asp Met Ala Met Leu Val Glu
210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Val Ile Ala Ser Thr Val Gly Gly Ile Phe Ala
            275                 280                 285

<210> SEQ ID NO 22
<211> LENGTH: 288
<212> TYPE: PRT
<213> ORGANISM: Homo sapiens

<400> SEQUENCE: 22

Met Lys Asp Arg Thr Gln Glu Leu Arg Ser Ala Lys Asp Ser Asp Asp
1               5                   10                  15

Glu Glu Glu Val Val His Val Asp Arg Asp His Phe Met Asp Glu Phe
                20                  25                  30

Phe Glu Gln Val Glu Glu Ile Arg Gly Cys Ile Glu Lys Leu Ser Glu
            35                  40                  45

Asp Val Glu Gln Val Lys Lys Gln His Ser Ala Ile Leu Ala Ala Pro
        50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
            115                 120                 125

Val Met Thr Glu Tyr Asn Ala Thr Gln Ser Lys Tyr Arg Asp Arg Cys
        130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285

<210> SEQ ID NO 23
<211> LENGTH: 288
<212> TYPE: PRT
<213> ORGANISM: Mus musculus

<400> SEQUENCE: 23

Met Lys Asp Arg Thr Gln Glu Leu Arg Thr Ala Lys Asp Ser Asp Asp
1               5                   10                  15

Asp Asp Asp Val Thr Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Thr Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

```
Tyr Gln Ser Lys Ala Arg Arg Lys Lys Ile Met Ile Ile Cys Cys
            260                 265                 270

Val Ile Leu Gly Ile Ile Ile Ala Ser Thr Ile Gly Gly Ile Phe Gly
            275                 280                 285

<210> SEQ ID NO 24
<211> LENGTH: 291
<212> TYPE: PRT
<213> ORGANISM: Drosophila sp.

<400> SEQUENCE: 24

Met Thr Lys Asp Arg Leu Ala Ala Leu His Ala Ala Gln Ser Asp Asp
  1               5                  10                  15

Glu Glu Glu Thr Glu Val Ala Val Asn Val Asp Gly His Asp Ser Tyr
                 20                  25                  30

Met Asp Asp Phe Phe Ala Gln Val Glu Glu Ile Arg Gly Met Ile Asp
             35                  40                  45

Lys Val Gln Asp Asn Val Glu Glu Val Lys Lys Lys His Ser Ala Ile
         50                  55                  60

Leu Ser Ala Pro Gln Thr Asp Glu Lys Thr Lys Gln Glu Leu Glu Asp
 65                  70                  75                  80

Leu Met Ala Asp Ile Lys Lys Asn Ala Asn Arg Val Arg Gly Lys Leu
                 85                  90                  95

Lys Gly Ile Glu Gln Asn Ile Glu Gln Glu Glu Gln Asn Lys Ser
            100                 105                 110

Ser Ala Asp Leu Arg Ile Arg Lys Thr Gln His Ser Thr Leu Ser Arg
            115                 120                 125

Lys Phe Val Glu Val Met Thr Glu Tyr Asn Arg Thr Gln Thr Asp Tyr
            130                 135                 140

Arg Glu Arg Cys Lys Gly Arg Ile Gln Arg Gln Leu Glu Ile Thr Gly
145                 150                 155                 160

Arg Pro Thr Asn Asp Asp Glu Leu Glu Lys Met Leu Glu Glu Gly Asn
                165                 170                 175

Ser Ser Val Phe Thr Gln Gly Ile Ile Met Glu Thr Gln Ala Lys
            180                 185                 190

Gln Thr Leu Ala Asp Ile Glu Ala Arg His Gln Asp Ile Met Lys Leu
            195                 200                 205

Glu Thr Ser Ile Lys Glu Leu His Asp Met Phe Met Asp Met Ala Met
            210                 215                 220

Leu Val Glu Ser Gln Gly Glu Met Ile Asp Arg Ile Glu Tyr His Val
225                 230                 235                 240

Glu His Ala Met Asp Tyr Val Gln Thr Ala Thr Gln Asp Thr Lys Lys
                245                 250                 255

Ala Leu Lys Tyr Gln Ser Lys Ala Arg Arg Lys Lys Ile Met Ile Leu
            260                 265                 270

Ile Cys Leu Thr Val Leu Gly Ile Leu Ala Ala Ser Tyr Val Ser Ser
            275                 280                 285

Tyr Phe Met
    290

<210> SEQ ID NO 25
<211> LENGTH: 291
<212> TYPE: PRT
<213> ORGANISM: Caenorhabditis elegans
```

<400> SEQUENCE: 25

```
Met Thr Lys Asp Arg Leu Ser Ala Leu Lys Ala Ala Gln Ser Glu Asp
 1               5                  10                  15
Glu Gln Asp Asp Met His Met Asp Thr Gly Asn Ala Gln Tyr Met
             20                  25                  30
Glu Glu Phe Phe Glu Gln Val Glu Glu Ile Arg Gly Ser Val Asp Ile
         35                  40                  45
Ile Ala Asn Asn Val Glu Glu Val Lys Lys Lys His Ser Ala Ile Leu
 50                  55                  60
Ser Asn Pro Val Asn Asp Gln Lys Thr Lys Glu Glu Leu Asp Glu Leu
 65                  70                  75                  80
Met Ala Val Ile Lys Arg Ala Ala Asn Lys Val Arg Gly Lys Leu Lys
                 85                  90                  95
Leu Ile Glu Asn Ala Ile Asp His Asp Glu Gln Gly Ala Gly Asn Ala
            100                 105                 110
Asp Leu Arg Ile Arg Lys Thr Gln His Ser Thr Leu Ser Arg Arg Phe
        115                 120                 125
Val Glu Val Met Thr Asp Tyr Asn Lys Thr Gln Thr Asp Tyr Arg Glu
    130                 135                 140
Arg Cys Lys Gly Arg Ile Gln Arg Gln Leu Asp Ile Ala Gly Lys Gln
145                 150                 155                 160
Val Gly Asp Glu Asp Leu Glu Met Ile Glu Ser Gly Asn Pro Gly
                165                 170                 175
Val Phe Thr Gln Gly Ile Ile Thr Asp Thr Gln Ala Lys Gln Thr
            180                 185                 190
Leu Ala Asp Ile Glu Ala Arg His Asn Asp Ile Met Lys Leu Glu Ser
        195                 200                 205
Ser Ile Arg Glu Leu His Asp Met Phe Met Asp Met Ala Met Leu Val
    210                 215                 220
Glu Ser Gln Gly Glu Met Val Asp Arg Ile Glu Tyr Asn Val Glu His
225                 230                 235                 240
Ala Lys Glu Phe Val Asp Arg Ala Val Ala Asp Thr Lys Lys Ala Val
                245                 250                 255
Gln Tyr Gln Ser Lys Ala Arg Arg Lys Lys Ile Cys Ile Leu Val Thr
            260                 265                 270
Gly Val Ile Leu Ile Thr Gly Leu Ile Ile Phe Ile Leu Phe Tyr Ala
        275                 280                 285
Lys Val Leu
    290
```

<210> SEQ ID NO 26
<211> LENGTH: 288
<212> TYPE: PRT
<213> ORGANISM: Strongylocentrotus purpuratus

<400> SEQUENCE: 26

```
Met Arg Asp Arg Leu Gly Ser Leu Lys Arg Asn Glu Glu Asp Asp Val
 1               5                  10                  15
Gly Pro Glu Val Ala Val Asn Val Glu Ser Glu Lys Phe Met Glu Glu
             20                  25                  30
Phe Phe Glu Gln Val Glu Glu Val Arg Asn Asn Ile Asp Lys Ile Ser
         35                  40                  45
Lys Asn Val Asp Glu Val Lys Lys Lys His Ser Asp Ile Leu Ser Ala
 50                  55                  60
```

```
            Pro Gln Ala Asp Glu Lys Val Lys Asp Glu Leu Glu Leu Met Ser
            65                  70                  75                  80

Asp Ile Lys Lys Thr Ala Asn Lys Val Arg Ala Lys Leu Lys Met Met
                            85                  90                  95

Glu Gln Ser Ile Glu Gln Glu Ser Ala Lys Met Asn Ser Ala Asp
                        100                 105                 110

Val Arg Ile Arg Lys Thr Gln His Ser Thr Leu Ser Arg Lys Phe Val
                    115                 120                 125

Glu Val Met Thr Asp Tyr Asn Ser Thr Gln Thr Asp Tyr Arg Glu Arg
                130                 135                 140

Cys Lys Gly Arg Ile Gln Arg Gln Leu Glu Ile Thr Gly Lys Ser Thr
            145                 150                 155                 160

Thr Asp Ala Glu Leu Glu Asp Met Leu Glu Ser Gly Asn Pro Ala Ile
                            165                 170                 175

Phe Thr Ser Gly Ile Ile Met Asp Thr Gln Gln Ala Lys Gln Thr Leu
                        180                 185                 190

Arg Asp Ile Glu Ala Arg His Asn Asp Ile Ile Lys Leu Glu Ser Ser
                    195                 200                 205

Ile Arg Glu Leu His Asp Met Phe Met Asp Met Ala Met Leu Val Glu
                210                 215                 220

Ser Gln Gly Glu Met Ile Asp Arg Ile Glu Tyr Asn Val Glu Gln Ser
            225                 230                 235                 240

Val Asp Tyr Val Glu Thr Ala Lys Met Asp Thr Lys Lys Ala Val Lys
                            245                 250                 255

Tyr Gln Ser Lys Ala Arg Arg Lys Lys Phe Tyr Ile Ala Ile Cys Cys
                        260                 265                 270

Gly Val Ala Leu Gly Ile Leu Val Leu Val Leu Ile Ile Val Leu Ala
                    275                 280                 285

<210> SEQ ID NO 27
<211> LENGTH: 13
<212> TYPE: PRT
<213> ORGANISM: Homo sapiens

<400> SEQUENCE: 27

Thr Arg Ile Asp Glu Ala Asn Gln Arg Ala Thr Lys Met
            1               5                   10

<210> SEQ ID NO 28
<211> LENGTH: 15
<212> TYPE: PRT
<213> ORGANISM: Homo sapiens

<400> SEQUENCE: 28

Ser Asn Lys Thr Arg Ile Asp Glu Ala Asn Gln Arg Ala Thr Lys
            1               5                   10                  15

<210> SEQ ID NO 29
<211> LENGTH: 16
<212> TYPE: PRT
<213> ORGANISM: Homo sapiens

<400> SEQUENCE: 29

Ser Asn Lys Thr Arg Ile Asp Glu Ala Asn Gln Arg Ala Thr Lys Met
            1               5                   10                  15
```

```
<210> SEQ ID NO 30
<211> LENGTH: 17
<212> TYPE: PRT
<213> ORGANISM: Homo sapiens

<400> SEQUENCE: 30

Ser Asn Lys Thr Arg Ile Asp Glu Ala Asn Gln Arg Ala Thr Lys Met
1               5                   10                  15

Leu

<210> SEQ ID NO 31
<211> LENGTH: 17
<212> TYPE: PRT
<213> ORGANISM: Homo sapiens

<400> SEQUENCE: 31

Asp Ser Asn Lys Thr Arg Ile Asp Glu Ala Asn Gln Arg Ala Thr Lys
1               5                   10                  15

Met

<210> SEQ ID NO 32
<211> LENGTH: 18
<212> TYPE: PRT
<213> ORGANISM: Homo sapiens

<400> SEQUENCE: 32

Asp Ser Asn Lys Thr Arg Ile Asp Glu Ala Asn Gln Arg Ala Thr Lys
1               5                   10                  15

Met Leu

<210> SEQ ID NO 33
<211> LENGTH: 33
<212> TYPE: PRT
<213> ORGANISM: Mus musculus

<400> SEQUENCE: 33

Gln Asn Arg Gln Ile Asp Arg Ile Met Glu Lys Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 34
<211> LENGTH: 32
<212> TYPE: PRT
<213> ORGANISM: Homo sapiens

<400> SEQUENCE: 34

Gln Asn Pro Gln Ile Lys Arg Ile Thr Asp Lys Ala Asp Thr Asn Arg
1               5                   10                  15

Asp Arg Ile Asp Ile Ala Asn Ala Arg Ala Lys Lys Leu Ile Asp Ser
            20                  25                  30

<210> SEQ ID NO 35
<211> LENGTH: 32
<212> TYPE: PRT
<213> ORGANISM: Mus musculus
```

<400> SEQUENCE: 35

Gln Asn Gln Gln Ile Gln Lys Ile Thr Glu Lys Ala Asp Thr Asn Lys
1               5                   10                  15

Asn Arg Ile Asp Ile Ala Asn Thr Arg Ala Lys Lys Leu Ile Asp Ser
            20                  25                  30

<210> SEQ ID NO 36
<211> LENGTH: 34
<212> TYPE: PRT
<213> ORGANISM: Gallus gallus

<400> SEQUENCE: 36

Gln Asn Arg Gln Ile Asp Arg Ile Met Glu Lys Leu Ile Pro Ile Lys
1               5                   10                  15

Pro Gly Leu Met Lys Pro Thr Ser Val Gln Gln Arg Cys Ser Ala Val
            20                  25                  30

Val Lys

<210> SEQ ID NO 37
<211> LENGTH: 33
<212> TYPE: PRT
<213> ORGANISM: Carassius auratus

<400> SEQUENCE: 37

Gln Asn Arg Gln Ile Asp Arg Ile Met Asp Met Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 38
<211> LENGTH: 33
<212> TYPE: PRT
<213> ORGANISM: Carassius auratus

<400> SEQUENCE: 38

Gln Asn Arg Gln Ile Asp Arg Ile Met Glu Lys Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 39
<211> LENGTH: 30
<212> TYPE: PRT
<213> ORGANISM: Torpedo sp.

<400> SEQUENCE: 39

Gln Asn Ala Gln Val Asp Arg Ile Val Val Lys Gly Asp Met Asn Lys
1               5                   10                  15

Ala Arg Ile Asp Glu Ala Asn Lys His Ala Thr Lys Met Leu
            20                  25                  30

<210> SEQ ID NO 40
<211> LENGTH: 33
<212> TYPE: PRT
<213> ORGANISM: Strongylocentrotus purpuratus

```
<400> SEQUENCE: 40

Gln Asn Ser Gln Val Gly Arg Ile Thr Ser Lys Ala Glu Ser Asn Glu
 1               5                  10                  15

Gly Arg Ile Asn Ser Ala Asp Lys Arg Ala Lys Asn Ile Leu Arg Asn
            20                  25                  30

Lys

<210> SEQ ID NO 41
<211> LENGTH: 31
<212> TYPE: PRT
<213> ORGANISM: Caenorhabditis elagans

<400> SEQUENCE: 41

Gln Asn Arg Gln Leu Asp Arg Ile His Asp Lys Gln Ser Asn Glu Val
 1               5                  10                  15

Arg Val Glu Ser Ala Asn Lys Arg Ala Lys Asn Leu Ile Thr Lys
            20                  25                  30

<210> SEQ ID NO 42
<211> LENGTH: 31
<212> TYPE: PRT
<213> ORGANISM: Drosophila sp.

<400> SEQUENCE: 42

Gln Asn Arg Gln Ile Asp Arg Ile Asn Arg Lys Gly Glu Ser Asn Glu
 1               5                  10                  15

Ala Arg Ile Ala Val Ala Asn Gln Arg Ala His Gln Leu Leu Lys
            20                  25                  30

<210> SEQ ID NO 43
<211> LENGTH: 32
<212> TYPE: PRT
<213> ORGANISM: Hirudinida sp.

<400> SEQUENCE: 43

Gln Asn Arg Gln Val Asp Arg Ile Asn Asn Lys Met Thr Ser Asn Gln
 1               5                  10                  15

Leu Arg Ile Ser Asp Ala Asn Lys Arg Ala Ser Lys Leu Leu Lys Glu
            20                  25                  30

<210> SEQ ID NO 44
<211> LENGTH: 17
<212> TYPE: PRT
<213> ORGANISM: Artificial Sequence
<220> FEATURE:
<223> OTHER INFORMATION: synthetic peptide

<400> SEQUENCE: 44

Ser Asn Lys Thr Arg Ile Asp Glu Ala Asn Gln Arg Ala Thr Lys Ala
 1               5                  10                  15

Leu

<210> SEQ ID NO 45
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 16
<223> OTHER INFORMATION: Xaa=Nle
```

```
<400> SEQUENCE: 45

Ser Asn Lys Thr Arg Ile Asp Glu Ala Asn Gln Arg Ala Thr Lys Xaa
1               5                   10                  15

Leu

<210> SEQ ID NO 46
<211> LENGTH: 17
<212> TYPE: PRT
<213> ORGANISM: Artificial Sequence
<220> FEATURE:
<223> OTHER INFORMATION: synthetic peptide

<400> SEQUENCE: 46

Ser Asn Lys Thr Arg Ile Asp Glu Ala Asn Gln Arg Ala Thr Ala Met
1               5                   10                  15

Leu

<210> SEQ ID NO 47
<211> LENGTH: 17
<212> TYPE: PRT
<213> ORGANISM: Artificial Sequence
<220> FEATURE:
<223> OTHER INFORMATION: synthetic peptide

<400> SEQUENCE: 47

Ser Asn Lys Thr Arg Ile Asp Glu Ala Asn Gln Arg Ala Ser Lys Met
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 14
<223> OTHER INFORMATION: Xaa=Abu

<400> SEQUENCE: 48

Ser Asn Lys Thr Arg Ile Asp Glu Ala Asn Gln Arg Ala Xaa Lys Met
1               5                   10                  15

Leu

<210> SEQ ID NO 49
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 13
<223> OTHER INFORMATION: Xaa=Abu

<400> SEQUENCE: 49

Ser Asn Lys Thr Arg Ile Asp Glu Ala Asn Gln Arg Xaa Thr Lys Met
1               5                   10                  15

Leu
```

```
<210> SEQ ID NO 50
<211> LENGTH: 17
<212> TYPE: PRT
<213> ORGANISM: Artificial Sequence
<220> FEATURE:
<223> OTHER INFORMATION: synthetic peptide

<400> SEQUENCE: 50

Ser Asn Lys Thr Arg Ile Asp Glu Ala Asn Ala Arg Ala Thr Lys Met
 1               5                  10                  15

Leu

<210> SEQ ID NO 51
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 11
<223> OTHER INFORMATION: Xaa=Abu

<400> SEQUENCE: 51

Ser Asn Lys Thr Arg Ile Asp Glu Ala Asn Xaa Ala Thr Lys Met Leu
 1               5                  10                  15

<210> SEQ ID NO 52
<211> LENGTH: 17
<212> TYPE: PRT
<213> ORGANISM: Artificial Sequence
<220> FEATURE:
<223> OTHER INFORMATION: synthetic peptide

<400> SEQUENCE: 52

Ser Asn Lys Thr Arg Ile Asp Glu Ala Asn Asn Arg Ala Thr Lys Met
 1               5                  10                  15

Leu

<210> SEQ ID NO 53
<211> LENGTH: 17
<212> TYPE: PRT
<213> ORGANISM: Artificial Sequence
<220> FEATURE:
<223> OTHER INFORMATION: synthetic peptide

<400> SEQUENCE: 53

Ser Asn Lys Thr Arg Ile Asp Glu Ala Ala Gln Arg Ala Thr Lys Met
 1               5                  10                  15

Leu

<210> SEQ ID NO 54
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 9
<223> OTHER INFORMATION: Xaa=Abu

<400> SEQUENCE: 54

Ser Asn Lys Thr Arg Ile Asp Glu Xaa Asn Gln Arg Ala Thr Lys Met
 1               5                  10                  15

Leu
```

```
<210> SEQ ID NO 55
<211> LENGTH: 17
<212> TYPE: PRT
<213> ORGANISM: Artificial Sequence
<220> FEATURE:
<223> OTHER INFORMATION: synthetic peptide

<400> SEQUENCE: 55

Ser Asn Lys Thr Arg Ile Asp Gln Ala Asn Gln Arg Ala Thr Lys Met
1               5                   10                  15

Leu

<210> SEQ ID NO 56
<211> LENGTH: 17
<212> TYPE: PRT
<213> ORGANISM: Artificial Sequence
<220> FEATURE:
<223> OTHER INFORMATION: synthetic peptide

<400> SEQUENCE: 56

Ser Asn Lys Thr Arg Ile Asn Glu Ala Asn Gln Arg Ala Thr Lys Met
1               5                   10                  15

Leu

<210> SEQ ID NO 57
<211> LENGTH: 40
<212> TYPE: PRT
<213> ORGANISM: Homo sapiens

<400> SEQUENCE: 57

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Ser Ser Ala Ala
                20                  25                  30

Lys Leu Lys Arg Lys Tyr Trp Trp
            35                  40

<210> SEQ ID NO 58
<211> LENGTH: 40
<212> TYPE: PRT
<213> ORGANISM: Bos taurus

<400> SEQUENCE: 58

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
                20                  25                  30

Lys Leu Lys Arg Lys Tyr Trp Trp
            35                  40

<210> SEQ ID NO 59
<211> LENGTH: 40
<212> TYPE: PRT
<213> ORGANISM: Rattus sp.

<400> SEQUENCE: 59

Asp Lys Val Leu Glu Arg Asp Gln Lys Leu Ser Glu Leu Asp Asp Arg
1               5                   10                  15

Ala Asp Ala Leu Gln Ala Gly Ala Ser Val Phe Glu Ser Ser Ala Ala
                20                  25                  30

Lys Leu Lys Arg Lys Tyr Trp Trp
            35                  40
```

```
<210> SEQ ID NO 60
<211> LENGTH: 40
<212> TYPE: PRT
<213> ORGANISM: Rattus sp.

<400> SEQUENCE: 60

Asp Lys Val Leu Glu Arg Asp Gln Lys Leu Ser Glu Leu Asp Asp Arg
 1               5                  10                  15
Ala Asp Ala Leu Gln Ala Gly Ala Ser Gln Phe Glu Thr Ser Ala Ala
            20                  25                  30
Lys Leu Lys Arg Lys Tyr Trp Trp
        35                  40

<210> SEQ ID NO 61
<211> LENGTH: 40
<212> TYPE: PRT
<213> ORGANISM: Rattus sp.

<400> SEQUENCE: 61

Asp Lys Val Leu Glu Arg Asp Gln Lys Leu Ser Glu Leu Asp Asp Arg
 1               5                  10                  15
Ala Asp Ala Leu Gln Ala Gly Ala Ser Gln Phe Glu Thr Ser Ala Ala
            20                  25                  30
Lys Leu Lys Arg Lys Tyr Trp Trp
        35                  40

<210> SEQ ID NO 62
<211> LENGTH: 40
<212> TYPE: PRT
<213> ORGANISM: Rattus sp.

<400> SEQUENCE: 62

Asp Leu Val Ala Gln Arg Gly Glu Arg Leu Glu Leu Ile Asp Lys
 1               5                  10                  15
Thr Glu Asn Leu Val Asp Ser Ser Val Thr Phe Lys Thr Ser Arg
            20                  25                  30
Asn Leu Ala Arg Ala Met Cys Met
        35                  40

<210> SEQ ID NO 63
<211> LENGTH: 32
<212> TYPE: PRT
<213> ORGANISM: Gallus gallus

<400> SEQUENCE: 63

Glu Arg Asp Gln Lys Leu Ser Glu Leu Asp Asp Arg Ala Asp Ala Leu
 1               5                  10                  15
Gln Ala Gly Ala Ser Val Phe Glu Ser Ser Ala Ala Lys Leu Lys Arg
            20                  25                  30

<210> SEQ ID NO 64
<211> LENGTH: 32
<212> TYPE: PRT
<213> ORGANISM: Gallus gallus

<400> SEQUENCE: 64

Glu Arg Asp Gln Lys Leu Ser Glu Leu Asp Asp Arg Ala Asp Ala Leu
 1               5                  10                  15
Gln Ala Gly Ala Ser Gln Phe Glu Thr Ser Ala Ala Lys Leu Lys Arg
            20                  25                  30
```

<210> SEQ ID NO 65
<211> LENGTH: 40
<212> TYPE: PRT
<213> ORGANISM: Torpedo sp.

<400> SEQUENCE: 65

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Ser Ser Ala Ala
            20                  25                  30

Lys Leu Lys Arg Lys Tyr Trp Trp
        35                  40

<210> SEQ ID NO 66
<211> LENGTH: 40
<212> TYPE: PRT
<213> ORGANISM: Strongylocentrotus purpuratus

<400> SEQUENCE: 66

Asp Lys Val Leu Asp Arg Asp Gly Ala Leu Ser Val Leu Asp Asp Arg
1               5                   10                  15

Ala Asp Ala Leu Gln Gln Gly Ala Ser Gln Phe Glu Thr Asn Ala Gly
            20                  25                  30

Lys Leu Lys Arg Lys Tyr Trp Trp
        35                  40

<210> SEQ ID NO 67
<211> LENGTH: 40
<212> TYPE: PRT
<213> ORGANISM: Aplysia sp.

<400> SEQUENCE: 67

Glu Lys Val Leu Asp Arg Asp Gln Lys Ile Ser Gln Leu Asp Asp Arg
1               5                   10                  15

Ala Glu Ala Leu Gln Ala Gly Ala Ser Gln Phe Glu Ala Ser Ala Gly
            20                  25                  30

Lys Leu Lys Arg Lys Tyr Trp Trp
        35                  40

<210> SEQ ID NO 68
<211> LENGTH: 40
<212> TYPE: PRT
<213> ORGANISM: Teuthoida sp.

<400> SEQUENCE: 68

Asp Lys Val Leu Glu Arg Asp Ser Lys Ile Ser Glu Leu Asp Asp Arg
1               5                   10                  15

Ala Asp Ala Leu Gln Ala Gly Ala Ser Gln Phe Glu Ala Ser Ala Gly
            20                  25                  30

Lys Leu Lys Arg Lys Phe Trp Trp
        35                  40

<210> SEQ ID NO 69
<211> LENGTH: 40
<212> TYPE: PRT
<213> ORGANISM: Caenorhabditis elegans

```
<400> SEQUENCE: 69

Asn Lys Val Met Glu Arg Asp Val Gln Leu Asn Ser Leu Asp His Arg
 1               5                  10                  15

Ala Glu Val Leu Gln Asn Gly Ala Ser Gln Phe Gln Gln Ser Ser Arg
             20                  25                  30

Glu Leu Lys Arg Gln Tyr Trp Trp
         35                  40

<210> SEQ ID NO 70
<211> LENGTH: 40
<212> TYPE: PRT
<213> ORGANISM: Drosophila sp.

<400> SEQUENCE: 70

Glu Lys Val Leu Glu Arg Asp Gln Lys Leu Ser Glu Leu Gly Glu Arg
 1               5                  10                  15

Ala Asp Gln Leu Glu Gly Gly Ala Ser Gln Ser Glu Gln Gln Ala Gly
             20                  25                  30

Lys Leu Lys Arg Lys Gln Trp Trp
         35                  40

<210> SEQ ID NO 71
<211> LENGTH: 40
<212> TYPE: PRT
<213> ORGANISM: Drosophila sp.

<400> SEQUENCE: 71

Glu Lys Val Leu Glu Arg Asp Ser Lys Leu Ser Glu Leu Asp Asp Arg
 1               5                  10                  15

Ala Asp Ala Leu Gln Gln Gly Ala Ser Gln Phe Glu Gln Gln Ala Gly
             20                  25                  30

Lys Leu Lys Arg Lys Phe Trp Leu
         35                  40

<210> SEQ ID NO 72
<211> LENGTH: 39
<212> TYPE: PRT
<213> ORGANISM: Hirudinida sp.

<400> SEQUENCE: 72

Asp Lys Val Leu Glu Lys Asp Gln Lys Leu Ala Glu Leu Asp Arg Ala
 1               5                  10                  15

Asp Ala Leu Gln Ala Gly Ala Ser Gln Phe Glu Ala Ser Ala Gly Lys
             20                  25                  30

Leu Lys Arg Lys Phe Trp Trp
         35

<210> SEQ ID NO 73
<211> LENGTH: 18
<212> TYPE: PRT
<213> ORGANISM: Homo sapiens

<400> SEQUENCE: 73

Glu Arg Ala Val Ser Asp Thr Lys Lys Ala Val Lys Tyr Gln Ser Lys
 1               5                  10                  15

Ala Arg
```

<210> SEQ ID NO 74
<211> LENGTH: 18
<212> TYPE: PRT
<213> ORGANISM: Bos taurus

<400> SEQUENCE: 74

Glu Arg Ala Val Ser Asp Thr Lys Lys Ala Val Lys Tyr Gln Ser Lys
1               5                   10                  15

Ala Arg

<210> SEQ ID NO 75
<211> LENGTH: 18
<212> TYPE: PRT
<213> ORGANISM: Rattus sp.

<400> SEQUENCE: 75

Glu His Ala Lys Glu Thr Lys Lys Ala Ile Lys Tyr Gln Ser Lys
1               5                   10                  15

Ala Arg

<210> SEQ ID NO 76
<211> LENGTH: 18
<212> TYPE: PRT
<213> ORGANISM: Rattus sp.

<400> SEQUENCE: 76

Glu Lys Ala Arg Asp Glu Thr Arg Lys Ala Met Lys Tyr Gln Gly Gly
1               5                   10                  15

Ala Arg

<210> SEQ ID NO 77
<211> LENGTH: 18
<212> TYPE: PRT
<213> ORGANISM: Rattus sp.

<400> SEQUENCE: 77

Glu Arg Gly Gln Glu His Val Lys Ile Ala Leu Glu Asn Gln Lys Lys
1               5                   10                  15

Ala Arg

<210> SEQ ID NO 78
<211> LENGTH: 18
<212> TYPE: PRT
<213> ORGANISM: Gallus gallus

<400> SEQUENCE: 78

Val Pro Glu Val Phe Val Thr Lys Ser Ala Val Met Tyr Gln Cys Lys
1               5                   10                  15

Ser Arg

<210> SEQ ID NO 79
<211> LENGTH: 18
<212> TYPE: PRT
<213> ORGANISM: Strongylocentrotus purpuratus

<400> SEQUENCE: 79

Val Arg Arg Gln Asn Asp Thr Lys Lys Ala Val Lys Tyr Gln Ser Lys
1               5                   10                  15

Ala Arg

```
<210> SEQ ID NO 80
<211> LENGTH: 18
<212> TYPE: PRT
<213> ORGANISM: Aplysia sp.

<400> SEQUENCE: 80

Glu Thr Ala Lys Met Asp Thr Lys Lys Ala Val Lys Tyr Gln Ser Lys
1               5                   10                  15

Ala Arg

<210> SEQ ID NO 81
<211> LENGTH: 18
<212> TYPE: PRT
<213> ORGANISM: Teuthoida sp.

<400> SEQUENCE: 81

Glu Thr Ala Lys Val Asp Thr Lys Lys Ala Val Lys Tyr Gln Ser Lys
1               5                   10                  15

Ala Arg

<210> SEQ ID NO 82
<211> LENGTH: 18
<212> TYPE: PRT
<213> ORGANISM: Drosophila sp.

<400> SEQUENCE: 82

Gln Thr Ala Thr Gln Asp Thr Lys Lys Ala Leu Lys Tyr Gln Ser Lys
1               5                   10                  15

Ala Arg

<210> SEQ ID NO 83
<211> LENGTH: 18
<212> TYPE: PRT
<213> ORGANISM: Hirudinida sp.

<400> SEQUENCE: 83

Glu Thr Ala Ala Ala Asp Thr Lys Lys Ala Met Lys Tyr Gln Ser Ala
1               5                   10                  15

Ala Arg

<210> SEQ ID NO 84
<211> LENGTH: 5
<212> TYPE: PRT
<213> ORGANISM: Artificial Sequence
<220> FEATURE:
<223> OTHER INFORMATION: synthetic construct

<400> SEQUENCE: 84

Gly Gly Gly Gly Ser
1               5

<210> SEQ ID NO 85
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: 1
<223> OTHER INFORMATION: Xaa=fluorescein-modified lysine
<220> FEATURE:
<221> NAME/KEY: MOD_RES
<222> LOCATION: 20
<223> OTHER INFORMATION: Xaa=tetramethylrhodamine-modified lysine
```

```
<220> FEATURE:
<221> NAME/KEY: AMIDATION
<222> LOCATION: (0)...(0)
<223> OTHER INFORMATION: at the C-terminal

<400> SEQUENCE: 85

Xaa Asp Asn Lys Thr Arg Ile Asp Glu Ala Asn Gln Arg Ala Thr Lys
 1               5                  10                  15

Met Leu Xaa

<210> SEQ ID NO 86
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: 1
<223> OTHER INFORMATION: Xaa=fluorescein-modified lysine

<400> SEQUENCE: 86

Xaa Asp Ser Asn Lys Thr Arg Ile Asp Glu Ala Asn Gln
 1               5                  10

<210> SEQ ID NO 87
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: 7
<223> OTHER INFORMATION: Xaa=tetramethylrhodamine-modified lysine
<220> FEATURE:
<221> NAME/KEY: AMIDATION
<222> LOCATION: (0)...(0)
<223> OTHER INFORMATION: at the C-terminal

<400> SEQUENCE: 87

Arg Ala Thr Lys Met Leu Xaa
 1               5

<210> SEQ ID NO 88
<211> LENGTH: 23
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: Xaa=fluorescein-modified lysine
<220> FEATURE:
<221> NAME/KEY: MOD_RES
<222> LOCATION: 23
<223> OTHER INFORMATION: Xaa=tetramethylrhodamine-modified lysine
<220> FEATURE:
<221> NAME/KEY: AMIDATION
<222> LOCATION: (0)...(0)
<223> OTHER INFORMATION: at the C-terminal

<400> SEQUENCE: 88

Xaa Asp Ser Asn Lys Thr Arg Ile Asp Glu Ala Asn Gln Arg Ala Thr
 1               5                  10                  15

Lys Met Leu Gly Ser Gly Xaa
             20
```

```
<210> SEQ ID NO 89
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: Xaa=fluorescein-modified lysine
<220> FEATURE:
<221> NAME/KEY: MOD_RES
<222> LOCATION: 21
<223> OTHER INFORMATION: Xaa=tetramethylrhodamine-modified lysine
<220> FEATURE:
<221> NAME/KEY: AMIDATION
<222> LOCATION: (0)...(0)
<223> OTHER INFORMATION: at the C-terminal

<400> SEQUENCE: 89

Xaa Ala Asp Ser Asn Lys Thr Arg Ile Asp Glu Ala Asn Gln Arg Ala
 1               5                  10                  15

Thr Lys Met Leu Xaa
            20

<210> SEQ ID NO 90
<211> LENGTH: 24
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: Xaa=fluorescein-modified lysine
<220> FEATURE:
<221> NAME/KEY: MOD_RES
<222> LOCATION: 24
<223> OTHER INFORMATION: Xaa=tetramethylrhodamine-modified lysine
<220> FEATURE:
<221> NAME/KEY: AMIDATION
<222> LOCATION: (0)...(0)
<223> OTHER INFORMATION: at the C-terminal

<400> SEQUENCE: 90

Xaa Ala Asp Ser Asn Lys Thr Arg Ile Asp Glu Ala Asn Gln Arg Ala
 1               5                  10                  15

Thr Lys Met Leu Gly Ser Gly Xaa
            20

<210> SEQ ID NO 91
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: Xaa=fluorescein-modified lysine
<220> FEATURE:
<221> NAME/KEY: MOD_RES
<222> LOCATION: 16
<223> OTHER INFORMATION: Xaa=tetramethylrhodamine-modified lysine
<220> FEATURE:
<221> NAME/KEY: AMIDATION
<222> LOCATION: (0)...(0)
<223> OTHER INFORMATION: at the C-terminal

<400> SEQUENCE: 91

Xaa Thr Arg Ile Asp Glu Ala Asn Gln Arg Ala Thr Lys Met Leu Xaa
 1               5                  10                  15
```

```
<210> SEQ ID NO 92
<211> LENGTH: 19
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: Xaa=fluorescein-modified lysine
<220> FEATURE:
<221> NAME/KEY: MOD_RES
<222> LOCATION: 19
<223> OTHER INFORMATION: Xaa=tetramethylrhodamine-modified lysine
<220> FEATURE:
<221> NAME/KEY: AMIDATION
<222> LOCATION: (0)...(0)
<223> OTHER INFORMATION: at the C-terminal

<400> SEQUENCE: 92

Xaa Thr Arg Ile Asp Glu Ala Asn Gln Arg Ala Thr Lys Met Leu Gly
 1               5                  10                  15

Ser Gly Xaa

<210> SEQ ID NO 93
<211> LENGTH: 22
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: Xaa=fluorescein-modified lysine
<220> FEATURE:
<221> NAME/KEY: MOD_RES
<222> LOCATION: 22
<223> OTHER INFORMATION: Xaa=tetramethylrhodamine-modified lysine
<220> FEATURE:
<221> NAME/KEY: AMIDATION
<222> LOCATION: (0)...(0)
<223> OTHER INFORMATION: at the C-terminal

<400> SEQUENCE: 93

Xaa Met Glu Lys Thr Arg Ile Asp Glu Ala Asn Gln Arg Ala Thr Lys
 1               5                  10                  15

Met Leu Gly Ser Gly Xaa
            20

<210> SEQ ID NO 94
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: Xaa-DABCYL modified lysine
<220> FEATURE:
<221> NAME/KEY: MOD_RES
<222> LOCATION: 16
<223> OTHER INFORMATION: Xaa=EDANS modified glutamate
<220> FEATURE:
<221> NAME/KEY: AMIDATION
<222> LOCATION: (0)...(0)
<223> OTHER INFORMATION: at the C-terminal

<400> SEQUENCE: 94

Xaa Thr Arg Ile Asp Glu Ala Asn Gln Arg Ala Thr Lys Met Leu Xaa
 1               5                  10                  15
```

```
<210> SEQ ID NO 95
<211> LENGTH: 19
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: Xaa=DABCYL modified lysine
<220> FEATURE:
<221> NAME/KEY: MOD_RES
<222> LOCATION: 19
<223> OTHER INFORMATION: Xaa=EDANS modified lysine
<220> FEATURE:
<221> NAME/KEY: AMIDATION
<222> LOCATION: (0)...(0)
<223> OTHER INFORMATION: at the C-terminal

<400> SEQUENCE: 95

Xaa Thr Arg Ile Asp Glu Ala Asn Gln Arg Ala Thr Lys Met Leu Gly
 1               5                  10                  15

Ser Gly Xaa

<210> SEQ ID NO 96
<211> LENGTH: 118
<212> TYPE: PRT
<213> ORGANISM: Homo sapiens

<400> SEQUENCE: 96

Met Ser Ala Pro Ala Gln Pro Pro Ala Glu Gly Thr Glu Gly Thr Ala
 1               5                  10                  15

Pro Gly Gly Gly Pro Pro Gly Pro Pro Pro Asn Met Thr Ser Asn Arg
                20                  25                  30

Arg Leu Gln Gln Thr Gln Ala Gln Val Glu Glu Val Val Asp Ile Ile
                35                  40                  45

Arg Val Asn Val Asp Lys Val Leu Glu Arg Asp Gln Lys Leu Ser Glu
            50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
                100                 105                 110

Val Ile Tyr Phe Phe Thr
                115
```

SUBSTRATES USEFUL FOR FRET PROTEASE ASSAYS FOR BOTULINUM SEROTYPE A/E TOXINS

This application is a divisional and claims priority pursuant to 35 U.S.C. §120 to U.S. patent application Ser. No. 09/942,024, filed Aug. 28, 2001 now U.S. Pat. No. 7,208,285, which is hereby incorporated by reference in its entirety.

BACKGROUND OF THE INVENTION

1. Field of the Invention

The present invention relates generally to fluorescence resonance energy transfer and protease assays, for example, assays for protease activity of clostridial toxins such botulinum toxins and tetanus toxins, and more specifically, to intramolecularly quenched substrates and methods for assaying for clostridial toxin protease activity.

2. Background Information

The neuroparalytic syndrome of tetanus and the rare but potentially fatal disease, botulism, are caused by neurotoxins produced by bacteria of the genus *Clostridium*. These clostridial neurotoxins are highly potent and specific poisons of neural cells, with the human lethal dose of the botulinum toxins on the order of micrograms. Thus, the presence of even minute levels of botulinum toxins in foodstuffs represents a public health hazard that must be avoided through rigorous testing.

However, in spite of their potentially deleterious effects, low controlled doses of botulinum neurotoxins have been successfully used as therapeutics. These toxins have been used in the therapeutic management of a variety of focal and segmental dystonias, of strabismus and other conditions in which a reversible depression of a cholinergic nerve terminal activity is desired. Established therapeutic uses of botulinum neurotoxins in humans include, for example, blepharospasm, hemifacial spasm, laringeal dysphonia, focal hyperhidrosis, hypersalivation, oromandibular dystonia, cervical dystonia, torticollis, strabismus, limbs dystonia, occupational cramps and myokymia (Rossetto et al, *Toxicon* 39:27-41 (2001)). Intramuscular injection of spastic tissue with small quantities of BoNT/A, for example, has been used effectively to treat spasticity due to brain injury, spinal cord injury, stroke, multiple sclerosis and cerebral palsy. Additional possible clinical uses of clostridial neurotoxins currently are being investigated.

Given the potential danger associated with small quantities of botulinum toxins in foodstuffs and the need to prepare accurate pharmaceutical formulations, assays for botulinum neurotoxins presently are employed in both the food and pharmaceutical industry. The food industry requires assays for the botulinum neurotoxins to validate new food packaging methods and to ensure food safety. The growing clinical use of the botulinum toxins necessitates accurate assays for botulinum neurotoxin activity for product formulation as well as quality control. In both industries, a mouse lethality test currently is used to assay for botulinum neurotoxin activity. Unfortunately, this assay suffers from several drawbacks: cost due to the large numbers of laboratory animals required; lack of specificity; and the potential for inaccuracy unless large animal groups are used.

Thus, there is a need for new materials and methods for assaying for clostridial toxin activity. The present invention satisfies this need and provides related advantages as well.

SUMMARY OF THE INVENTION

The present invention provides clostridial toxin substrates useful in assaying for the protease activity of any clostridial toxin, including botulinum toxins of all serotypes as well as tetanus toxins. A clostridial toxin substrate of the invention contains a donor fluorophore; an acceptor having an absorbance spectrum overlapping the emission spectrum of the donor fluorophore; and a clostridial toxin recognition sequence that includes a cleavage site, where the cleavage site intervenes between the donor fluorophore and the acceptor and where, under the appropriate conditions, resonance energy transfer is exhibited between the donor fluorophore and the acceptor. Such a clostridial toxin substrate can include, for example, a botulinum toxin recognition sequence. In one embodiment, a clostridial toxin substrate of the invention includes a botulinum toxin recognition sequence which is not a botulinum toxin serotype B (BoNT/B) recognition sequence.

The invention also provides a botulinum serotype NE (BoNT/A/E) substrate containing (a) a donor fluorophore; (b) an acceptor having an absorbance spectrum overlapping the emission spectrum of the donor fluorophore; and (c) a BoNT A or BoNT/E recognition sequence containing a cleavage site, where the cleavage site intervenes between the donor fluorophore and the acceptor and where, under the appropriate conditions, resonance energy transfer is exhibited between the donor fluorophore and the acceptor. Such a botulinum serotype NE substrate also can be susceptible to cleavage by both the BoNT/A and BoNT/E toxins.

The invention further provides, for example, a botulinum toxin serotype A (BoNT/A) substrate containing a donor fluorophore; an acceptor having an absorbance spectrum overlapping the emission spectrum of the donor fluorophore; and a BoNT/A recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/A substrate of the invention can include, for example, at least six consecutive residues of SNAP-25, where the six consecutive residues include Gln-Arg, or a peptidomimetic thereof. In these and other amino acid sequences provided herein, it is understood that the sequence is written in the direction from N-terminus to C-terminus. A BoNT/A substrate of the invention also can have, for example, at least six consecutive residues of human SNAP-25, where the six consecutive residues include $Gln_{197}$-$Arg_{198}$, or a peptidomimetic thereof. In one embodiment, a BoNT/A substrate of the invention includes the amino acid sequence Glu-Ala-Asn-Gln-Arg-Ala-Thr-Lys (SEQ ID NO: 1), or a peptidomimetic thereof. In another embodiment, a BoNT/A substrate of the invention includes residues 187 to 203 of human SNAP-25 (SEQ ID NO: 2), or a peptidomimetic thereof. A variety of donor fluorophores and acceptors are useful in a BoNT/A substrate of the invention, including but not limited to, fluorescein-tetramethylrhodamine; DABCYL-EDANS; and Alexa Fluor® 488-QSY 7®.

Further provided by the invention is a botulinum toxin serotype B (BoNT/B) substrate containing a donor fluorophore; an acceptor having an absorbance spectrum overlapping the emission spectrum of the donor fluorophore; and a BoNT/B recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/B substrate of the invention can contain, for example, at least six consecutive residues of VAMP, where the six consecutive residues include Gln-Phe, or a peptidomimetic thereof. For example, a BoNT/B substrate of the invention can contain at least six consecutive residues of human VAMP-2, the six consecutive residues including $Gln_{76}$-$Phe_{77}$, or a peptidomimetic thereof. In one embodiment, a BoNT/B substrate includes the amino acid sequence Gly-Ala-Ser-Gln-Phe-Glu-Thr-Ser (SEQ ID NO: 3), or a peptidomimetic thereof. In another embodiment, a BoNT/B substrate includes residues 55 to 94 of human VAMP-2 (SEQ ID NO: 4); residues 60 to 94 of human VAMP-2 (SEQ ID NO: 4); or residues 60 to 88 of human VAMP-2 (SEQ ID NO: 4), or a peptidomimetic of one of these sequences. It is understood that a variety of donor fluorophores and acceptors are useful in a BoNT/B substrate of the invention; such donor fluorophore-acceptor combinations include, but are not limited to, fluorescein-tetramethylrhodamine; DABCYL-EDANS; and Alexa Fluor® 488-QSY® 7.

The invention also provides a botulinum toxin serotype C1 (BoNT/C1) substrate containing a donor fluorophore; an acceptor having an absorbance spectrum overlapping the emission spectrum of the donor fluorophore; and a BoNT/C1 recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/C1 substrate of the invention can have, for example, at least six consecutive residues of syntaxin, the six consecutive residues including Lys-Ala, or a peptidomimetic thereof. For example, a BoNT/C1 substrate of the invention can have at least six consecutive residues of human syntaxin, the six consecutive residues including $Lys_{253}$-$Ala_{254}$, or a peptidomimetic thereof. In one embodiment, a BoNT/C1 substrate contains the amino acid sequence Asp-Thr-Lys-Lys-Ala-Val-Lys-Tyr (SEQ ID NO: 5), or a peptidomimetic thereof.

A BoNT/C1 substrate of the invention also can contain, for example, at least six consecutive residues of SNAP-25, where the six consecutive residues include Arg-Ala, or a peptidomimetic thereof. Such a BoNT/C1 substrate can have, for example, at least six consecutive residues of human SNAP-25, the six consecutive residues including $Arg_{198}$-$Ala_{199}$, or a peptidomimetic thereof. An exemplary BoNT/C1 substrate contains residues 93 to 202 of human SNAP-25 (SEQ ID NO: 2), or a peptidomimetic thereof. As for all the clostridial toxin substrates of the invention, a variety of donor fluorophore-acceptor combinations are useful in a BoNT/C1 substrate, including, for example, fluorescein-tetramethylrhodamine; DABCYL-EDANS; and Alexa Fluor® 488-QSY® 7.

The present invention further provides a botulinum toxin serotype D (BoNT/D) substrate containing a donor fluorophore; an acceptor having an absorbance spectrum overlapping the emission spectrum of the donor fluorophore; and a BoNT/D recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/D substrate of the invention can have, for example, at least six consecutive residues of VAMP, the six consecutive residues including Lys-Leu, or a peptidomimetic thereof. In one embodiment, a BoNT/D substrate contains at least six consecutive residues of human VAMP, the six consecutive residues including $Lys_{59}$-$Leu_{60}$, or a peptidomimetic thereof. In another embodiment, a BoNT/D substrate of the invention contains the amino acid sequence Arg-Asp-Gln-Lys-Leu-Ser-Glu-Leu (SEQ ID NO: 6), or a peptidomimetic thereof. In a further embodiment, a BoNT/D substrate of the invention includes residues 27 to 116 of rat VAMP-2 (SEQ ID NO: 7), or a peptidomimetic thereof. It is understood that a variety of donor fluorophore-acceptor combinations are useful in a BoNT/D substrate of the invention; such donor fluorophore-acceptor pairs include, but are not limited to, fluorescein-tetramethylrhodamine; DABCYL-EDANS; and Alexa Fluor® 488-QSY® 7.

The present invention additionally provides a botulinum toxin serotype E (BoNT/E) substrate containing a donor fluorophore; an acceptor having an absorbance spectrum overlapping the emission spectrum of the donor fluorophore; and a BoNT/E recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/E substrate can contain, for example, at least six consecutive residues of SNAP-25, the six consecutive residues including Arg-Ile, or a peptidomimetic thereof. Such a BoNT/E substrate can have, for example, at least six consecutive residues of human SNAP-25, the six consecutive residues including $Arg_{180}$-$Ile_{181}$, or a peptidomimetic thereof. In one embodiment, a BoNT/E substrate includes the amino acid sequence Gln-Ile-Asp-Arg-Ile-Met-Glu-Lys (SEQ ID NO: 8), or a peptidomimetic thereof. In another embodiment, a BoNT/E substrate includes residues 156 to 186 of human SNAP-25 (SEQ ID NO: 2), or a peptidomimetic thereof. A variety of donor fluorophore-acceptor combinations are useful in a BoNT/E substrate of the invention. These donor fluorophore-acceptor combinations include, without limitation, fluorescein-tetramethylrhodamine; DABCYL-EDANS; and Alexa Fluor® 488-QSY® 7.

Further provided by the invention is a botulinum toxin serotype F (BoNT/F) substrate containing a donor fluorophore; an acceptor having an absorbance spectrum overlapping the emission spectrum of the donor fluorophore; and a BoNT/F recognition sequence that includes a cleavage site, where the cleavage site intervenes between the donor fluorophore and the acceptor and where, under the appropriate conditions, resonance energy transfer is exhibited between the donor fluorophore and the acceptor. Such a BoNT/F substrate can have, for example, at least six consecutive residues of VAMP, the six consecutive residues including Gln-Lys, or a peptidomimetic thereof. In one embodiment, a BoNT/F substrate has at least six consecutive residues of human VAMP, the six consecutive residues including $Gln_{58}$-$Lys_{59}$, or a peptidomimetic thereof. In another embodiment, a BoNT/F substrate of the invention includes residues 27 to 116 of rat VAMP-2 (SEQ ID NO: 7), or a peptidomimetic thereof. In a further embodiment, a BoNT/F substrate includes the amino acid sequence Glu-Arg-Asp-Gln-Lys-Leu-Ser-Glu (SEQ ID NO: 9), or a peptidomimetic thereof. Those skilled in the art of fluorescence resonance energy transfer understand that a variety of donor fluorophore-acceptor combinations are useful in a BoNT/F substrate of the invention, including, as not limiting examples, fluorescein-tetramethylrhodamine; DABCYL-EDANS; and Alexa Fluor® 488-QSY® 7.

The present invention also provides a botulinum toxin serotype G (BoNT/G) substrate containing a donor fluorophore; an acceptor having an absorbance spectrum overlapping the emission spectrum of the donor fluorophore; and a BoNT/G recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/G substrate can have, for example, at least six consecutive residues of VAMP, the six consecutive residues including Ala-Ala, or a peptidomimetic thereof. Such a BoNT/G substrate can have, for example, at least six consecutive residues of human VAMP, the six consecutive residues including $Ala_{83}$-$Ala_{84}$, or a peptidomimetic thereof. In one embodiment, a BoNT/G substrate contains the amino acid sequence Glu-Thr-Ser-Ala-Ala-Lys-Leu-Lys (SEQ ID NO: 10), or a peptidomimetic thereof. As discussed above in regard to other clostridial toxin substrates, a variety of donor fluorophore-acceptor combinations are useful in a BoNT/G substrate of the invention. Such donor fluorophore-acceptor combinations include, for example, fluorescein-tetramethylrhodamine; DABCYL-EDANS; and Alexa Fluor® 488-QSY® 7.

Also provided by the invention is a tetanus toxin (TeNT) substrate containing a donor fluorophore; an acceptor having an absorbance spectrum overlapping the emission spectrum of the donor fluorophore; and a TeNT recognition sequence that includes a cleavage site, where the cleavage site intervenes between the donor fluorophore and the acceptor and where, under the appropriate conditions, resonance energy transfer is exhibited between the donor fluorophore and the acceptor.

A TeNT substrate of the invention can have, for example, at least six consecutive residues of VAMP, the six consecutive residues include Gln-Phe, or a peptidomimetic thereof. For example, such a TeNT substrate can have at least six consecutive residues of human VAMP-2, the six consecutive residues including $Gln_{76}$-$Phe_{77}$, or a peptidomimetic thereof. In one embodiment, a TeNT substrate contains the amino acid sequence Gly-Ala-Ser-Gln-Phe-Glu-Thr-Ser (SEQ ID NO: 11), or a peptidomimetic thereof. In another embodiment, the TeNT substrate contains residues 33 to 94 of human VAMP-2 (SEQ ID NO: 4); residues 25 to 93 of human VAMP-2 (SEQ ID NO: 4); or residues 27 to 116 of rat VAMP-2 (SEQ ID NO: 7), or a peptidomimetic of one of these sequences. A variety of donor fluorophore-acceptor combinations are useful in a TeNT substrate of the invention, including, without limitation, fluorescein-tetramethylrhodamine; DABCYL-EDANS; and Alexa Fluor® 488-QSY® 7.

In specific embodiments, the invention provides a BoNT/A, BoNT/B, BoNT/C1, BoNT/D, BoNT/E, BoNT/F, BoNT/G or TeNT substrate that is cleaved with an activity of at least 1 nanomoles/minute/milligram toxin. In other embodiments, a BoNT/A, BoNT/B, BoNT/C1, BoNT/D, BoNT/E, BoNT/F, BoNT/G or TeNT substrate of the invention is cleaved with an activity of at least 10 nanomoles/minute/milligram toxin. In further embodiments, a BoNT/A, BoNT/B, BoNT/C1, BoNT/D, BoNT/E, BoNT/F, BoNT/G or TeNT substrate of the invention is cleaved with an activity of at least 20 nanomoles/minute/milligram toxin. In yet other embodiments, a BoNT/A, BoNT/B, BoNT/C1, BoNT/D, BoNT/E, BoNT/F, BoNT/G or TeNT substrate of the invention is cleaved with an activity of at least 50, 100 or 150 nanomoles/minute/milligram toxin.

A variety of donor fluorophores and acceptors, including fluorescent and non-fluorescent acceptors, are useful in the clostridial toxin substrates of the invention. Donor fluorophores useful in the invention include, but are not limited to, fluorescein, Alexa Fluor® 488, DABCYL, and BODIPY. Acceptors useful in the invention include, but are not limited to, tetramethylrhodamine, EDANS and QSY® 7. Exemplary donor fluorophore-acceptor pairs useful in a clostridial toxin substrate of the invention include, without limitation, fluorescein-tetramethylrhodamine, Alexa Fluor® 488-tetramethylrhodamine, DABCYL-EDANS, fluorescein-QSY® 7, and Alexa Fluor® 488-QSY® 7.

Clostridial toxin substrates of the invention encompass peptides and peptidomimetics of a variety of lengths and in which the donor fluorophore and acceptor are separated by different numbers of residues. In particular embodiments, a clostridial toxin substrate of the invention is a peptide or peptidomimetic having at most 20 residues, at most 40 residues, at most 50 residues, or at most 100 residues. In other embodiments, the donor fluorophore and the acceptor are separated by at most six residues, at most eight residues, at most ten residues or at most fifteen residues.

Further provided by the invention is a method of determining clostridial toxin protease activity. The method includes the steps of (a) treating a sample, under conditions suitable for clostridial toxin protease activity, with a clostridial toxin substrate that contains a donor fluorophore, an acceptor having an absorbance spectrum overlapping the emission spectrum of the donor fluorophore, and a clostridial toxin recognition sequence containing a cleavage site, where the cleavage site intervenes between the donor fluorophore and the acceptor and where, under the appropriate conditions, resonance energy transfer is exhibited between the donor fluorophore and the acceptor; (b) exciting the donor fluorophore; and (c) determining resonance energy transfer of the treated substrate relative to a control substrate, where a difference in resonance energy transfer of the treated substrate as compared to the control substrate is indicative of clostridial toxin protease activity. A method of the invention can be practiced with a fluorescent or non-fluorescent acceptor.

A method of the invention can be used to assay the protease activity of any clostridial toxin. In one embodiment, a method of the invention relies on a BoNT/A substrate to determine BoNT/A protease activity. A BoNT/A substrate useful in a method of the invention can be any of the BoNT/A substrates disclosed herein, for example, a BoNT/A substrate containing at least six consecutive residues of SNAP-25, where the six consecutive residues include Gln-Arg. In another embodiment, a method of the invention relies on a BoNT/B substrate to determine BoNT/B protease activity. A BoNT/B substrate useful in a method of the invention can be any of the BoNT/B substrates disclosed herein, for example, a BoNT/B substrate containing at least six consecutive residues of VAMP, where the six consecutive residues include Gln-Phe. A method of the invention also can utilize a BoNT/C1 substrate to determine BoNT/C1 protease activity. A BoNT/C1 substrate useful in a method of the invention can be any of the BoNT/C1 substrates disclosed herein, for example, a BoNT/C1 substrate containing at least six consecutive residues of syntaxin, where the six consecutive residues include Lys-Ala, or containing at least six consecutive residues of SNAP-25, where the six consecutive residues include Arg-Ala.

In another embodiment, a method of the invention relies on a BoNT/D substrate to determine BoNT/D protease activity. A BoNT/D substrate useful in a method of the invention can be any of the BoNT/D substrates disclosed herein, for example, a BoNT/D substrate containing at least six consecutive residues of VAMP, where the six consecutive residues include Lys-Leu. In a further embodiment, a method of the invention relies on a BoNT/E substrate to determine BoNT/E protease activity. A BoNT/E substrate useful in a method of the invention can be any of the BoNT/E substrates disclosed herein, for example, a BoNT/E substrate containing at least six consecutive residues of SNAP-25, where the six consecutive residues include Arg-Ile. In yet a further embodiment, a method of the invention relies on a BoNT/F substrate to determine BoNT/F protease activity. A BoNT/F substrate useful in a method of the invention can be any of the BoNT/F substrates disclosed herein, for example, a BoNT/F substrate containing at least six consecutive residues of VAMP, where the six consecutive residues include Gln-Lys.

A method of the invention also can utilize a BoNT/G substrate to determine BoNT/G protease activity. A BoNT/G substrate useful in a method of the invention can be any of the BoNT/G substrates disclosed herein, for example, a BoNT/G substrate containing at least six consecutive residues of VAMP, where the six consecutive residues include Ala-Ala. A method of the invention also can be useful to determine TeNT protease activity and, in this case, relies on a TeNT substrate. Any of the TeNT substrates disclosed herein can be useful in a method of the invention, for example, a TeNT substrate containing at least six consecutive residues of VAMP, where the six consecutive residues include Gln-Phe.

A variety of samples that potentially contain an active clostridial toxin, or light chain or fragment thereof, are useful in the methods of the invention. Such samples include, but are not limited to, crude cell lysates; isolated clostridial toxins; isolated clostridial toxin light chains; formulated clostridial toxin products, for example, BOTOX®; and foodstuffs, including raw, cooked, partially cooked or processed foods or beverages.

In a method of the invention, resonance energy transfer can be determined by a variety of means. In one embodiment, the step of determining resonance energy transfer includes detecting donor fluorescence intensity of the treated substrate, where increased donor fluorescence intensity of the treated substrate as compared to the control substrate is indicative of clostridial toxin protease activity. In another embodiment, the step of determining resonance energy transfer includes detecting acceptor fluorescence intensity of the treated substrate, where decreased acceptor fluorescence intensity of the treated substrate as compared to the control substrate is indicative of clostridial toxin protease activity. In a further embodiment, the step of determining resonance energy transfer includes detecting an acceptor emission maximum and a donor fluorophore emission maximum of the treated substrate, where a shift in emission maxima from near the acceptor emission maximum to near the donor fluorophore emission maximum is indicative of clostridial toxin protease activity. In an additional embodiment, the step of determining resonance energy transfer includes detecting the ratio of fluorescence amplitudes near an acceptor emission maximum to the fluorescence amplitudes near a donor fluorophore emission maximum, where a decreased ratio of the treated sample as compared to a control sample is indicative of clostridial toxin protease activity. In yet a further embodiment, the step of determining resonance energy transfer is practiced by detecting the excited state lifetime of the donor fluorophore, where an increased donor fluorophore excited state lifetime of the treated substrate as compared to the control substrate is indicative of clostridial toxin protease activity.

As discussed further below, a variety of conditions suitable for clostridial toxin protease activity are useful in a method of the invention. In one embodiment, the conditions suitable for clostridial toxin protease activity are selected such that the assay is linear. In another embodiment, conditions suitable for clostridial toxin protease activity are selected such that at least 90% of the clostridial toxin substrate is cleaved. In a further embodiments, conditions suitable for clostridial toxin protease activity are selected such that at most 5%, at most 10%, at most 15%, at most 20% or at most 25% of the clostridial toxin substrate is cleaved.

BRIEF DESCRIPTION OF THE DRAWINGS

FIG. 5 shows an alignment of various SNAP-25 proteins and their BoNT/E, BoNT/A and BoNT/C1 cleavage sites. Human SNAP-25 (SEQ ID NO: 2; GenBank accession g4507099; see, also, related human SNAP-25 sequence g2135800); mouse SNAP-25 (SEQ ID NO: 12; GenBank accession G6755588); Drosophila SNAP-25 (SEQ ID NO: 13; GenBank accession g548941); goldfish SNAP-25 (SEQ ID NO: 14; GenBank accession g2133923); sea urchin SNAP-25 (SEQ ID NO: 15; GenBank accession g2707818) and chicken SNAP-25 (SEQ ID NO: 16; GenBank accession g481202) are depicted.

FIG. 6 shows an alignment of various VAMP proteins and their BoNT/F, BoNT/D, BoNT/B, TeNT and BoNT/G cleavage sites. Human VAMP-1 (SEQ ID NO: 96; GenBank accession g135093); human VAMP-2 (SEQ ID NO: 4; GenBank accession g135094); mouse VAMP-2 (SEQ ID NO: 17; GenBank accession g2501081); bovine VAMP (SEQ ID NO: 15; GenBank accession g89782); frog VAMP (SEQ ID NO: 19; GenBank accession g6094391); and sea urchin VAMP (SEQ ID NO: 20; GenBank accession g5031415) are depicted.

FIG. 7 shows an alignment of various syntaxin proteins and their BoNT/C1 cleavage sites. Human syntaxin 1A (SEQ ID NO: 21; GenBank accession g15079184), human syntaxin 1B2 (SEQ ID NO: 22; GenBank accession g15072437), mouse syntaxin 1A (SEQ ID NO: 23; GenBank accession g15011853), Drosophila syntaxin 1A (SEQ ID NO: 24; GenBank accession g2501095); C. elegans syntaxin A (SEQ ID NO: 25; GenBank accession g7511662) and sea urchin syntaxin (SEQ ID NO: 26; GenBank accession g13310402) are depicted.

DETAILED DESCRIPTION OF THE INVENTION

Figure 1:
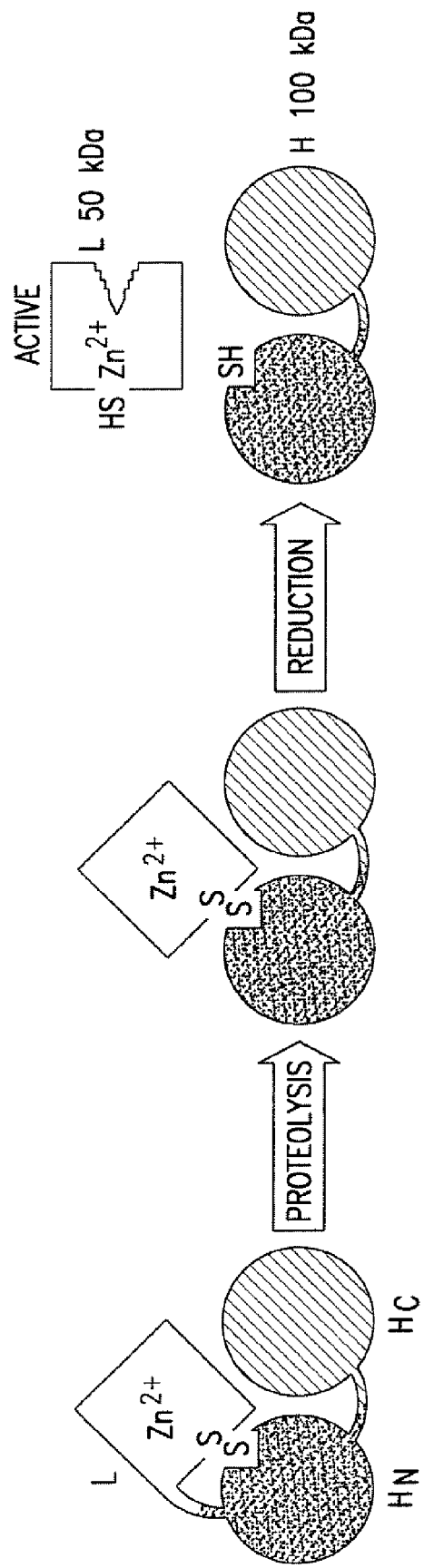
FIG. 1 shows a schematic of the deduced structure and postulated mechanism of activation of clostridial neurotoxins. Toxins can be produced as an inactive single polypeptide chain of 150 kDa, composed of three 50 kDa domains connected by loops. Selective proteolytic cleavage activates the toxins by generating two disulfide-linked chains: the L chain of 50 kDa and the H chain of 100 kDa, which is made up of two domains denoted $H_N$ and $H_C$. The three domains play distinct roles: the C-terminal domain of the heavy chain ($H_C$) functions in cell binding while the N-terminal domain of the heavy chain ($H_N$) permits translocation from endosome to cell cytoplasm. Following reduction of the disulfide linkage inside the cell, the zinc-endopeptidase activity of the L chain is liberated.

The invention provides clostridial toxin substrates useful in determining the presence or absence of a clostridial toxin or for determining the protease activity of any clostridial toxin, including botulinum toxins of all serotypes as well as tetanus toxins. The clostridial toxin substrates of the invention are valuable, in part, because they can be utilized in rapid and simple homogeneous screening assays that do not require separation of cleaved product from uncleaved substrate and do not rely on toxicity to animals. Furthermore, the clostridial toxin substrates of the invention can be used, for example, to analyze crude and bulk samples as well as highly purified dichain toxins or isolated clostridial toxin light chains.

As discussed below, fluorescence resonance energy transfer (FRET) is a distance-dependent interaction between the electronic excited states of two molecules in which excitation is transferred from a donor fluorophore to an acceptor without emission of a photon. The process of energy transfer results in a reduction (quenching) of fluorescence intensity and excited state lifetime of the donor fluorophore and, where the acceptor is a fluorophore, can produce an increase in the emission intensity of the acceptor. Upon cleavage of a clostridial toxin substrate of the invention, resonance energy transfer is reduced and can be detected, for example, by increased donor fluorescence emission, decreased acceptor fluorescence emission, or by a shift in the emission maxima from near the acceptor emission maxima to near the donor emission maxima. If desired, the amount of clostridial toxin in a sample can be calculated as a function of the difference in the degree of FRET using the appropriate standards.

A clostridial toxin substrate of the invention contains a donor fluorophore; an acceptor having an absorbance spectrum overlapping the emission spectrum of the donor fluorophore; and a clostridial toxin recognition sequence that includes a cleavage site, where the cleavage site intervenes between the donor fluorophore and the acceptor and where, under the appropriate conditions, resonance energy transfer is exhibited between the donor fluorophore and the acceptor. A clostridial toxin substrate of the invention can include, for example, a botulinum toxin recognition sequence. In one embodiment, a clostridial toxin substrate of the invention includes a botulinum toxin recognition sequence which is not a botulinum toxin serotype B (BoNT/B) recognition sequence.

In specific embodiments, the invention provides a BoNT/A, BoNT/B, BoNT/C1, BoNT/D, BoNT/E, BoNT/F, BoNT/G or TeNT substrate that is cleaved with an activity of at least 1 nanomole/minute/milligram toxin. In other embodiments, a BoNT/A, BoNT/B, BoNT/C1, BoNT/D, BoNT/E, BoNT/F, BoNT/G or TeNT substrate of the invention is cleaved with an activity of at least 10 nanomoles/minute/milligram toxin. In further embodiments, a BoNT/A, BoNT/B, BoNT/C1, BoNT/D, BoNT/E, BoNT/F, BoNT/G or TeNT substrate of the invention is cleaved with an activity of at least 20 nanomoles/minute/milligram toxin. In yet other embodiments, a BoNT/A, BoNT/B, BoNT/C1, BoNT/D, BoNT/E, BoNT/F, BoNT/G or TeNT substrate of the invention is cleaved with an activity of at least 50, 100 or 150 nanomoles/minute/milligram toxin. It is understood that such activity is measured under standard kinetic conditions.

A variety of donor fluorophores and acceptors, including fluorescent and non-fluorescent acceptors, are useful in the clostridial toxin substrates of the invention. Donor fluorophores useful in the invention include, but are not limited to, fluorescein, Alexa Fluor® 488, DABCYL, and BODIPY. Acceptors useful in the invention include, but are not limited to, tetramethylrhodamine, EDANS and QSY® 7. Exemplary donor fluorophore-acceptor pairs useful in a clostridial toxin substrate of the invention include, without limitation, fluorescein-tetramethylrhodamine, Alexa Fluor® 488-tetramethylrhodamine, DABCYL-EDANS, fluorescein-QSY® 7, and Alexa Fluor® 488-QSY® 7.

Clostridial toxin substrates of the invention encompass proteins, peptides and peptidomimetics of a variety of lengths and in which the donor fluorophore and acceptor are separated by different numbers of residues. In particular embodiments, a clostridial toxin substrate of the invention is has at most 20 residues, at most 40 residues, at most 50 residues, at most 100 residues, at most 150 residues, at most 200 residues, at most 250 residues, at most 300 residues, at most 350 residues or at most 400 residues. In other embodiments, the donor fluorophore and the acceptor are separated by at most six residues, at most eight residues, at most ten residues, at most twelve residues, at most fifteen residues, at most twenty residues, at most twenty-five residues, at most thirty residues, at most thirty-five residues or at most forty residues.

Tetanus and botulinum neurotoxins are produced by Clostridia and cause the neuroparalytic syndromes of tetanus and botulism. While tetanus neurotoxin acts mainly at the CNS synapse, botulinum neurotoxins act peripherally. Clostridial neurotoxins share a similar mechanism of cell intoxication, blocking the release of neurotransmitters. In these toxins, which are composed of two disulfide-linked polypeptide chains, the larger subunit is responsible for neurospecific binding and translocation of the smaller subunit into the cytoplasm. Upon translocation and reduction in neurons, the smaller chain displays peptidase activity specific for protein components involved in neuroexocytosis in the neuronal cytosol. The SNARE protein targets of clostridial toxins are common to exocytosis in a variety of non-neuronal types; in these cells, as in neurons, light chain peptidase activity inhibits exocytosis.

Tetanus neurotoxin and botulinum neurotoxins B, D, F, and G recognize specifically VAMP (synaptobrevin), an integral protein of the synaptic vesicle membrane which is cleaved at distinct bonds depending on the neurotoxin. Botulinum A and E neurotoxins recognize and cleave specifically SNAP-25, a protein of the presynaptic membrane, at two different sites in the carboxy-terminal portion of the protein. Botulinum neurotoxin C cleaves syntaxin, a protein of the nerve plasmalemma, in addition to SNAP-25. The three protein targets of the Clostridial neurotoxins are conserved from yeast to humans although cleavage sites and toxin susceptibility are not necessarily conserved (see below; see, also, Humeau et al., *Biochimie* 82:427-446 (2000); Niemann et al., *Trends in Cell Biol.* 4:179-185 (1994); and Pellizzari et al., *Phil. Trans. R. Soc. London* 354:259-268 (1999)).

Naturally occurring tetanus and botulinum neurotoxins are produced as inactive polypeptide chains of 150 kDa without a leader sequence. These toxins may be cleaved by bacterial or tissue proteinases at an exposed protease-sensitive loop, generating active di-chain toxin. Naturally occurring clostridial toxins contain a single interchain disulfide bond bridging the heavy chain (H, 100 kDa) and light chain (L, 50 kDa); such a bridge is important for neurotoxicity of toxin added extracellularly (Montecucco and Schiavo, *Quarterly Rev. Biophysics* 28:423-472 (1995)).

Figure 2:
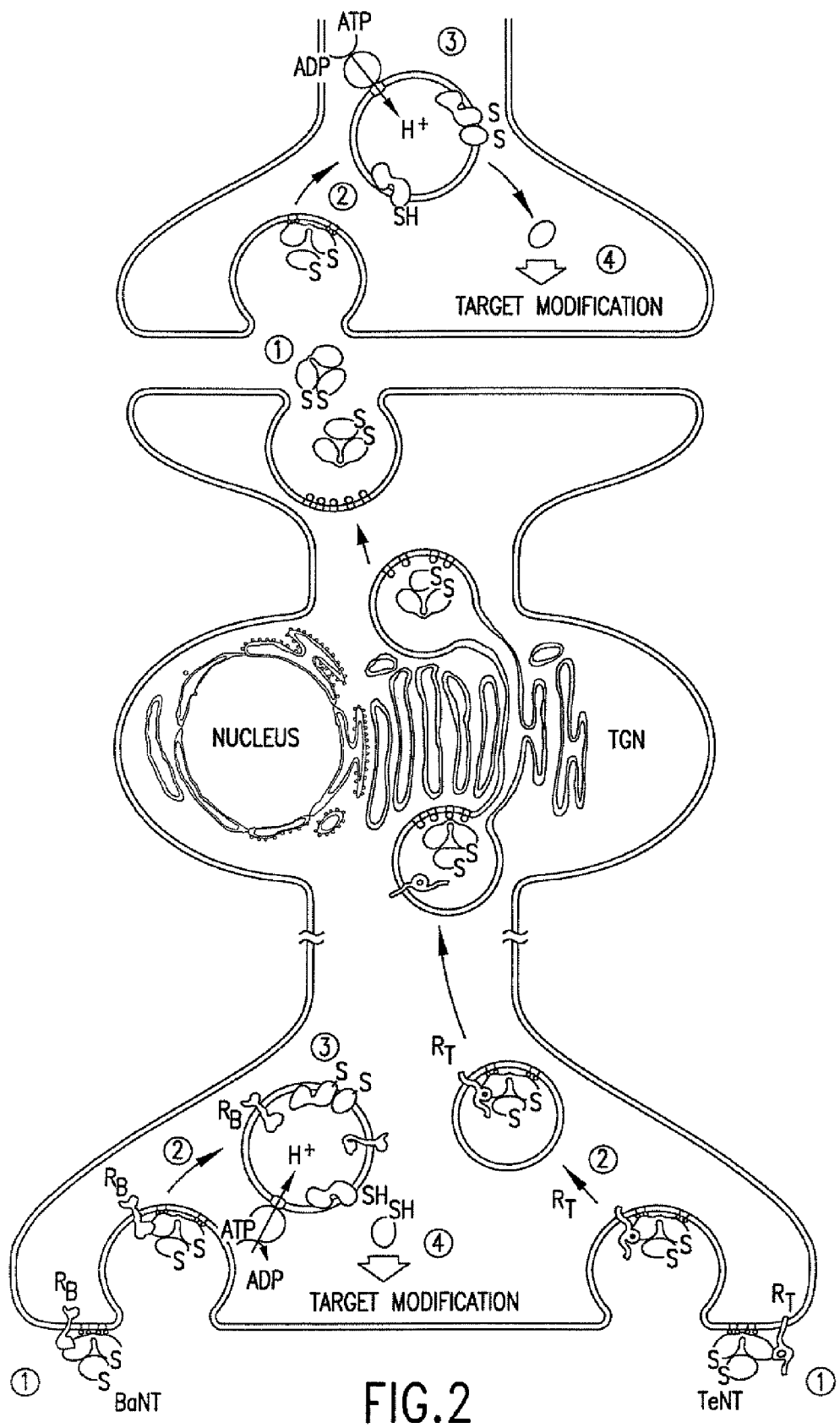
FIG. 2 shows a schematic of the four steps required for tetanus and botulinum toxin activity in central and peripheral neurons.

The clostridial toxins appear to be folded into three distinct 50 kDa domains, as shown in FIG. 1, with each domain having a distinct functional role. AS illustrated in FIG. 2, the cell intoxication mechanism of the clostridial toxins consists of four distinct steps: (1) binding; (2) internalization; (3) membrane translocation; and (4) enzymatic target modification. The carboxy-terminal part of the heavy chain ($H_C$) functions in neurospecific binding, while the amino-terminal portion of the H chain ($H_N$) functions in membrane translocation. The L chain is responsible for the intracellular catalytic activity (Montecucco and Schiavo, supra, 1995).

The amino acid sequence of eight human clostridial neurotoxins has been derived from the corresponding gene (Neimann, "Molecular Biology of Clostridial Neurotoxins" in *Sourcebook of Bacterial Protein Toxins* Alouf and Freer (Eds.) pp. 303-348 London: Academic Press 1991). The L chains and H chains are composed of roughly 439 and 843 residues, respectively. Homologous segments are separated by regions of little or no similarity. The most well conserved regions of the L chains are the amino-terminal portion (100 residues) and central region (corresponding to residues 216 to 244 of TeNT), as well as the two cysteines forming the interchain disulfide bond. The 216 to 244 region contains a His-Glu-X-X-His binding motif characteristic of zinc-endopeptidases.

The heavy chains are less well conserved than the light chains, and the carboxy-terminal part of $H_C$ (corresponding to residues 1140 to 1315 of TeNT) is the most variable. This is consistent with the involvement of the $H_C$ domain in binding to nerve terminals and the fact that the different neurotoxins appear to bind different receptors. Not surprisingly, many serotype specific antibodies recognize heavy chain determinants.

Figure 5:
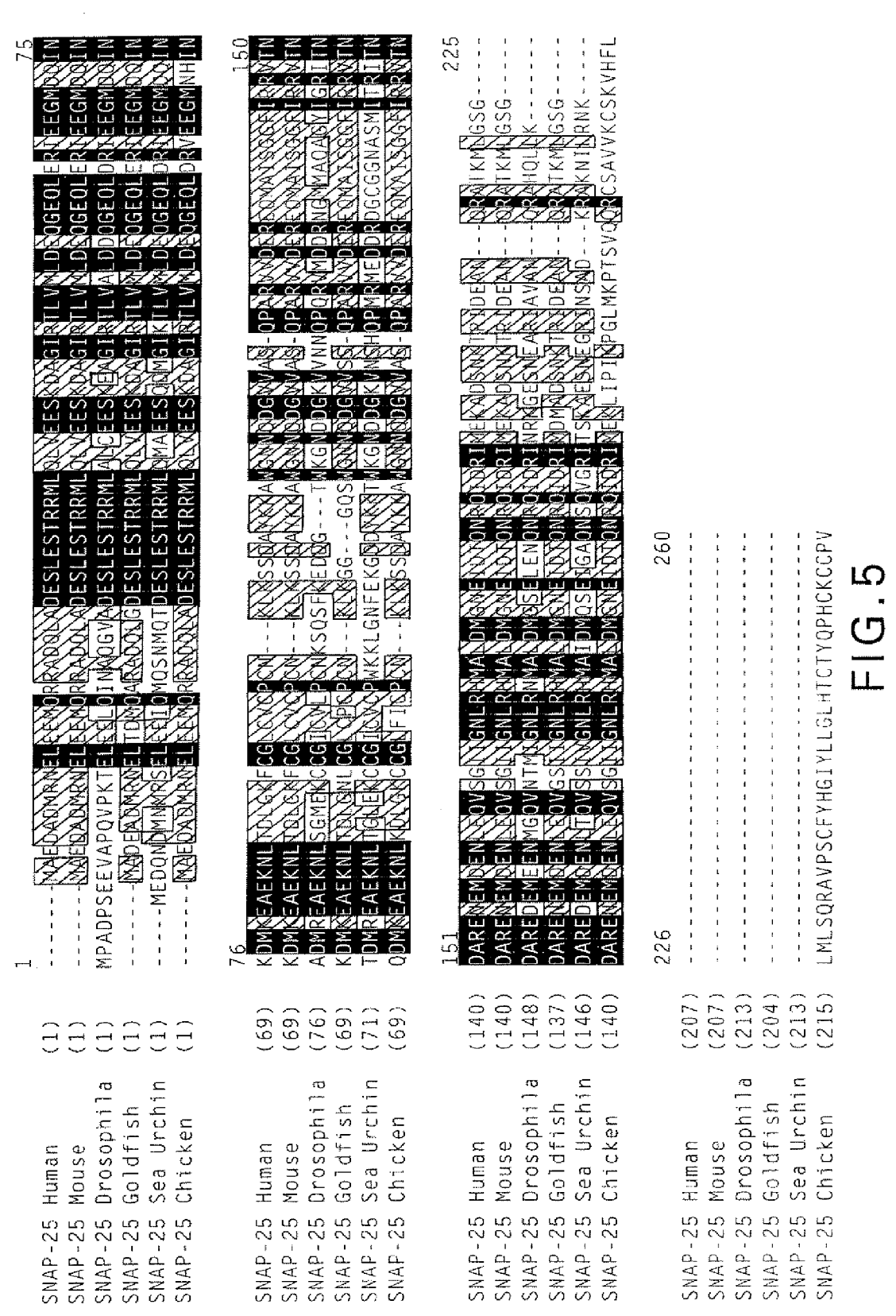
Figure 7:
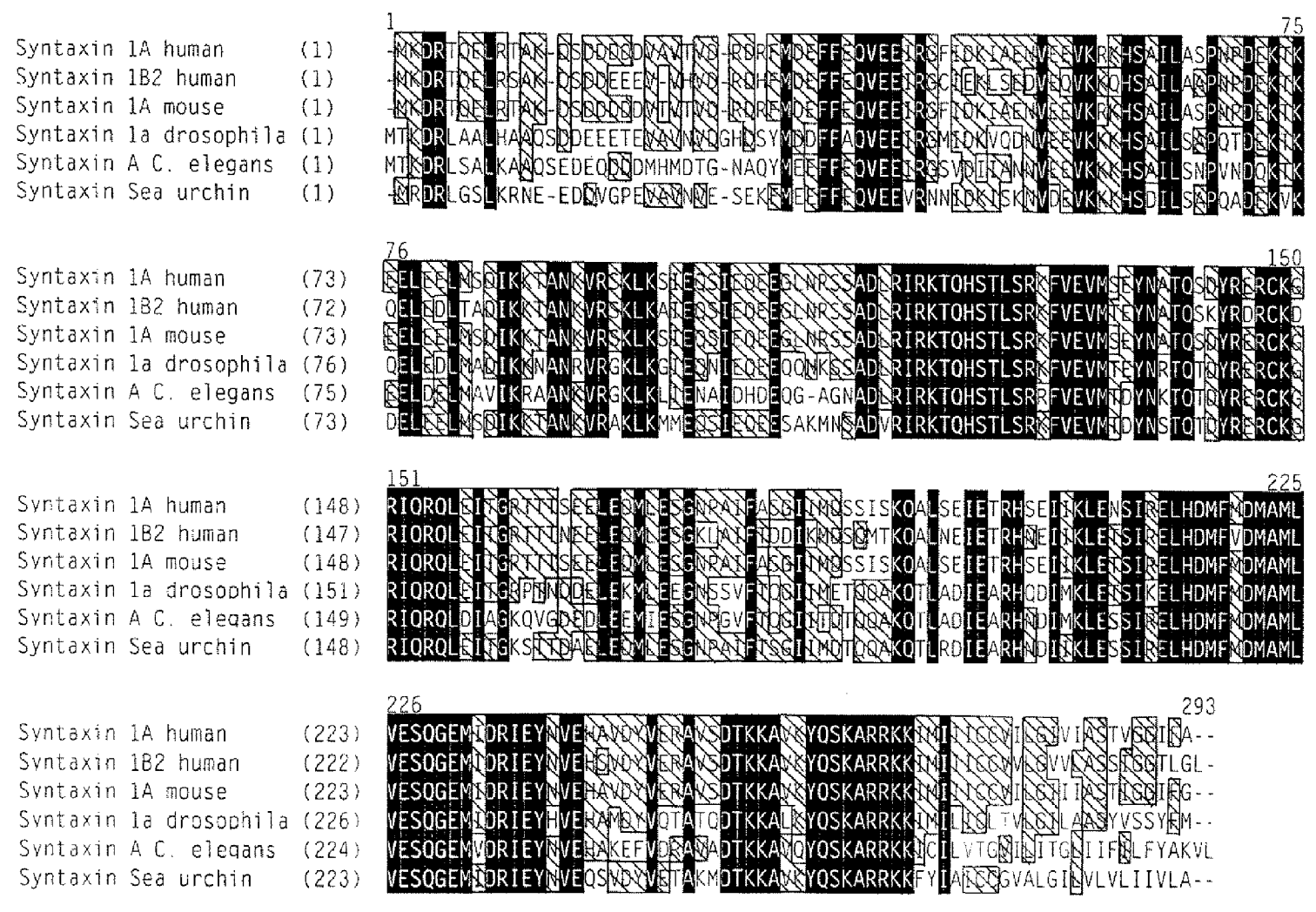

Comparison of the nucleotide and amino acid sequences of clostridial toxins indicates that they derive from a common ancestral gene. Spreading of these genes may have been facilitated by the fact that the clostridial neurotoxin genes are located on mobile genetic elements. As discussed further below, sequence variants of the seven botulinum toxins are known in the art. See, for example, FIGS. 5 to 7 and Humeau et al., supra, 2000.

As discussed above, natural targets of the clostridial neurotoxins include VAMP, SNAP-25, and syntaxin. VAMP is bound to the synaptic vesicle membrane, whereas SNAP-25 and syntaxin are bound to the target membrane (see FIG. 3). BoNT/A and BoNT/E cleave SNAP-25 in the carboxy-terminal region, releasing nine or twenty-six amino acid residues, respectively, and BoNT/C1 also cleaves SNAP-25 near the carboxy-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. Thus, the action of BoNT/B, BoNT/C1, BoNT/D, BoNT/F, BoNT/G and TeNT results in release of a large portion of the cytosolic domain of VAMP and syntaxin, while only a small portion of SNAP-25 is released by proteolysis of BoNT/A, BoNT/C1 or BoNT/E (Montecucco and Schiavo, supra, 1995).

Figure 3:
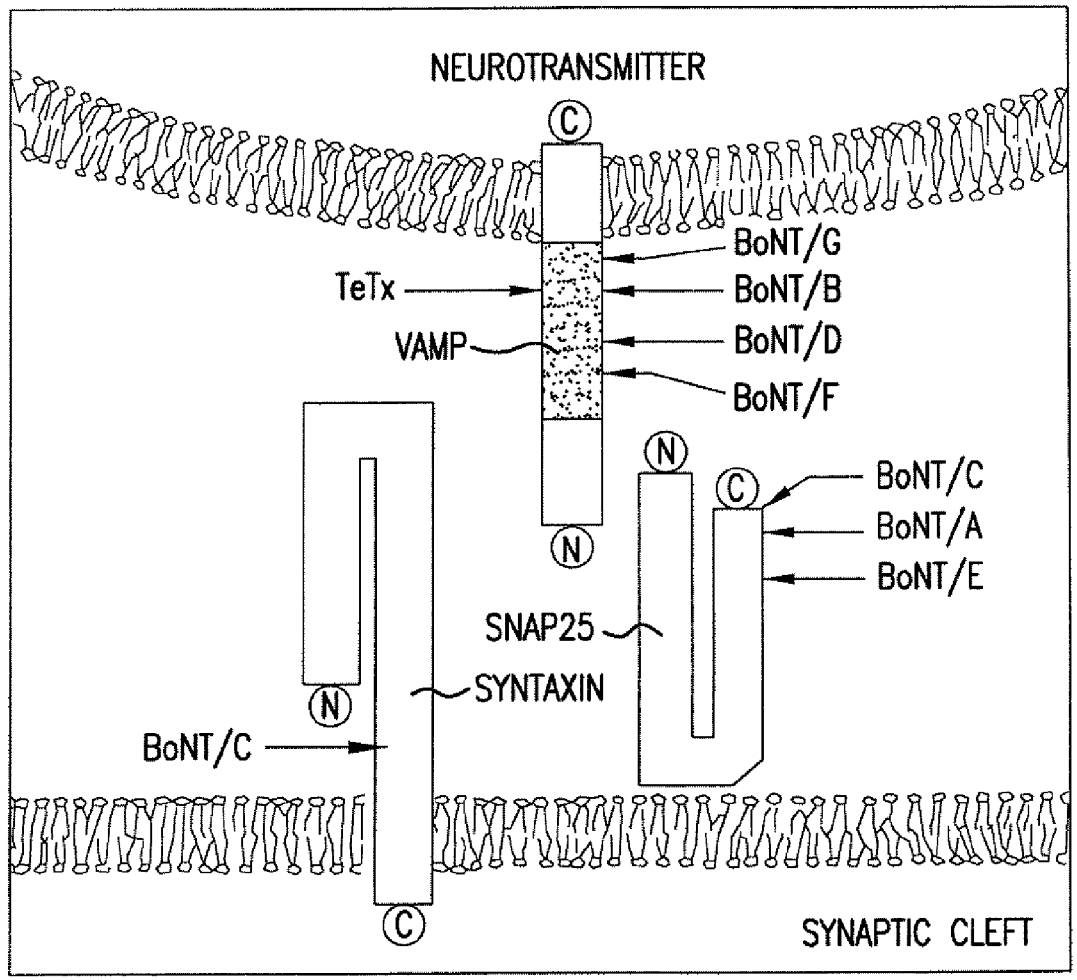
FIG. 3 shows the subcellular localization at the plasma membrane and sites of cleavage of SNAP-25, VAMP and syntaxin. VAMP is bound to synaptic vesicle membrane, whereas SNAP-25 and syntaxin are bound to the target plasma membrane. BoNT/A and /E cleave SNAP-25 close to the carboxy-terminus, releasing nine or 26 residues, respectively. BoNT/B, /D, /F, /G and TeNT act on the conserved central portion of VAMP (dotted) and release the amino-terminal portion of VAMP into the cytosol. BoNT/C1 cleaves SNAP-25 close to the carboxy-terminus as well as cleaving syntaxin at a single site near the cytosolic membrane surface. The action of BoNT/B, /C1, /D, /F, /G and TeNT results in release of a large portion of the cytosolic domain of VAMP or syntaxin, while only a small portion of SNAP-25 is released by selective proteolysis by BoNT/A, /C1 or /E.

SNAP-25, a protein of about 206 residues lacking a transmembrane segment, is associated with the cytosolic surface of the nerve plasmalemma (FIG. 3; see, also, Hodel et al., *Int. J. Biochemistry and Cell Biology* 30:1069-1073 (1998)). In addition to homologs highly conserved from *Drosophila* to mammals, SNAP-25-related proteins also have been cloned from yeast. SNAP-25 is required for axonal growth during development and may be required for nerve terminal plasticity in the mature nervous system. In humans, two isoforms are differentially expressed during development; isoform a is constitutively expressed beginning in the embryo stage, while isoform b appears at birth and predominates in adult life. SNAP-25 analogues such as SNAP-23 also are expressed outside the nervous system, for example, in pancreatic cells.

VAMP is a protein of about 120 residues, with the exact length depending on the species and isotype. As shown in FIG. 3, VAMP contains a short carboxy-terminal segment inside the vesicle lumen while most of the molecule is exposed to the cytosol. The proline-rich amino-terminal thirty residues are divergent among species and isoforms while the central portion of VAMP (residues 30 to 96), which is rich in charged and hydrophilic residues and includes known cleavage sites, is highly conserved. VAMP is associated on the synaptic vesicle membrane with synaptophysin.

A variety of species homologs of VAMP are known in the art including human, rat, bovine, *Torpedo, Drosophila*, yeast, squid and *Aplysia* homologs. In addition, multiple isoforms of VAMP have been identified including VAMP-1, VAMP-2 and cellubrevin, and insensitive forms have been identified in non-neuronal cells. VAMP appears to be present in all vertebrate tissues although the distribution of VAMP-1 and VAMP-2 varies in different cell types. Chicken and rat VAMP-1 are not cleaved by TeNT or BoNT/B. These VAMP-1 homologs have a valine in place of glutamine present in human and mouse VAMP-1 at the TeNT or BoNT/B cleavage site. The substitution does not effect BoNT/D, IF or /G, which cleave both VAMP-1 and VAMP-2 with similar rates.

Syntaxin, located on the cytosolic surface of the nerve plasmalemma, is membrane-anchored via a carboxy-terminal segment with most of the protein exposed to the cytosol. Syntaxin colocalizes with calcium channels at the active zones of the presynaptic membrane, where neurotransmitter release takes place. In addition, syntaxin interacts with synaptotagmin, a protein of the SSV membrane, that forms a functional bridge between the plasmalemma and the vesicles. A variety of syntaxin isoforms have been identified. Two isoforms of slightly different length (285 and 288 residues) have been identified in nerve cells (isoforms 1A and 1B), with isoforms 2, 3, 4 and 5 present in other tissues. The isoforms have varying sensitivities to BoNT/C1, with the 1A, 1B, 2 and 3 syntaxin isoforms cleaved by this toxin.

A clostridial toxin substrate of the invention contains a donor fluorophore; an acceptor having an absorbance spectrum overlapping the emission spectrum of the donor fluorophore; and a clostridial toxin recognition sequence that includes a cleavage site, where the cleavage site intervenes between the donor fluorophore and the acceptor and where, under the appropriate conditions, resonance energy transfer is exhibited between the donor fluorophore and the acceptor. Thus, a clostridial toxin substrate is a polypeptide, peptide or peptidomimetic that is susceptible to cleavage by at least one clostridial toxin under conditions suitable for clostridial toxin protease activity.

As used herein, the term "donor fluorophore" means a molecule that, when irradiated with light of a certain wavelength, emits light, also denoted fluorescence, of a different wavelength. The term fluorophore is synonymous in the art with the term "fluorochrome."

The term "acceptor," as used herein, refers to a molecule that can absorb energy from, and upon excitation of, a donor fluorophore and is a term that encompasses fluorophores as well as non-fluorescent molecules. An acceptor useful in a clostridial toxin substrate of the invention has an absorbance spectrum which overlaps the emission spectrum of a donor fluorophore. An acceptor useful in the invention generally also has rather low absorption at a wavelength suitable for excitation of the donor fluorophore.

In a clostridial toxin substrate of the invention, an acceptor has an absorbance spectrum that overlaps the emission spectrum of the donor fluorophore. The term "overlapping," as used herein in reference to the absorbance spectrum of an acceptor and the emission spectrum of a donor fluorophore, means an absorbance spectrum and emission spectrum that are partly or entirely shared. Thus, in such overlapping spectra, the high end of the range of the donor fluorophore's emission spectrum is higher than the low end of the range of the acceptor's absorbance spectrum.

As used herein, the term "clostridial toxin recognition sequence" means a scissile bond together with adjacent or non-adjacent recognition elements sufficient for detectable proteolysis at the scissile bond by a clostridial toxin under conditions suitable for clostridial toxin protease activity.

A clostridial toxin substrate of the invention contains a cleavage site that "intervenes" between a donor fluorophore and an acceptor having an absorbance spectrum which overlaps the emission spectrum of the donor fluorophore. Thus, the cleavage site is positioned in between the fluorophore and acceptor such that cleavage at the site results in a first molecule containing the fluorophore and a second molecule containing the acceptor. It is understood that all or only a portion of the clostridial toxin recognition sequence can intervene between the donor fluorophore and acceptor.

The invention further provides a "composite" clostridial toxin substrate. Such a composite clostridial toxin substrate contains (a) a first member of a donor fluorophore-acceptor pair linked to a first partner of an affinity couple; and (b) a clostridial toxin recognition sequence containing a cleavage site, where the recognition sequence is linked to a second member of the donor fluorophore-acceptor pair and a second partner of the affinity couple, where the cleavage site intervenes between the second member of the donor fluorophore-acceptor pair and the second partner of the affinity couple, and where (a) and (b) are stably associated such that, under the appropriate conditions, resonance energy transfer is exhibited between the first and second members of the donor fluorophore-acceptor pair. Thus, a composite clostridial toxin substrate of the invention is, in effect, a bipartite clostridial toxin substrate in which the two parts are stably associated through the affinity couple. As for other clostridial toxin substrates, resonance energy transfer is altered upon cleavage of the composite substrate. It is understood that the clostridial toxin recognition sequences and cleavage sites described herein and well known in the art can be useful in composite clostridial toxin substrates as well as in non-composite clostridial toxin substrates, which do not necessarily contain an affinity couple.

The term "donor fluorophore-acceptor pair," as used herein, means a donor fluorophore and an acceptor that has an absorbance spectrum overlapping the emission spectrum of the donor fluorophore. Where the first member of the pair is a donor fluorophore, the second member of the pair will be an acceptor. Where the first member of the pair is an acceptor, the second member of the pair will be a donor fluorophore.

In one embodiment, the first member of the donor fluorophore-acceptor pair is a donor fluorophore, and the second member is an acceptor. In another embodiment, the first member of the donor fluorophore-acceptor pair is an acceptor, and the second member is a donor fluorophore. A variety of donor fluorophores and acceptors are useful in the composite clostridial toxin substrates of the invention, including the donor fluorophores and acceptors described herein. In one embodiment, the donor fluorophore is a lanthanide. Lanthanide donor fluorophores useful in a composite substrate of the invention include, without limitation, terbium, europium, dysprosium and samarium.

The term "affinity couple," as used herein, means two molecules that are capable of forming a stable, non-covalent association. Affinity couples useful in a composite substrate of the invention include, without limitation, streptavidin-biotin; S peptide-S protein; histidine tag-nickel chelate; antibody-antigen, for example, FLAG and anti-FLAG antibody; and receptor-ligand.

In one embodiment, the affinity couple is streptavidin-biotin. In a further embodiment, the first partner of the affinity couple is streptavidin, and the second partner is biotin. In another embodiment, the first partner of the affinity couple is biotin, and the second partner is streptavidin. In yet further embodiments, the affinity couple is streptavidin-biotin, and the donor fluorophore is terbium, europium, dysprosium or samarium.

Clostridial toxins have specific and distinct cleavage sites. BoNT/A cleaves a Gln-Arg bond; BoNT/B and TeNT cleaves a Gln-Phe bond; BoNT/C1 cleaves a Lys-Ala or Arg-Ala bond; BoNT/D cleaves a Lys-Leu bond; BoNT/E cleaves an Arg-Ile bond; BoNT/F cleaves a Gln-Lys bond; and BoNT/G cleaves an Ala-Ala bond (see Table 1). The scissile bond can be represented $P_1$-$P_1'$, and it is understood that a $P_1$ or $P_1'$ site, or both, can be substituted with another amino acid or amino acid mimetic in place of the naturally occurring residue. For example, BoNT/A substrates have been prepared in which the $P_1$ position (Gln) is modified to be an alanine, 2-aminobutyric acid or asparagine residue; these substrates were hydrolyzed by BoNT/A at the $P_1$-Arg bond (Schmidt and Bostian, *J. Protein Chem.* 16:19-26 (1997)). However, it is recognized that substitutions can be introduced at the $P_1$ position of the scissile bond, for example, a BoNT/A scissile bond, while conservation of the $P_1'$ residue is more often important for detectable proteolysis (Vaidyanathan et al., *J. Neurochem.* 72:327-337 (1999)). Thus, in one embodiment, the invention provides a clostridial toxin substrate in which the $P_1'$ residue is not modified or substituted relative to the naturally occurring residue in a target protein cleaved by the clostridial toxin. In another embodiment, the invention provides a clostridial toxin substrate in which the $P_1$ residue is modified or substituted relative to the naturally occurring residue in a target protein cleaved by the clostridial toxin; such a substrate retains susceptibility to peptide bond cleavage between the $P_1$ and $P_1'$ residues.

TABLE 1

Bond cleaved in human VAMP-2, SNAP-25 or syntaxin

| Toxin | Target | $P_4$-$P_3$-$P_2$-$P_1$—$P_1'$-$P_2'$-$P_3'$-$P_4'$ | SEQ ID NO |
|---|---|---|---|
| BoNT/A | SNAP-25 | Glu-Ala-Asn-Gln—Arg*-Ala-Thr-Lys | SEQ ID NO: 1 |
| BoNT/B | VAMP-2 | Gly-Ala-Ser-Gln—Phe*-Glu-Thr-Ser | SEQ ID NO: 3 |
| BoNT/C1 | syntaxin | Asp-Thr-Lys-Lys—Ala*-Val-Lys-Tyr | SEQ ID NO: 5 |
| BoNT/D | VAMP-2 | Arg-Asp-Gln-Lys—Leu*-Ser-Glu-Leu | SEQ ID NO: 6 |
| BoNT/E | SNAP-25 | Gln-Ile-Asp-Arg—Ile*-Met-Glu-Lys | SEQ ID NO: 8 |
| BoNT/F | VAMP-2 | Glu-Arg-Asp-Gln—Lys*-Leu-Ser-Glu | SEQ ID NO: 9 |
| BoNT/G | VAMP-2 | Glu-Thr-Ser-Ala—Ala*-Lys-Leu-Lys | SEQ ID NO: 10 |
| TeNT | VAMP-2 | Gly-Ala-Ser-Gln—Phe*-Glu-Thr-Ser | SEQ ID NO: 11 |

*Scissile bond shown in bold

Figure 4A:
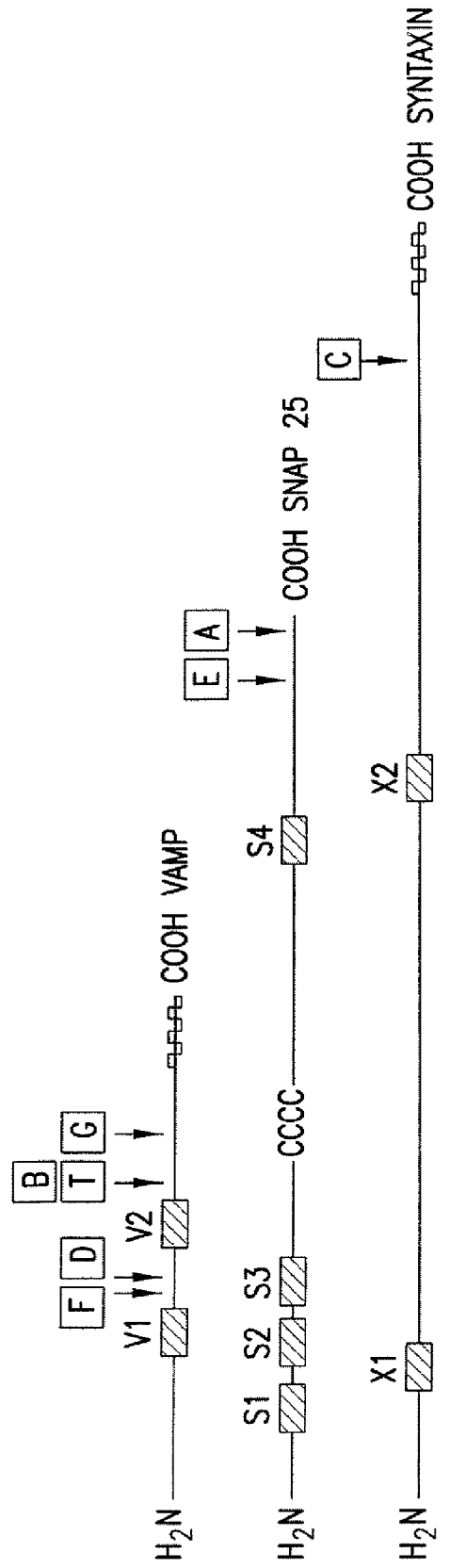
FIG. 4 shows the neurotoxin recognition motif of VAMP, SNAP-25 and syntaxin. (A) Hatched boxes indicate the presence and positions of a motif common to the three targets of clostridial neurotoxins. (B) The recognition motif is composed of hydrophobic residues ("h"); negatively charged Asp or Glu residues ("-") and polar residues ("p"); "x" represents any amino acid. The motif is included in regions of VAMP, SNAP-25 and syntaxin predicted to adopt an -helical conformation. (C) A top view of the motif in an -helical conformation is shown. Negatively charged residues align on one face, while hydrophobic residues align on a second face.
Figures 4B, 4C:
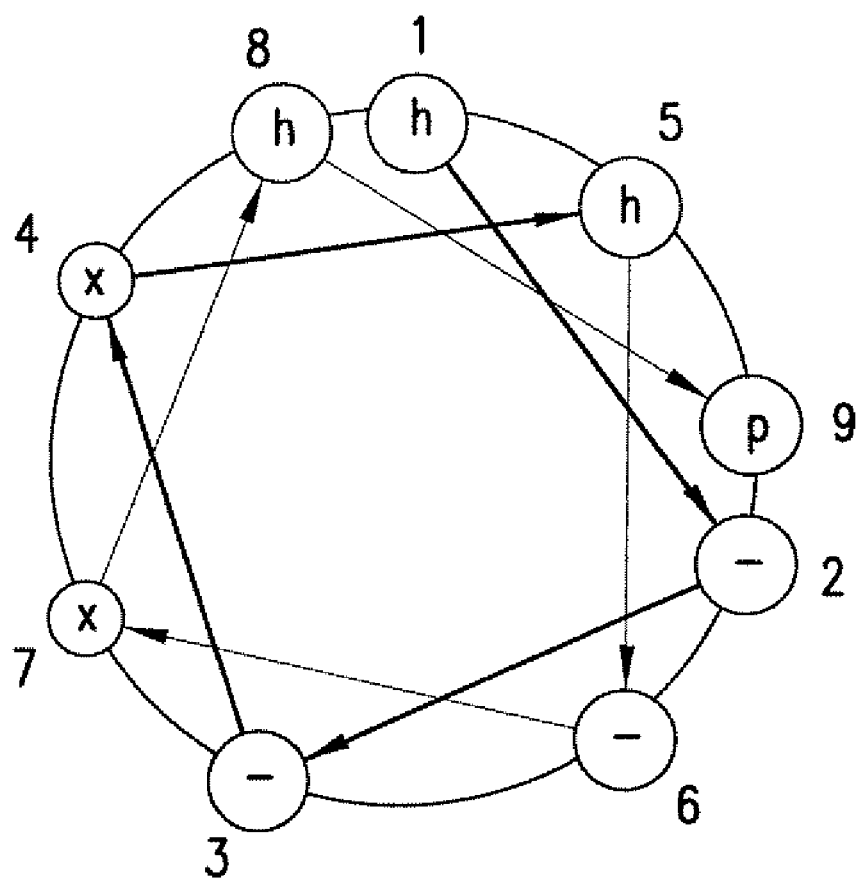

SNAP-25, VAMP and syntaxin share a short motif located within regions predicted to adopt an -helical conformation (see FIG. 4). This motif is present in SNAP-25, VAMP and syntaxin isoforms expressed in animals sensitive to the neurotoxins. In contrast, *Drosophila* and yeast homologs that are resistant to these neurotoxins and syntaxin isoforms not involved in exocytosis contain sequence variations in the -helical motif regions of these VAMP and syntaxin proteins.

Multiple repetitions of the -helical motif are present in proteins sensitive to cleavage by clostridial toxins: four copies are naturally present in SNAP-25; two copies are naturally present in VAMP; and two copies are naturally present in syntaxin (see FIG. 4A). Furthermore, peptides corresponding to the specific sequence of the -helical motifs can inhibit neurotoxin activity in vitro and in vivo, and such peptides can cross-inhibit different neurotoxins. In addition, antibodies raised against such peptides can cross-react among the three target proteins, indicating that this -helical motif is exposed on the cell surface and adopts a similar configuration in each of the three target proteins. Consistent with these findings, SNAP-25-specific, VAMP-specific and syntaxin-specific neurotoxins cross-inhibit each other by competing for the same binding site, although they do not cleave targets non-specifically. These results indicate that a clostridial toxin recognition sequence can include, if desired, at least one -helical motif. It is recognized that an -helical motif is not absolutely required for cleavage by a clostridial toxin as evidenced by 16-mer and 17-mer substrates for BoNT/A, as discussed further below.

Although multiple -helical motifs are found in SNAP-25, VAMP and syntaxin, in one embodiment the invention provides a clostridial toxin substrate in which the clostridial toxin recognition sequence includes a single-helical motif. In another embodiment, the invention provides a clostridial toxin substrate in which the clostridial toxin recognition sequence includes two or more-helical motifs. A BoNT/A or BoNT/E recognition sequence can include, for example, the S4-helical motif, alone or combined with one or more additional -helical motifs; BoNT/B, BoNT/G or TeNT recognition sequence can include, for example, the V2-helical motif, alone or combined with one or more additional-helical motifs; a BoNT/C1 recognition sequence can include, for example, the S4-helical motif, alone or combined with one or more additional -helical motifs, or X2-helical motif, alone or combined with one or more additional -helical motifs; and a BoNT/D or BoNT/F recognition sequence can include, for example, the V1-helical motif, alone or combined with one or more additional -helical motifs (see FIG. 4A).

A clostridial toxin substrate of the invention can contain one or multiple clostridial toxin cleavage sites for the same or different clostridial toxin. In one embodiment, a clostridial toxin substrate of the invention contains a single cleavage site. In another embodiment, a clostridial toxin substrate of the invention has multiple cleavage sites for the same clostridial toxin. These cleavage sites can be accompanied by the same or different clostridial toxin recognition sequences. In a further embodiment, a clostridial toxin substrate of the invention has multiple cleavage sites for the same clostridial toxin that intervene between the same donor fluorophore and acceptor. A clostridial toxin substrate of the invention can contain, for example, two or more, three or more, five or more, or ten or more cleavage sites for the same clostridial toxin intervening between the same or different donor fluorophore-acceptor pairs. A clostridial substrate of the invention also can have, for example, two, three, four, five, six, seven, eight, nine or ten cleavage sites for the same clostridial toxin intervening between the same or different donor fluorophore-acceptor pairs.

A clostridial toxin substrate of the invention containing multiple cleavage sites can contain cleavage sites and recognition sequences for different clostridial toxins. In one embodiment, a clostridial toxin substrate of the invention includes multiple cleavage sites for different clostridial toxins all intervening between the same donor fluorophore-acceptor pair. A clostridial toxin substrate of the invention can contain, for example, two or more, three or more, five or more, or ten or more cleavage sites for different clostridial toxins all intervening between the same donor fluorophore-acceptor pair. A clostridial toxin substrate of the invention also can contain, for example, two or more, three or more, five or more, or ten or more cleavage sites for different clostridial toxins intervening between at least two donor fluorophore-acceptor pairs. In particular embodiments, a clostridial substrate of the invention also has two, three, four, five, six, seven, eight, nine or ten cleavage sites for different clostridial toxins, where the cleavage sites intervene between the same or different donor fluorophore-acceptor pairs. A clostridial toxin substrate of the invention having multiple cleavage sites can have, for example, any combination of two, three, four, five, six, seven or eight cleavage sites for any combination of the following clostridial toxins: BoNT/A, BoNT/B, BoNT/C1, BoNT/D, BoNT/E, BoNT/F, BoNT/G and TeNT.

It is understood that a clostridial toxin substrate of the invention can be cleaved at a reduced or enhanced rate relative to SNAP-25, VAMP or syntaxin or relative to a similar peptide or peptidomimetic that does not contain extrinsic fluorophores. A clostridial toxin substrate of the invention such as a BoNT/A, BoNT/B, BoNT/C1, BoNT/D, BoNT/E, BoNT/F, BoNT/G or TeNT substrate, can be cleaved, for example, with an initial hydrolysis rate that is at least 5% of the initial hydrolysis rate, under otherwise identical conditions, of human SNAP-25, VAMP or syntaxin, where the clostridial toxin substrate and SNAP-25, VAMP or syntaxin each is present at a concentration of 1.0 mM.

Thus, a BoNT/A, BoNT/C1 or BoNT/E substrate of the invention can be cleaved, for example, with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human SNAP-25 by BoNT/A, BoNT/C1 or BoNT/E, respectively, where the substrate of the invention and human SNAP-25 each is present at a concentration of 1.0 mM. In other embodiments, a BoNT/A, BoNT/C1 or BoNT/E substrate of the invention is with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human SNAP-25 by BoNT/A, BoNT/C1 or BoNT/E, respectively, where the substrate of the invention and human SNAP-25 each is present at a concentration of 50 mM.

Similarly, a BoNT/B, BoNT/D, BoNT/F or BoNT/G substrate of the invention can be cleaved, for example, with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human VAMP-2 by BoNT/B, BoNT/D, BoNT/F or BoNT/G, respectively, where substrate of the invention and human VAMP-2 each is present at a concentration of 1.0 mM. In other embodiments, a BoNT/B, BoNT/D, BoNT/F or BoNT/G substrate of the invention is cleaved with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human VAMP-2 by BoNT/B, BoNT/D, BoNT/F or BoNT/G, respectively, where substrate of the invention and human VAMP-2 each is present at a concentration of 50 mM.

The invention also provides a BoNT/C1 substrate of the invention that is cleaved with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human syntaxin by BoNT/C1, where the BoNT/C1 substrate and human syntaxin each is present at a concentration of 1.0 mM. In other embodiments, the invention provides a BoNT/C1 substrate that is cleaved with an initial hydrolysis rate that is at least 5%, 10%, 20%, 30%, 40%, 50%, 60%, 70%, 80%, 90%, 100%, 150%, 200%, 250%, or 300% of the initial hydrolysis rate, under otherwise identical conditions, of human syntaxin by BoNT/C1, where the BoNT/C1 substrate and human syntaxin each is present at a concentration of 50 mM.

The "turnover number," or $k_{cat}$, is the rate of breakdown of a toxin-substrate complex. A clostridial toxin substrate of the invention can be cleaved with a $k_{cat}$ that is reduced or enhanced as compared to the $k_{cat}$ of human SNAP-25, human VAMP-2 or human syntaxin target proteins when cleaved by the same clostridial toxin under the same conditions. A clostridial toxin substrate of the invention such as a BoNT/A, BoNT/B, BoNT/C1, BoNT/D, BoNT/E, BoNT/F, BoNT/G or TeNT substrate, can be cleaved, for example, with a $k_{cat}$ of about 0.001 to about 4000 $sec^{-1}$. In one embodiment, a clostridial toxin substrate of the invention such as a BoNT/A, BoNT/B, BoNT/C1, BoNT/D, BoNT/E, BoNT/F, BoNT/G or TeNT substrate is cleaved with a $k_{cat}$ of about 1 to about 4000 $sec^{-1}$. In other embodiments, a BoNT/A, BoNT/B, BoNT/C1, BoNT/D, BoNT/E, BoNT/F, BoNT/G or TeNT substrate of the invention has a $k_{cat}$ of less than 5 $sec^-$, 10 $sec^{-1}$, 25 $sec^{-1}$, 50 $sec^{-1}$, 100 $sec^{-1}$, 250 $sec^{-1}$, 500 $sec^{-1}$, or 1000 $sec^{-1}$. A clostridial toxin substrate of the invention such as a BoNT/A, BoNT/B, BoNT/C1, BoNT/D, BoNT/E, BoNT/F, BoNT/G or TeNT substrate also can have, for example, a $k_{cat}$ in the range of 1 to 1000 $sec^{-1}$; 1 to 500 $sec^{-1}$; 1 to 250 $sec^{-1}$; 1 to 100 $sec^{-1}$; 1 to 50 $sec^{-1}$; 10 to 1000 $sec^{-1}$; 10 to 500 $sec^{-1}$; 10 to 250 $sec^{-1}$; 10 to 100 $sec^{-1}$; 10 to 50 $sec^{-1}$; to 1000 $sec^{-1}$; 25 to 500 $sec^{-1}$; 25 to 250 $sec^{-1}$; 25 to 100 $sec^{-1}$; 25 to 50 $sec^{-1}$; 50 to 1000 $sec^{-1}$; 50 to 500 $sec^{-1}$; 50 to 250 $sec^{-1}$; 50 to 100 $sec^{-1}$; 100 to 1000 $sec^{-1}$; 100 to 500 $sec^{-1}$; or 100 to 250 $sec^{-1}$. One skilled in the art understands the turnover number, $k_{cat}$, is assayed under standard kinetic conditions in which there is an excess of substrate.

In particular embodiments, a clostridial toxin substrate of the invention is a peptide or peptidomimetic. As used herein, the term "peptidomimetic" is used broadly to mean a peptide-like molecule that is cleaved by the same clostridial toxin as the peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines, and are cleaved by the same clostridial toxin as the peptide substrate upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α, α-dialkylglycine or α-aminocycloalkane carboxylic acid; an $N^α$-$C^α$ cyclized amino acid; an $N^α$-methylated amino acid; a β- or γ-amino cycloalkane carboxylic acid; an α, β-unsaturated amino acid; a. β,β-dimethyl or β-methyl amino acid; a. β-substituted-2,3-methano amino acid; an N-$C^δ$ or $C^α$-$C^δ$ cyclized amino acid; or a substituted proline or another amino acid mimetic. In addition, a peptidomimetic which mimics peptide secondary structure can contain, for example, a nonpeptidic. β-turn mimic; γ-turn mimic; mimic of, β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

The invention provides, for example, a botulinum toxin serotype A (BoNT/A) substrate containing a donor fluorophore; an acceptor having an absorbance spectrum overlapping the emission spectrum of the donor fluorophore; and a BoNT/A recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/A substrate of the invention can include, for example, at least six consecutive residues of SNAP-25, where the six consecutive residues include Gln-Arg, or a peptidomimetic thereof. Such a BoNT/A substrate also can have, for example, at least six consecutive residues of human SNAP-25, where the six consecutive residues include $Gln_{197}$-$Arg_{198}$, or a peptidomimetic thereof. In one embodiment, a BoNT/A substrate of the invention includes the amino acid sequence Glu-Ala-Asn-Gln-Arg-Ala-Thr-Lys (SEQ ID NO: 1), or a peptidomimetic thereof. In another embodiment, a BoNT/A substrate of the invention includes residues 187 to 203 of human SNAP-25 (SEQ ID NO: 2), or a peptidomimetic thereof. A variety of donor fluorophores and acceptors are useful in a BoNT/A substrate of the invention, including but not limited to, fluorescein-tetramethylrhodamine, DABCYL-EDANS, and Alexa Fluor® 488-QSY® 7. Additional donor fluorophores and acceptors useful in a BoNT/A substrate of the invention are described further herein below.

As used herein, the term "botulinum toxin serotype A recognition sequence" is synonymous with "BoNT/A recognition sequence" and means a scissile bond together with adjacent or non-adjacent recognition elements sufficient for detectable proteolysis at the scissile bond by a BoNT/A under conditions suitable for clostridial toxin protease activity. A scissile bond cleaved by BoNT/A can be, for example, Gln-Ala.

A variety of BoNT/A recognition sequences are well known in the art. A BoNT/A recognition sequence can have, for example, residues 134 to 206 or residues 137 to 206 of human SNAP-25 (Ekong et al., supra, 1997; U.S. Pat. No. 5,962,637). A BoNT/A recognition sequence also can include, without limitation, the sequence Thr-Arg-Ile-Asp-Glu-Ala-Asn-Gln-Arg-Ala-Thr-Lys-Met (SEQ ID NO: 27), or a peptidomimetic thereof, which corresponds to residues 190 to 202 of human SNAP-25; Ser-Asn-Lys-Thr-Arg-Ile-Asp-Glu-Ala-Asn-Gln-Arg-Ala-Thr-Lys (SEQ ID NO: 28), or a peptidomimetic thereof, which corresponds to residues 187 to 201 of human SNAP-25; Ser-Asn-Lys-Thr-Arg-Ile-Asp-Glu-Ala-Asn-Gln-Arg-Ala-Thr-Lys-Met (SEQ ID NO:

29), or a peptidomimetic thereof, which corresponds to residues 187 to 202 of human SNAP-25; Ser-Asn-Lys-Thr-Arg-Ile-Asp-Glu-Ala-Asn-Gln-Arg-Ala-Thr-Lys-Met-Leu (SEQ ID NO: 30), or a peptidomimetic thereof, which corresponds to residues 187 to 203 of human SNAP-25; Asp-Ser-Asn-Lys-Thr-Arg-Ile-Asp-Glu-Ala-Asn-Gln-Arg-Ala-Thr-Lys-Met (SEQ ID NO: 31), or a peptidomimetic thereof, which corresponds to residues 186 to 202 of human SNAP-25; or Asp-Ser-Asn-Lys-Thr-Arg-Ile-Asp-Glu-Ala-Asn-Gln-Arg-Ala-Thr-Lys-Met-Leu (SEQ ID NO: 32), or a peptidomimetic thereof, which corresponds to residues 186 to 203 of human SNAP-25. See, for example, Schmidt and Bostian, *J. Protein Chem.* 14:703-708 (1995); Schmidt and Bostian, supra, 1997; Schmidt et al., *FEBS Letters* 435:61-64 (1998); and Schmidt and Bostian, U.S. Pat. No. 5,965,699). If desired, a similar BoNT/A recognition sequence can be prepared from a corresponding (homologous) segment of another BoNT/A-sensitive SNAP-25 isoform or homolog such as, for example, murine, rat, goldfish or zebrafish SNAP-25 or can be any of the peptides disclosed herein or described in the art, for example, in U.S. Pat. No. 5,965,699.

A BoNT/A recognition sequence can correspond to a segment of a protein that is sensitive to cleavage by botulinum toxin serotype A, or can be substantially similar to a segment of a BoNT/A-sensitive protein. As illustrated in Table 2, a variety of naturally occurring proteins sensitive to cleavage by BoNT/A are known in the art and include, for example, human, mouse and rat SNAP-25; and goldfish SNAP-25A and SNAP-25B. Thus, a BoNT/A recognition sequence useful in a BoNT/A substrate of the invention can correspond, for example, to a segment of human SNAP-25, mouse SNAP-25, rat SNAP-25, goldfish SNAP-25A or 25B, or another naturally occurring protein sensitive to cleavage by BoNT/A. Furthermore, comparison of native SNAP-25 amino acid sequences cleaved by BoNT/A reveals that such sequences are not absolutely conserved (see Table 2 and FIG. 5), indicating that a variety of amino acid substitutions and modifications relative to a naturally occurring BoNT/A-sensitive SNAP-25 sequence can be tolerated in a BoNT/A substrate of the invention.

TABLE 3

Kinetic parameters of BoNT/A synthetic peptide substrates

| Peptide | Sequence[a] | SEQ ID NO: | Relative Rate[b] |
|---------|-------------|------------|------------------|
| [1-15]  | SNKTRIDEANQRATK | 28 | 0.03 |
| [1-16]  | SNKTRIDEANQRATKM | 29 | 1.17 |
| [1-17]  | SNKTRIDEANQRATKML | 30 | 1.00 |
| M16A    | SNKTRIDEANQRATKAL | 44 | 0.38 |
| M16X    | SNKTRIDEANQRATKXL | 45 | 1.20 |
| K15A    | SNKTRIDEANQRATAML | 46 | 0.12 |
| T14S    | SNKTRIDEANQRASKML | 47 | 0.26 |
| T14B    | SNKTRIDEANQRABKML | 48 | 1.20 |
| A13B    | SNKTRIDEANQRBTKML | 49 | 0.79 |
| Q11A    | SNKTRIDEANARATKML | 50 | 0.19 |
| Q11B    | SNKTRIDEANBRATKML | 51 | 0.25 |
| Q11N    | SNKTRIDEANNRATKML | 52 | 0.66 |
| N10A    | SNKTRIDEAAQRATKML | 53 | 0.06 |
| A9B     | SNKTRIDEBNQRATKML | 54 | 0.38 |
| E8Q     | SNKTRIDQANQRATKML | 55 | 2.08 |
| D7N     | SNKTRINEANQRATKML | 56 | 0.23 |

[a]Nonstandard amino acid abbreviations are B, 2-aminobutyric acid; X, 2-aminohexanoic acid (norleucine)
[b]Initial hydrolysis rates relative to peptide [1-17]. Peptide concentrations were 1.0 mM.

A clostridial toxin substrate of the invention, such as a BoNT/A substrate, can have one or multiple modifications as compared to a naturally occurring sequence that is cleaved by the corresponding clostridial toxin. For example, as compared to a 17-mer corresponding to residues 187 to 203 of human SNAP-25, substitution of Asp193 with Asn in the BoNT/A substrate resulted in a relative rate of proteolysis of 0.23; substitution of Glu194 with Gln resulted in a relative rate of 2.08; substitution of Ala195 with 2-aminobutyric acid resulted in a relative rate of 0.38; and substitution of Gln197 with Asn, 2-aminobutyric acid or Ala resulted in a relative rate of 0.66, 0.25, or 0.19, respectively (see Table 3). Furthermore, substitution of Ala199 with 2-aminobutyric acid resulted in a relative rate of 0.79; substitution of Thr200 with Ser or 2-aminobutyric acid resulted in a relative rate of 0.26 or 1.20, respectively; substitution of Lys201 with Ala resulted in a relative rate of 0.12; and substitution of Met202 with Ala or norleucine resulted in a relative rate of 0.38 or 1.20, respectively. See Schmidt and Bostian, supra, 1997. These results indicate that a variety of residues can be substituted in a clostridial toxin substrate of the invention as compared to a naturally occurring toxin-sensitive sequence. In the case of BoNT/A, these results indicate that residues including but not limited to Glu194, Ala195, Gln197, Ala199, Thr200 and Met202, Leu203, Gly204, Ser205, and Gly206, as well as residues more distal from the Gln-Arg scissile bond can be substituted or can be conjugated to a donor fluorophore or acceptor to produce a BoNT/A substrate of the invention. Such a BoNT/A substrate is detectably proteolyzed at the scissile bond by BoNT/A under conditions suitable for clostridial toxin protease activity. Thus, a BoNT/A substrate of the invention can include, if desired, one or several amino acid substitutions, additions or deletions relative to a naturally occurring SNAP-25 sequence.

In standard nomenclature, the sequence surrounding clostridial toxin cleavage sites is denoted $P_5$-$P_4$-$P_3$-$P_2$-$P_1$-$P_1$'-$P_2$'-$P_3$'-$P_4$'-$P_5$', with $P_1$-$P_1$' the scissile bond. In one embodiment, the invention provides a BoNT/A substrate or other clostridial toxin substrate in which the residue at position $P_1$, $P_2$, $P_3$, $P_4$, $P_5$, or $P_{>5}$ is substituted with an amino acid conjugated to a donor fluorophore or acceptor, and in which the residue at position $P_1$', $P_2$', $P_3$', $P_4$', $P_5$' or $P_{>5}$' is substituted with an amino acid conjugated to a donor fluorophore or acceptor. In another embodiment, the invention provides a BoNT/A substrate or other clostridial toxin substrate in which the residue at position $P_1$, $P_3$, $P_4$ or $P_{>5}$ is substituted with an amino acid conjugated to a donor fluorophore or acceptor, and in which the residue at position $P_2$', $P_3$', $P_5$' or $P_{>5}$' is substituted with an amino acid conjugated to a donor fluorophore or acceptor. It is further understood that the amino acid side chain of the residue conjugated to a donor fluorophore or acceptor can be otherwise identical to the residue present in the corresponding position of the naturally occurring target protein, or can contain, for example, a different side chain. Further provided by the invention is a BoNT/A substrate or other clostridial toxin substrate in which the residue at $P_3$, $P_4$ or $P_{>5}$ is substituted with an amino acid conjugated to a donor fluorophore or acceptor, and in which the residue at position $P_2$', $P_3$', $P_5$' or $P_{>5}$' is substituted with an amino acid conjugated to a donor fluorophore or acceptor. Again, the amino acid side chain of the residue conjugated to a donor fluorophore or acceptor can be otherwise identical to the residue present in the corresponding position of the naturally occurring target protein, or can contain, for example, a different side chain.

A BoNT/A substrate of the invention also can include, if desired, a carboxy-terminal amide. Thus, a BoNT/A substrate of the invention can be, for example, a peptide having at most twenty, thirty, forty or fifty residues and containing a carboxy-terminal amide.

Further provided by the invention is a botulinum toxin serotype B (BoNT/B) substrate containing a donor fluorophore; an acceptor having an absorbance spectrum overlapping the emission spectrum of the donor fluorophore; and a BoNT/B recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/B substrate of the invention can contain, for example, at least six consecutive residues of VAMP, where the six consecutive residues include Gln-Phe, or a peptidomimetic thereof. For example, a BoNT/B substrate of the invention can contain at least six consecutive residues of human VAMP-2, the six consecutive residues including $Gln_{76}$-$Phe_{77}$, or a peptidomimetic thereof. In one embodiment, a BoNT/B substrate includes the amino acid sequence Gly-Ala-Ser-Gln-Phe-Glu-Thr-Ser (SEQ ID NO: 3), or a peptidomimetic thereof. In other embodiments, a BoNT/B substrate includes residues 55 to 94 of human VAMP-2 (SEQ ID NO: 4); residues 60 to 94 of human VAMP-2 (SEQ ID NO: 4); or residues 60 to 88 of human VAMP-2 (SEQ ID NO: 4), or a peptidomimetic of one of these sequences. It is understood that a variety of donor fluorophores and acceptors are useful in a BoNT/B substrate of the invention; such donor fluorophore-acceptor combinations include, but are not limited to, fluorescein-tetramethylrhodamine; DABCYL-EDANS; and Alexa Fluor® 488-QSY® 7. A variety of additional donor fluorophores and acceptors useful in a BoNT/B substrate of the invention are known in the art and described further below.

As used herein, the term "botulinum toxin serotype B recognition sequence" is synonymous with "BoNT/B recognition sequence" and means a scissile bond together with adjacent or non-adjacent recognition elements sufficient for detectable proteolysis at the scissile bond by a BoNT/B under appropriate conditions. A scissile bond cleaved by BoNT/B can be, for example, Gln-Phe.

A variety of BoNT/B recognition sequences are well known in the art or can be defined by routine methods. Such a BoNT/B recognition sequence can include, for example, a sequence corresponding to some or all of the hydrophilic core of a VAMP protein such as human VAMP-1 or human VAMP-2. A BoNT/B recognition sequence can include, without limitation, residues 33 to 94, residues 45 to 94, residues 55 to 94, residues 60 to 94, residues 65 to 94, residues 60 to 88 or residues 65 to 88 of human VAMP-2 (SEQ ID NO: 4), or residues 60 to 94 of human VAMP-1 (SEQ ID NO: 96) (see, for example, Shone et al., Eur. J. Biochem. 217: 965-971 (1993) and U.S. Pat. No. 5,962,637). If desired, a similar BoNT/B recognition sequence can be prepared from a corresponding (homologous) segment of another BoNT/B-sensitive VAMP isoform or homolog such as human VAMP-1 or rat or chicken VAMP-2.

Thus, it is understood that a BoNT/B recognition sequence can correspond to a segment of a protein that is sensitive to cleavage by botulinum toxin serotype B, or can be substantially similar to such a segment of a BoNT/B-sensitive protein. As shown in Table 4, a variety of naturally occurring proteins sensitive to cleavage by BoNT/B are known in the art and include, for example, human, mouse and bovine VAMP-1 and VAMP-2; rat VAMP-2; rat cellubrevin; chicken VAMP-2; *Torpedo* VAMP-1; sea urchin VAMP; *Aplysia* VAMP; squid VAMP; *C. elegans* VAMP; *Drosophila* n-syb; and leech VAMP. Thus, a BoNT/B recognition sequence useful in a BoNT/B substrate of the invention can correspond, for example, to a segment of human VAMP-1 or VAMP-2, mouse VAMP-1 or VAMP-2, bovine VAMP-1 or VAMP-2, rat VAMP-2, rat cellubrevin, chicken VAMP-2, *Torpedo* VAMP-1, sea urchin VAMP, *Aplysia* VAMP, squid VAMP, *C. elegans* VAMP, *Drosophila* n-syb, leech VAMP, or another naturally occurring protein sensitive to cleavage by BoNT/B. Furthermore, as shown in Table 4, comparison of native VAMP amino acid sequences cleaved by BoNT/B reveals that such sequences are not absolutely conserved (see, also, FIG. 6), indicating that a variety of amino acid substitutions and modifications relative to a naturally occurring VAMP sequence can be tolerated in a BoNT/B substrate of the invention.

The invention also provides a botulinum toxin serotype C1 (BoNT/C1) substrate containing a donor fluorophore; an acceptor having an absorbance spectrum overlapping the emission spectrum of the donor fluorophore; and a BoNT/C1 recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/C1 substrate of the invention can have, for example, at least six consecutive residues of syntaxin, the six consecutive residues including Lys-Ala, or a peptidomimetic thereof. For example, a BoNT/C1 substrate of the invention can have at least six consecutive residues of human syntaxin, the six consecutive residues including $Lys_{253}$-$Ala_{254}$, or a peptidomimetic thereof. In one embodiment, a BoNT/C1 substrate contains the amino acid sequence Asp-Thr-Lys-Lys-Ala-Val-Lys-Tyr (SEQ ID NO: 5), or a peptidomimetic thereof.

A BoNT/C1 substrate of the invention also can contain, for example, at least six consecutive residues of SNAP-25, where the six consecutive residues include Arg-Ala, or a peptidomimetic thereof. Such a BoNT/C1 substrate can have, for example, at least six consecutive residues of human SNAP-25, the six consecutive residues including $Arg_{198}$-$Ala_{199}$, or a peptidomimetic thereof. An exemplary BoNT/C1 substrate contains residues 93 to 202 of human SNAP-25 (SEQ ID NO: 2), or a peptidomimetic thereof. As for all the clostridial toxin substrates of the invention, a variety of donor fluorophore-acceptor combinations are useful in a BoNT/C1 substrate, including but not limited to, fluorescein-tetramethylrhodamine; DABCYL-EDANS; and Alexa Fluor® 488-QSY® 7. Additional donor fluorophores and acceptors useful in a BoNT/C1 substrate of the invention are described herein below.

As used herein, the term "botulinum toxin serotype C1 recognition sequence" is synonymous with "BoNT/C1 recognition sequence" and means a scissile bond together with adjacent or non-adjacent recognition elements sufficient for detectable proteolysis at the scissile bond by a BoNT/C1 under appropriate conditions. A scissile bond cleaved by BoNT/C1 can be, for example, Lys-Ala or Arg-Ala.

It is understood that a BoNT/C1 recognition sequence can correspond to a segment of a protein that is sensitive to cleavage by botulinum toxin serotype C1, or can be substantially similar to a segment of a BoNT/C1-sensitive protein. As shown in Table 5, a variety of naturally occurring proteins sensitive to cleavage by BoNT/C1 are known in the art and include, for example, human, rat, mouse and bovine syntaxin 1A and 1B; rat syntaxins 2 and 3; sea urchin syntaxin; *Aplysia* syntaxin 1; squid syntaxin; *Drosophila* Dsynt1; and leech syntaxin 1. Thus, a BoNT/C1 recognition sequence useful in a BoNT/C1 substrate of the invention can correspond, for example, to a segment of human, rat, mouse or bovine syntaxin 1A or 1B, rat syntaxin 2, rat syntaxin 3, sea urchin syntaxin, *Aplysia* syntaxin 1, squid syntaxin, *Drosophila* Dsynt1, leech syntaxin 1, or another naturally occurring protein sensitive to cleavage by BoNT/C1. Furthermore, comparison of native syntaxin amino acid sequences cleaved by BoNT/C1 reveals that such sequences are not absolutely conserved (see Table 5 and FIG. 7), indicating that a variety of amino acid substitutions and modifications relative to a naturally occurring BoNT/C1-sensitive syntaxin sequence can be tolerated in a BoNT/C1 substrate of the invention.

TABLE 2

Cleavage of SNAP-25 and related protein[a,b,c,d]

| Species | Isoform | Cleavage Sites | SEQ ID NO: | Resistance to Cleavage by |
|---|---|---|---|---|
| | | BoNT/E ⇓      BoNT/A BoNT/C ⇓ ⇓ | | |
| human mouse rat | SNAP-25 | 174                 206<br>qnrqid ri mekadsnktridean qra tkmlgsg | | none[a] |
| human | SNAP-23 | 180            ara     end<br>qnpqik ri tdkadtnrdridian      kklids | | all[b] |
| mouse | SNAP-23 | 179                  end<br>qnqqiq ki tekadtnknridian tra kklids | | BoNT/A & C |
| chicken | SNAP-25 | 174                  end<br>qnrqid ri meklipikpglmkpt svq qrcsavvk | | BoNT/A & C |
| goldfish | SNAP-25A | 171                  end<br>qnrqid ri mdmadsnktridean tra tkmlgsg | | none |
| goldfish | SNAP-25B | 172                  end<br>qnrqid ri mekadsbktridean qra tkmlgsg | | none |
| Torpedo | SNAP-25 | -80                  end<br>qnaqvd ri vvkgdmnkaridean kha tkml | | BoNT/E[c] & A[d] |
| sea urchin | SNAP-25 | -80                  end<br>qnsqvg ri tskaesnegrinsad kra knilrnk | | (?)[e] |
| C-elegans | SNAP-25 | 283                  end<br>qnrqld ri hdkgsnevrvesank rak nlitk | | BoNT/A & C |
| Drosophila | SNAP-25 | 182                  end<br>qnrqid ri nrkgesneariavan qra hqllk | | BoNT/E & A[e] |
| leech | SNAP-25 | 181                  end<br>qnrqvd ri nnkmtsnqlrisdan kra skllke | | BoNT/A[c] |

[a] = In vitro cleavage of SNAP-25 requires 1000-fold higher BoNT/C concentration than BoNT/A or /E.
[b] = Substitution of p182r, or k185dd (boxes) induces susceptibility toward BoNT/E.
[c] = Resistance to BoNT/A possibly due to d189 or e189 substitution by v189, see box.
[d] = Note that Torpedo is susceptible to BoNT/A.
[e] = Note the presence of several non-conservative mutations around putative cleavage sites.

TABLE 4

Cleavage of VAMP[a,b]

| Species | Isoform | Cleavage Sites | SEQ ID NO: | Resistance to Cleavage by |
|---|---|---|---|---|
| | | BoNT/F BoNT/D    BoNT/B TeNT    BoNT/G<br>⇓ ⇓         ⇓        ⇓ | | |
| human mouse bovine | VAMP-1 | 53<br>dkvlerd qkl selddradalqagas qf ess aa klkrkyww | 92 | none |
| human mouse bovine | VAMP-2 | 51<br>dkvlerd qkl selddradalqagas qf ets aa klkrkyww | 90 | none |
| rat | VAMP-2 | 53<br>dkvlerd qkl selddradalqagas vf ess aa klkrkyww | 92 | TeNT & BoNT/B |
| rat | VAMP-2 | 51<br>dkvlerd qkl selddradalqagas qf ets aa klkrkyww | 90 | none |
| rat | Cellubrevin | 58<br>dkvlerd qkl selddradalqagas qf ets aa klkrkyww | 77 | none |

TABLE 4-continued

Cleavage of VAMP[a,b]

| | | | |
|---|---|---|---|
| rat | TI-VAMP | $^{146}$dlvaqrg erl ellidktenlvdssv tf ktt sr nlaramcm$^{175}$ | all |
| chicken | VAMP-1 | ----erd qkl selddradalqagas vf ess aa klkr---- | TeNT & BoNT/B |
| chicken | VAMP-2 | ----erd qkl selddradalqagas qf ets aa klkr---- | none |
| Torpedo | VAMP-1 | $^{55}$dkvlerd qkl selddradalqagas qf ess aa klkrkyww$^{94}$ | none |
| sea urchin | VAMP | $^{55}$dkvldrd qal svlddradalqqgas qf etn ag klkrkyww$^{74}$ | BoNT/F, D & G |
| Aplysia | VAMP | $^{41}$ekvldrd qki sqlddraealqagas qf eas ag klkrkyww$^{80}$ | BoNT/G |
| squid | VAMP | $^{60}$dkvlerd ski selddradalqagas qf eas ag klkrkyww$^{99}$ | BoNT/F & G |
| C. elegans | VAMP | $^{86}$nkvmerd vql nsldhraevlqngas qf qqs sr elkrqyww$^{115}$ | BoNT/F, D & G |
| Drosphila | syb[a] | $^{67}$ekvlerd qkl selgeradqleqgas qs eqq ag klkrkqww$^{106}$ | TeNT & BoNT/B & G |
| Drosphila | n-syb[b] | $^{61}$ekvlerd skl selddradalqqgas qf eqq ag klkrkfwl$^{100}$ | BoNT/F, & G |
| leech | VAMP | $^{49}$dkvlekd qkl aeldgradalqagas qf eas ag klkrkfww$^{88}$ | BoNT/G |

[a] = Sequence corrected in position 93 (f > s).
[b] = Sequence corrected in position 68 (t > s).

TABLE 5

Cleavage of syntaxin

| Species | Isoform | Cleavage Sites | SEQ ID NO: | Resistance to Cleavage by |
|---|---|---|---|---|
| | | BoNT/C ⇓ | | |
| human rat mouse bovine | syntaxin 1A | $^{245}$eravsdtk ka vkyqskar$^{262}$ | | no |
| human rat mouse bovine | syntaxin 1B | $^{244}$eravsdtk ka vkyqskar$^{261}$ | | no |
| rat | syntaxin 2 | $^{245}$ehakeetk ka ikyqskar$^{262}$ | | no |
| rat | syntaxin 3 | $^{244}$ekardetr ka mkyqgqar$^{261}$ | | no |
| rat | syntaxin 4 | $^{244}$ergqehvk ia lenqkkar$^{261}$ | | yes |
| chicken | syntaxin 1B | $^{239}$vpevfvtk sa vmyqcksr$^{259}$ | | expected |
| sea urchin | syntaxin | $^{243}$vrrqndtk ka vkyqskar$^{260}$ | | no |
| Aplysia | syntaxin 1 | $^{247}$etakmdtk ka vkyqskar$^{264}$ | | no |
| squid | syntaxin | $^{248}$etakvdtk ka vkyqskar$^{265}$ | | no |
| Drosophilia | Dsynt 1 | $^{248}$qtatqdtk ka lkyqskar$^{265}$ | | no |

TABLE 5-continued

Cleavage of syntaxin

| | | | 251 | | 268 | no |
|---|---|---|---|---|---|---|
| leech | ——————— | syntaxin 1 | etaaadtk | ka | mkyqsaar | |

A variety of naturally occurring SNAP-25 proteins also are sensitive to cleavage by BoNT/C1, including human, mouse and rat SNAP-25; goldfish SNAP-25A and 25B; and *Drosophila* and leech SNAP-25. Thus, a BoNT/C1 recognition sequence useful in a BoNT/C1 substrate of the invention can correspond, for example, to a segment of human, mouse or rat SNAP-25, goldfish SNAP-25A or 25B, Torpedo SNAP-25, zebrafish SNAP-25, *Drosophila* SNAP-25, leech SNAP-25, or another naturally occurring protein sensitive to cleavage by BoNT/C1. As discussed above in regard to variants of naturally occurring syntaxin sequences, comparison of native SNAP-25 amino acid sequences cleaved by BoNT/C1 reveals significant sequence variability (see Table 2 and FIG. 5 above), indicating that a variety of amino acid substitutions and modifications relative to a naturally occurring BoNT/C1-sensitive SNAP-25 sequence can be tolerated in a BoNT/C1 substrate of the invention.

The present invention further provides a botulinum toxin serotype D (BoNT/D) substrate containing a donor fluorophore; an acceptor having an absorbance spectrum overlapping the emission spectrum of the donor fluorophore; and a BoNT/D recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/D substrate of the invention can have, for example, at least six consecutive residues of VAMP, the six consecutive residues including Lys-Leu, or a peptidomimetic thereof. In one embodiment, a BoNT/D substrate contains at least six consecutive residues of human VAMP, the six consecutive residues including $Lys_{59}$-$Leu_{60}$, or a peptidomimetic thereof. In another embodiment, a BoNT/D substrate of the invention contains the amino acid sequence Arg-Asp-Gln-Lys-Leu-Ser-Glu-Leu (SEQ ID NO: 6), or a peptidomimetic thereof. In a further embodiment, a BoNT/D substrate of the invention includes residues 27 to 116 of rat VAMP-2 (SEQ ID NO: 7), or a peptidomimetic thereof. It is understood that a variety of donor fluorophore-acceptor combinations are useful in a BoNT/D substrate of the invention; such donor fluorophore-acceptor pairs include, but are not limited to, fluorescein-tetramethylrhodamine; DABCYL-EDANS; and Alexa Fluor® 488-QSY® 7. Additional exemplary donor fluorophores and acceptors useful in a BoNT/D substrate of the invention are provided herein below.

The term "botulinum toxin serotype D recognition sequence" is synonymous with "BoNT/D recognition sequence" and means a scissile bond together with adjacent or non-adjacent recognition elements sufficient for detectable proteolysis at the scissile bond by a BoNT/D under appropriate conditions. A scissile bond cleaved by BoNT/D can be, for example, Lys-Leu.

A variety of BoNT/D recognition sequences are well known in the art or can be defined by routine methods. A BoNT/D recognition sequence can include, for example, residues 27 to 116; residues 37 to 116; residues 1 to 86; residues 1 to 76; or residues 1 to 69 of rat VAMP-2 (SEQ ID NO: 7; Yamasaki et al., *J. Biol. Chem.* 269:12764-12772 (1994)). Thus, a BoNT/D recognition sequence can include, for example, residues 27 to 69 or residues 37 to 69 of rat VAMP-2 (SEQ ID NO: 7). If desired, a similar BoNT/D recognition sequence can be prepared from a corresponding (homologous) segment of another BoNT/D-sensitive VAMP isoform or homolog such as human VAMP-1 or human VAMP-2.

A BoNT/D recognition sequence can correspond to a segment of a protein that is sensitive to cleavage by botulinum toxin serotype D, or can be substantially similar to a segment of a BoNT/D-sensitive protein. As shown in Table 5, a variety of naturally occurring proteins sensitive to cleavage by BoNT/D are known in the art and include, for example, human, mouse and bovine VAMP-1 and VAMP-2; rat VAMP-1 and VAMP-2; rat cellubrevin; chicken VAMP-1 and VAMP-2; *Torpedo* VAMP-1; *Aplysia* VAMP; squid VAMP; *Drosophila* syb and n-syb; and leech VAMP. Thus, a BoNT/D recognition sequence useful in a BoNT/D substrate of the invention can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, *Torpedo* VAMP-1, *Aplysia* VAMP, squid VAMP, *Drosophila* syb or n-syb, leech VAMP, or another naturally occurring protein sensitive to cleavage by BoNT/D. Furthermore, as shown in Table 5 above, comparison of native VAMP amino acid sequences cleaved by BoNT/D reveals significant sequence variability (see, also, FIG. 6), indicating that a variety of amino acid substitutions and modifications relative to a naturally occurring BoNT/D-sensitive VAMP sequence can be tolerated in a BoNT/D substrate of the invention.

The present invention additionally provides a botulinum toxin serotype E (BoNT/E) substrate containing a donor fluorophore; an acceptor having an absorbance spectrum overlapping the emission spectrum of the donor fluorophore; and a BoNT/E recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/E substrate can contain, for example, at least six consecutive residues of SNAP-25, the six consecutive residues including Arg-Ile, or a peptidomimetic thereof. Such a BoNT/E substrate can have, for example, at least six consecutive residues of human SNAP-25, the six consecutive residues including $Arg_{180}$-$Ile_{181}$, or a peptidomimetic thereof. In one embodiment, a BoNT/E substrate includes the amino acid sequence Gln-Ile-Asp-Arg-Ile-Met-Glu-Lys (SEQ ID NO: 8), or a peptidomimetic thereof. In another embodiment, a BoNT/E substrate includes residues 156 to 186 of human SNAP-25 (SEQ ID NO: 2), or a peptidomimetic thereof. A variety of donor fluorophore-acceptor combinations are useful in a BoNT/E substrate of the invention. These donor fluorophore-acceptor combinations include, without limitation, fluorescein-tetramethylrhodamine, DABCYL-EDANS, Alexa Fluor® 488-QSY® 7, and additional donor fluorophores and acceptors described further below.

As used herein, the term "botulinum toxin serotype E recognition sequence" is synonymous with "BoNT/E recognition sequence" and means a scissile bond together with adjacent or non-adjacent recognition elements sufficient for detectable proteolysis at the scissile bond by a BoNT/E under appropriate conditions. A scissile bond cleaved by BoNT/E can be, for example, Arg-Ile.

One skilled in the art appreciates that a BoNT/E recognition sequence can correspond to a segment of a protein that is sensitive to cleavage by botulinum toxin serotype E, or can be substantially similar to a segment of a BoNT/E-sensitive protein. A variety of naturally occurring proteins sensitive to cleavage by BoNT/E are known in the art and include, for example, human, mouse and rat SNAP-25; mouse SNAP-23; chicken SNAP-25; goldfish SNAP-25A and SNAP-25B; zebrafish SNAP-25; C. elegans SNAP-25; and leech SNAP-25 (see Table 2). Thus, a BoNT/E recognition sequence useful in a BoNT/E substrate of the invention can correspond, for example, to a segment of human SNAP-25, mouse SNAP-25, rat SNAP-25, mouse SNAP-23, chicken SNAP-25, goldfish SNAP-25A or 25B, C. elegans SNAP-25, leech SNAP-25, or another naturally occurring protein sensitive to cleavage by BoNT/E. Furthermore, as shown in Table 2 and FIG. 5 above, comparison of native SNAP-23 and SNAP-25 amino acid sequences cleaved by BoNT/E reveals that such sequences are not absolutely conserved, indicating that a variety of amino acid substitutions and modifications relative to a naturally occurring BoNT/E-sensitive SNAP-23 or SNAP-25 sequence can be tolerated in a BoNT/E substrate of the invention.

The invention also provides a botulinum serotype NE (BoNT/A/E) substrate containing (a) a donor fluorophore; (b) an acceptor having an absorbance spectrum overlapping the emission spectrum of the donor fluorophore; and (c) a BoNT A or BoNT/E recognition sequence containing a cleavage site, where the cleavage site intervenes between the donor fluorophore and the acceptor and where, under the appropriate conditions, resonance energy transfer is exhibited between the donor fluorophore and the acceptor. As used herein, the term "botulinum serotype NE substrate" or "BoNT/A/E substrate" or "NE substrate" means a substrate that is susceptible to cleavage either by a botulinum serotype A toxin or a botulinum serotype E toxin. Such a botulinum serotype NE substrate also can be susceptible to cleavage by both the BoNT/A and BoNT/E toxins. Any of the BoNT/A or BoNT/E recognition sequences described herein or known in the art are useful in a BoNT/A/E substrate of the invention.

Further provided by the invention is a botulinum toxin serotype F (BoNT/F) substrate containing a donor fluorophore; an acceptor having an absorbance spectrum overlapping the emission spectrum of the donor fluorophore; and a BoNT/F recognition sequence that includes a cleavage site, where the cleavage site intervenes between the donor fluorophore and the acceptor and where, under the appropriate conditions, resonance energy transfer is exhibited between the donor fluorophore and the acceptor. Such a BoNT/F substrate can have, for example, at least six consecutive residues of VAMP, the six consecutive residues including Gln-Lys, or a peptidomimetic thereof. In one embodiment, a BoNT/F substrate has at least six consecutive residues of human VAMP, the six consecutive residues including $Gln_{58}$-$Lys_{59}$, or a peptidomimetic thereof. In another embodiment, a BoNT/F substrate of the invention includes residues 27 to 116 of rat VAMP-2 (SEQ ID NO: 7), or a peptidomimetic thereof. In a further embodiment, a BoNT/F substrate includes the amino acid sequence Glu-Arg-Asp-Gln-Lys-Leu-Ser-Glu (SEQ ID NO: 9), or a peptidomimetic thereof. Those skilled in the art of fluorescence resonance energy transfer understand that a variety of donor fluorophore-acceptor combinations are useful in a BoNT/F substrate of the invention. Non-limiting examples of donor fluorophore-acceptor pairs useful in a BoNT/F substrate of the invention include fluorescein-tetramethylrhodamine, DABCYL-EDANS, Alexa Fluor® 488-QSY® 7, as well as additional donor fluorophore-acceptors combinations described further below.

The term "botulinum toxin serotype F recognition sequence," as used herein, is synonymous with "BoNT/F recognition sequence" and means a scissile bond together with adjacent or non-adjacent recognition elements sufficient for detectable proteolysis at the scissile bond by a BoNT/F under appropriate conditions. A scissile bond cleaved by BoNT/F can be, for example, Gln-Lys.

A variety of BoNT/F recognition sequences are well known in the art or can be defined by routine methods. A BoNT/F recognition sequence can include, for example, residues 27 to 116; residues 37 to 116; residues 1 to 86; residues 1 to 76; or residues 1 to 69 of rat VAMP-2 ((SEQ ID NO: 7; Yamasaki et al., supra, 1994). A BoNT/F recognition sequence also can include, for example, residues 27 to 69 or residues 37 to 69 of rat VAMP-2 (SEQ ID NO: 7). It is understood that a similar BoNT/F recognition sequence can be prepared, if desired, from a corresponding (homologous) segment of another BoNT/F-sensitive VAMP isoform or homolog such as human VAMP-1 or human VAMP-2.

A BoNT/F recognition sequence can correspond to a segment of a protein that is sensitive to cleavage by botulinum toxin serotype F, or can be substantially similar to a segment of a BoNT/F-sensitive protein. A variety of naturally occurring proteins sensitive to cleavage by BoNT/F are known in the art and include, for example, human, mouse and bovine VAMP-1 and VAMP-2; rat VAMP-1 and VAMP-2; rat cellubrevin; chicken VAMP-1 and VAMP-2; Torpedo VAMP-1; Aplysia VAMP; Drosophila syb; and leech VAMP (see Table 5). Thus, a BoNT/F recognition sequence useful in a BoNT/F substrate of the invention can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, Torpedo VAMP-1, Aplysia VAMP, Drosophila syb, leech VAMP, or another naturally occurring protein sensitive to cleavage by BoNT/F. Furthermore, as shown in Table 5 above, comparison of native VAMP amino acid sequences cleaved by BoNT/F reveals that such sequences are not absolutely conserved (see, also, FIG. 6), indicating that a variety of amino acid substitutions and modifications relative to a naturally occurring BoNT/F-sensitive VAMP sequence can be tolerated in a BoNT/F substrate of the invention.

The present invention also provides a botulinum toxin serotype G (BoNT/G) substrate containing a donor fluorophore; an acceptor having an absorbance spectrum overlapping the emission spectrum of the donor fluorophore; and a BoNT/G recognition sequence that includes a cleavage site, where the cleavage site intervenes between the donor fluorophore and the acceptor and where, under the appropriate conditions, resonance energy transfer is exhibited between the donor fluorophore and the acceptor. A BoNT/G substrate can have, for example, at least six consecutive residues of VAMP, the six consecutive residues including Ala-Ala, or a peptidomimetic thereof. Such a BoNT/G substrate can have, for example, at least six consecutive residues of human VAMP, the six consecutive residues including $Ala_{83}$-$Ala_{84}$, or a peptidomimetic thereof. In one embodiment, a BoNT/G substrate contains the amino acid sequence Glu-Thr-Ser-Ala-Ala-Lys-Leu-Lys (SEQ ID NO: 10), or a peptidomimetic thereof. As discussed above in regard to other clostridial toxin substrates, a variety of donor fluorophore-acceptor combinations are useful in a BoNT/G substrate of the invention including for example, fluorescein-tetramethylrhodamine, DABCYL-EDANS, Alexa Fluor® 488-QSY® 7, and other donor fluorophore-acceptor combinations disclosed herein below or well known in the art.

As used herein, the term "botulinum toxin serotype G recognition sequence" is synonymous with "BoNT/G recognition sequence" and means a scissile bond together with adjacent or non-adjacent recognition elements sufficient for detectable proteolysis at the scissile bond by a BoNT/G under appropriate conditions. A scissile bond cleaved by BoNT/G can be, for example, Ala-Ala.

A BoNT/G recognition sequence can correspond to a segment of a protein that is sensitive to cleavage by botulinum toxin serotype G, or can be substantially similar to such a BoNT/G-sensitive segment. As illustration in Table 5 above, a variety of naturally occurring proteins sensitive to cleavage by BoNT/G are known in the art and include, for example, human, mouse and bovine VAMP-1 and VAMP-2; rat VAMP-1 and VAMP-2; rat cellubrevin; chicken VAMP-1 and VAMP-2; and *Torpedo* VAMP-1. Thus, a BoNT/G recognition sequence useful in a BoNT/G substrate of the invention can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, Torpedo VAMP-1, or another naturally occurring protein sensitive to cleavage by BoNT/G. Furthermore, as shown in Table 5 above, comparison of native VAMP amino acid sequences cleaved by BoNT/G reveals that such sequences are not absolutely conserved (see, also, FIG. 6), indicating that a variety of amino acid substitutions and modifications relative to a naturally occurring BoNT/G-sensitive VAMP sequence can be tolerated in a BoNT/G substrate of the invention.

Also provided by the invention is a tetanus toxin (TeNT) substrate containing a donor fluorophore; an acceptor having an absorbance spectrum overlapping the emission spectrum of the donor fluorophore; and a TeNT recognition sequence that includes a cleavage site, where the cleavage site intervenes between the donor fluorophore and the acceptor and where, under the appropriate conditions, resonance energy transfer is exhibited between the donor fluorophore and the acceptor.

A TeNT substrate of the invention can have, for example, at least six consecutive residues of VAMP, the six consecutive residues include Gln-Phe, or a peptidomimetic thereof. For example, such a TeNT substrate can have at least six consecutive residues of human VAMP-2, the six consecutive residues including $Gln_{76}$-$Phe_{77}$, or a peptidomimetic thereof. In one embodiment, a TeNT substrate contains the amino acid sequence Gly-Ala-Ser-Gln-Phe-Glu-Thr-Ser (SEQ ID NO: 11), or a peptidomimetic thereof. In another embodiment, the TeNT substrate contains residues 33 to 94 of human VAMP-2 (SEQ ID NO: 4); residues 25 to 93 of human VAMP-2 (SEQ ID NO: 4); or residues 27 to 116 of rat VAMP-2 (SEQ ID NO: 7), or a peptidomimetic of one of these sequences. A variety of donor fluorophore-acceptor combinations are useful in a TeNT substrate of the invention, including, without limitation, fluorescein-tetramethylrhodamine; DABCYL-EDANS; and Alexa Fluor® 488-QSY® 7. It is recognized that additional donor fluorophores and acceptors, including those described further below, can be useful in a TeNT substrate of the invention.

The term "tetanus toxin recognition sequence" means a scissile bond together with adjacent or non-adjacent recognition elements sufficient for detectable proteolysis at the scissile bond by a tetanus toxin under appropriate conditions. A scissile bond cleaved by TeNT can be, for example, Gln-Phe.

A variety of TeNT recognition sequences are well known in the art or can be defined by routine methods and include a sequence corresponding to some or all of the hydrophilic core of a VAMP protein such as human VAMP-1 or human VAMP-2. A TeNT recognition sequence can include, for example, residues 25 to 93 or residues 33 to 94 of human VAMP-2 (SEQ ID NO: 4; Cornille et al., *Eur. J. Biochem.* 222:173-181 (1994); Foran et al., *Biochem.* 33: 15365-15374 (1994)); residues 51 to 93 or residues 1 to 86 of rat VAMP-2 (SEQ ID NO: 7; Yamasaki et al., supra, 1994); or residues 33 to 94 of human VAMP-1 (SEQ ID NO: 96). A TeNT recognition sequence also can include, for example, residues 25 to 86, residues 33 to 86 or residues 51 to 86 of human VAMP-2 (SEQ ID NO: 4) or rat VAMP-2 (SEQ ID NO: 7). It is understood that a similar TeNT recognition sequence can be prepared, if desired, from a corresponding (homologous) segment of another TeNT-sensitive VAMP isoform or species homolog such as human VAMP-1 or sea urchin or *Aplysia* VAMP.

Thus, a TeNT recognition sequence can correspond to a segment of a protein that is sensitive to cleavage by tetanus toxin, or can be substantially similar to a segment of a TeNT-sensitive protein. As shown in Table 5 above, a variety of naturally occurring proteins sensitive to cleavage by TeNT are known in the art and include, for example, human, mouse and bovine VAMP-1 and VAMP-2; rat VAMP-2; rat cellubrevin; chicken VAMP-2; *Torpedo* VAMP-1; sea urchin VAMP; *Aplysia* VAMP; squid VAMP; *C. elegans* VAMP; *Drosophila* n-syb; and leech VAMP. Thus, a TeNT recognition sequence useful in a TeNT substrate of the invention can correspond, for example, to a segment of human VAMP-1 or VAMP-2, mouse VAMP-1 or VAMP-2, bovine VAMP-1 or VAMP-2, rat VAMP-2, rat cellubrevin, chicken VAMP-2, *Torpedo* VAMP-1, sea urchin VAMP, *Aplysia* VAMP, squid VAMP, *C. elegans* VAMP, *Drosophila* n-syb, leech VAMP, or another naturally occurring protein sensitive to cleavage by TeNT. Furthermore, comparison of native VAMP amino acid sequences cleaved by TeNT reveals that such sequences are not absolutely conserved (Table 5 and FIG. 6), indicating that a variety of amino acid substitutions and modifications relative to a naturally occurring TeNT-sensitive VAMP sequence can be tolerated in a TeNT substrate of the invention.

The present invention relies, in part, on fluorescence resonance energy transfer (FRET), a physical process by which energy is transferred non-radioactively from an excited donor fluorophore to an acceptor, which may be another fluorophore, through intramolecular long-range dipole-dipole coupling. FRET is dependent on the inverse sixth power of the intramolecular separation of the donor fluorophore and acceptor, and for effective transfer, the donor fluorophore and acceptor are in close proximity, separated, for example, by about 10 Å to about 100 Å. Effective energy transfer is dependent on the spectral characteristics of the donor fluorophore and acceptor as well as their relative orientation. For effective transfer over 10 to 100 Å, the quantum yield of the donor fluorophore generally is at least 0.1, and the absorption coefficient of the acceptor generally is at least 1000 (see Clegg, *Current Opinion in Biotech.* 6:103-110 (1995); and Selvin, *Nature Structural Biol.* 7:730-734 (2000)).

In a clostridial toxin substrate of the invention, the donor fluorophore and acceptor are selected so that the donor fluorophore and acceptor exhibit resonance energy transfer when the donor fluorophore is excited. One factor to be considered in choosing the donor fluorophore/acceptor pair is the efficiency of FRET between the donor fluorophore and acceptor. In one embodiment, the invention provides a clostridial toxin substrate in which, under optimal conditions, the efficiency of FRET between the donor fluorophore and acceptor is at least 10%. In another embodiment, the invention provides a clostridial toxin substrate in which, under optimal conditions, the efficiency of FRET between the donor fluorophore and acceptor is at least 20%. In still further embodiments, the invention provides a clostridial toxin substrate in which, under optimal conditions, the efficiency of FRET between the donor fluorophore and acceptor is at least 30%, 40%, 50%, 60%, 70% or 80%.

As is well known in the art, the efficiency of FRET is dependent on the separation distance and the orientation of the donor fluorophore and acceptor as described by the Förster equation, as well as the fluorescent quantum yield of the donor fluorophore and the energetic overlap with the acceptor. In particular, the efficiency (E) of FRET can be determined as follows:

$$E = 1 - F_{DA}/F_D = 1/(1 + (R/R_0)^6)$$

where $F_{DA}$ and $F_D$ are the fluorescence intensities of the donor fluorophore in the presence and absence of the acceptor, respectively, and R is the distance between the donor fluorophore and the acceptor.

The Förster radius ($R_o$) is the distance at which resonance energy transfer is 50% efficient, that is, 50% of excited donor fluorophores are deactivated by FRET. The magnitude of the Förster radius depends on the quantum yield of the donor fluorophore; the extinction coefficient of the acceptor; and the overlap between the donor fluorophore's emission spectrum and the acceptor's excitation spectrum.

$$R_O = [8.8 \times 10^{23} \times \kappa^2 \times n^{-4} \times QY_D \times J(\lambda)]^{1/6} \text{Å}$$

where $\kappa^2$=dipole orientation factor (range 0 to 4; $\kappa^2$=2/3 for randomly oriented donors and acceptors)

$QY_D$=fluorescence quantum yield of the donor in the absence of the acceptor n=refractive index $J(\lambda)$=spectral overlap integral=$I\epsilon_A(\lambda) \times F_D(\lambda) \times \lambda^4 d\lambda \text{cm}^3 \text{M}^{-1}$ where $\epsilon_A$=extinction coefficient of acceptor $F_D$=fluorescence emission intensity of donor as a fraction of the total integrated intensity (Förster, *Ann. Physik* 2:55-75 (1948)).

Typical Förster radius values for various donor fluorophore/acceptor pairs are given in Table 6 below (see, also, Wu and Brand, *Analytical Biochem.* 218:1-13 (1994), which is incorporated herein by reference). Comprehensive lists of Förster radii also are known in the art (see, for example, Berlman, *Energy Transfer Parameters of Aromatic Compounds* Academic Press, New York 1973). Furthermore, those skilled in the art recognize that component factors of the Förster radius ($R_o$) are dependent upon the environment such that the actual value observed can vary from the listed value.

Any of a number of donor fluorophores and acceptors in various combinations can be useful in a clostridial toxin substrate of the present invention. A donor fluorophore generally is selected such that there is substantial spectral overlap between the emission spectrum of the donor fluorophore overlaps with the excitation spectrum of the acceptor. In addition, a donor fluorophore can be selected, for example, to have an excitation maximum near a laser frequency such as Helium-Cadmium 442 nm or argon 488 nm, whereby laser light serves as an effective means to excite the donor fluorophore. In one embodiment, the wavelength maximum of the emission spectrum of the acceptor moiety is at least 10 nm greater than the wavelength maximum of the excitation spectrum of the donor fluorophore. In a further embodiment, the acceptor is a fluorophore having an emission spectrum in the red portion of the visible spectrum. In an additional embodiment, the acceptor is a fluorophore having an emission spectrum in the infrared region of the spectrum. A variety of donor fluorophore-acceptor pairs, and their Förster radii, are provided herein in Tables 6 and 7. See, also, Haugland, *Handbook of Fluorescent Probes and Research Chemicals* 6th Edition, Molecular Probes, Inc., Eugene, Oreg., 1996, which is incorporated herein by reference.

TABLE 6

| Donor fluorophore | Acceptor | Ro (Δ) | Reference |
|---|---|---|---|
| Fluorescein | TMR | 49-54 | Johnson et al., Biochemistry 32:6402-6410 (1993); Odom et al., Biochemistry 23:5069-5076 (1984) |
| Fluorescein | QSY ® 7 | 61 | — |
| EDANS | DABCYL | 33 | — |
| Napthalene | Dansyl | 22 | Haas et al., Proc. Natl. Acad. Sci. USA 72:1807-1811 (1975) |
| IANBD | DDPM | 25 | Kasprzyk et al., Biochemistry 22:1877-1882 (1983) |
| IAEDANS | DDPM | 25-29 | Dalbey et al., Biochemistry 22:4696-4706 (1983); Cheung et al., Biophys. Chem. 40:1-17 (1991) |
| DNSM | LY | 26-32 | Nalin et al., Biochemistry 28:2318-2324 (1985) |
| IAEDANS | IANBD | 27-51 | Franzen et al., Biochemistry 19:6080-6089 (1980); First et al., Biochemistry 28:3606-3613(1989) |
| ϵ-A | $_{F2}$DNB | 29 | Perkins et al., J. Biol. Chem. 259:8786-8793 (1984) |
| Pyrene | Bimane | 30 | Borochov-Neori and Montal, Biochemistry 28:1711-1718 (1989) |
| ANAI | IPM | 30 | Peerce and Wright, Proc. Natl. Acad. Sci. USA 83:8092-8096 (1986) |
| IAANS | IAF | 31 | Grossman, Biochim. Biophys. Acta 1040:276-280 (1990) |
| ϵ-A | $F_2$DPS | 31 | Perkins et al., supra, 1984 |
| ϵ-A | DDPM | 31 | Miki and Mihashi, Biochim. Biophys. Acta 533:163-172 (1978) |
| IAEDANS | TNP | 31-40 | Takashi et al., Biochemistry 21:5661-5668 (1982); dos Remedios and Cooke, Biochim. Biophys. Acta 788:193-205 (1984) |
| MNA | DACM | 32 | Amir and Haas, Biochemistry 26:2162-2175 (1987) |

TABLE 6-continued

| Donor fluorophore | Acceptor | Ro (Å) | Reference |
|---|---|---|---|
| PM | NBD | 32 | Snyder and Hammes, Biochemistry 24:2324-2331 (1985) |
| FITC | TNP-ATP | 32 | Amler et al., Biophys. J. 61:553-568 (1992) |
| DANZ | DABM | 34 | Albaugh and Steiner, J. Phys. Chem. 93:8013-8016 (1989) |
| NCP | CPM | 34 | Mitra and Hammes, Biochemistry 28:3063-3069 (1989) |
| NAA | DNP | 33-37 | McWherter et al., Biochemistry 25:1951-1963 (1986) |
| LY | TNP-ATP | 35 | Nalin, supra, 1985 |
| IAF | dil-$C_{18}$ | 35 | Shahrokh et al., J. Biol. Chem. 266:12082-12089 (1991) |
| IAF | TMR | 37 | Taylor et al., J. Cell Biol. 89:362-367 (1981) |
| FMA | FMA | 37 | Dissing et al., Biochim. Biophys. Acta 553:66-83 (1979) |
| PM | DMAMS | 38 | Lin and Dowben, J. Biol. Chem. 258:5142-5150 (1983) |
| mBBR | FITC | 38 | Tompa and Batke, Biochem. Int. 20:487-494 (1990) |
| mBBR | DABM | 38 | Kasprzak et al., Biochemistry 27:4512-4523 (1988) |
| ε-A | NBD | 38 | Miki and Iio, Biochim. Biophys. Acta 790:201-207 (1984) |
| Pyrene | Coumarin | 39 | Borochov-Neori and Montal, supra, 1989 |
| IPM | FNAI | 39 | Peerce and Wright, supra, 1986 |
| IAEDANS | DABM | 40 | Tao et al. Biochemistry 22:3059-3066 (1983) |
| IAEDANS | TNP-ATP | 40 | Tao et al., supra, 1983 |
| ε-A | IANBD | 40 | Miki and Wahl, Biochim. Biophys. Acta 786:188-196 (1984) |
| NBD | SRH | 40-74 | Wolf et al., Biochemistry 31:2865-2873 (1992) |
| ISA | TNP | 42 | Jacobson and Colman, Biochemistry 23:3789-3799 (1984) |
| Dansyl | ODR | 43 | Lu et al., J. Biol. Chem. 264:12956-12962 (1989) |
| DANZ | IAF | 44-49 | Cheung et al., Biochemistry 21:5135-5142 (1983) |
| FNAI | EITC | 45 | Peerce and Wright, supra, 1986 |
| NBD | LRH | 45-70 | Wolf et al., supra, 1992 |
| IAF | EIA | 46 | Taylor et al., supra, 1981 |
| FITC | ENAI | 46 | Peerce and Wright, supra, 1986 |
| Proflavin | ETSC | 46 | Robbins et al., Biochemistry 20:5301-5309 (1981) |
| CPM | TNP-ATP | 46 | Snyder and Hammes, supra, 1985 |
| IAEDANS | IAF | 46-56 | Franzen, supra, 1985; Grossman, supra, 1990 |
| CPM | Fluorescein | 47 | Thielen et al., Biochemistry 23:6668-6674 (1984) |
| IAEDANS | FITC | 49 | Jona et al., Biochim. Biophys. Acta 1028:183-199 (1990); Birmachu et al., Biochemistry 28:3940-3947 (1989) |
| IAF | TMR | 50 | Shahrokh et al., J. Biol. Chem. 266:12082-12089 (1991) |
| CF | TR | 51 | Johnson et al., supra, 1993 |
| CPM | TRS | 51 | Odom et al., supra, 1984 |
| ε-A | TNP-ATP | 51 | dos Remedios and Cooke, supra, 1984 |
| CPM | FM | 52 | Odom et al., supra, 1984 |
| LY | EM | 53 | Shapiro et al., J. Biol. Chem. 266:17276-17285 (1991) |
| FITC | EITC | 54 | Carraway et al., J. Biol. Chem. 264:8699-8707 (1989) |
| IAEDANS | DiO-$C_{14}$ | 57 | Shahrokh et al., supra, 1991 |
| IAF | ErITC | 58 | Amler et al., supra, 1992 |
| FITC | EM | 60 | Kosk-Kosicka et al., J. Biol. Chem. 264:19495-19499 (1989) |
| FITC | ETSC | 61-64 | Robbins et al., supra, 1981 |
| FITC | ErITC | 62 | Amler et al., supra, 1992 |
| BPE | CY5 | 72 | Ozinskas et al., Anal. Biochem. 213:264-270 (1993) |

TABLE 6-continued

| Donor fluorophore | Acceptor | Ro (Å) | Reference |
|---|---|---|---|
| Fluorescein | Fluorescein | 44 | — |
| BODIBY FL ® | BODIPY FL ® | 57 | — |

ANAI, 2-anthracence N-acetylimidazole;
BPE, B-phycoerythrin;
CF, carboxyfluorescein succinimidyl ester;
CPM, 7-diethylamino-3-(4'-maleimidylphenyl)-4-methylcoumarin;
CY5, carboxymethylindocyanine-N-hydroxysuccinimidyl ester;
dil-$C_{18}$, 1,1'-dioctadecyl-3-3,3,3',3'-tetramethyl-indocarbocyanine;
diO-$C_{14}$, 3,3'-ditetradecyloxacarbocyanine;
DABM, 4-dimethylaminophenylazo-phenyl-4'-maleimide;
DACM, (7-(dimethylamino)coumarin-4-yl)-acetyl;
DANZ, dansylaziridine; DDPM, N-(4-dimethylamino-3,5-dinitrophenyl)maleimide;
DMAMS, dimethylamino-4-maleimidostilbene;
DSMN, N-(2,5'-dimethoxystiben-4-yl)-maleimide;
DNP, 2,4-dinitrophneyl;
ε-A, 1,$N^6$-ethenoadenosine;
EIA, 5-(iodoacetetamido)eosin;
EITC, eosin-5-isothiocyanate;
ENAI, eosin N-acETYLIMIDAZOLE;
EM, eosin maleimide;
ErITC, erythrosin-5'-isothiocyanate;
ETSC, eosin thiosemicarazide;
$F_2$DNB, 1,5-difluro-2,4'-dinitrobenzene;
$F_2$DPS, 4,4'-difluoro-3,3'-dinitrophenylsulfone;
FITC, fluorescein thiosemicarbazide;
IAANS, 2-(4'-iodoacetamido)anilino)napthalene-6-sulfonic acid;
IAEDANS, 5-(2-((iodoacetyl)amino)ethyl)amino)-napthlene-1-sulfonic acid;
IAF, 5-iodoacetamidofluorescein;
IANBD, N-((2-(iodoacetoxy)ethyl)-N-methyl)amino-7-nitrobenz-2-oxa-1,3-diazole;
IPM, 3(4-isothiocyanatophenyl)7-diethyl-4-amino-4-methylcoumarin;
ISA, 4-(iodoacetamido)salicylic acid;
LRH, lissaminerhodamine;
LY, Lucifer yellow;
mBBR, monobromobiamane;
MNA, (2-methoxy-1-naphthyl)-methyl;
NAA, 2-napthoxyacetic acid;
NBD, 7-nirto-2,1,3-benzoxadiazol-4-yl;
NCP, N-cyclohexyl-N'-(1-pyrenyl)carbodiimide;
ODR, octadecylrhodamine;
PM, N-(1-pyrene)-maleimide;
SRH, sulforhodamine;
TMR, tetramethylrhodamine;
TNP, trinitrophenyl; and
TR, Texas Red An aromatic amino acid such as tryptophan or tyrosine also can be a donor fluorophore useful in a clostridial toxin substrate of the invention. Exemplary donor fluorophore-acceptor pairs in which tryptophan or tyrosine is the donor fluorophore and relevant Förster distances are shown in Table 7 below. Modified amino acids also can be useful as donor fluorophores or acceptors in a clostridial toxin substrate of the invention. Such fluorescent or quenching modified amino acids are known in the art and include, for example, the fluorescent amino acid L-pyrenylalanine (Pya) and the non-fluorescent acceptor p-nitrophenylalanine (Nop), as described, for example, in Anne et al., *Analytical Biochem.* 291:253-261 (2001).

TABLE 7

Förster Distances Using Trp as a Donor

| Donor | Acceptor | $R_o$ (Å) | Reference |
|---|---|---|---|
| Trp | Ru(III)(NH3)5 | 12-16 | Recchia et al., Biochim. Biophys. Acta 702: 105-111 (1982) |
| Trp | Nitrobenzoyl | 16 | Wiczk et al., J. Fluo 1: 273-286 (1991) |
| Trp | Dansyl | 21 | Steinberg, Annu. Rev. Biochem. 40: 83-114 (1971) |

TABLE 7-continued

Förster Distances Using Trp as a Donor

| Donor | Acceptor | $R_o$ (Å) | Reference |
|---|---|---|---|
| Trp | IAEDANS | 22 | Matsumoto and Hammes, Biochemistry 14: 214-224 (1975) |
| Trp | ANS | 23 | Conrad and Brand, Biochemistry 7: 777-787 (1968) |
| Trp | Anthroyloxy | 24 | Wiczk et al., supra, 1991 |
| Trp | TNB | 24 | Wu and Brand, Biochemistry 31: 7939-7947 (1992) |
| Trp | Anthroyl | 25 | Burgun et al., Arch. Biochem. Biophys. 286: 394-401 (1991) |
| Trp | Tyr-$NO_2$ | 26 | Steiner et al., J. Fluo. 1: 15-22 (1991) |
| Trp | Pyrene | 28 | Vekshin, Mol. Biol. 17: 827-832 (1983) |
| Trp | Heme | 29 | Ladokhin et al., Proc. SPIE 1640: 562-569 (1992) |
| Trp | NBS | 30 | Wiczk et al., supra, 1991 |
| Trp | DNBS | 33 | Wiczk et al., supra, 1991 |
| Trp | DPH | 40 | Le Doan et al., Biochim. Biophys. Acta 735: 259-270 (1983) |

In view of the above, it is understood that a variety of donor fluorophore/acceptor pairs can be useful in a clostridial toxin substrate of the invention. A donor fluorophore-acceptor pair useful in the invention can be, for example, the donor fluorophore fluorescein in combination with ROX (6-carboxy-X-rhodamine; Applied Biosystems Division of Perkin-Elmer Corporation; Foster City, Calif.); TAMRA (N,N,N',N'-tetramethyl-6-carboxy-rhodamine; Applied Biosystems); rhodamine; texas red or eosin. A donor fluorophore-acceptor pair useful in the invention also can be, for example, the donor fluorophore cascade blue with fluorescein as an acceptor; the donor fluorophore BODIPY® 530/550 (4,4-difluoro-5,7-diphenyl-4-bora-3a,4a-diaza-5-indacene in combination with BODIPY® 542/563 (4,4-difluoro-5-p-methoxyphenyl-4-bora-3a,4a-diaza-5-indacene) as an acceptor; or BODIPY® 542/563 (4,4-difluoro-5-p-methoxyphenyl-4-bora-3a,4a-diaza-S-indacene in combination with BODIPY® 564/570 (4,4-difluoro-5-styryl-4-bora-3a,4a-diaza-S-indacene as an acceptor. The numbers following the name BODIPY® reflect the excitation and emission maxima of the molecule; BODIPY® compounds are commercially available from Molecular Probes (Eugene Oreg.).

In one embodiment, the donor fluorophore is fluorescein. In a further embodiment, a clostridial toxin substrate of the invention contains a fluorescein as the donor fluorophore and tetramethylrhodamine as the acceptor. Such a substrate can be excited in the range of 480 to 505 nm, for example, at 488 nm or 492 nm, and emission detected at 520 nm ($\lambda_{em}$ fluorescein), 585 nm ($\lambda_{em}$ tetramethylrhodamine), or both. Prior to cleavage of the substrate at the clostridial toxin cleavage site, the tetramethylrhodamine emission intensity is greater than that of fluorescein; substrate cleavage results in a change in the ratio of fluorescein to tetramethylrhodamine intensity. Cleavage generally results in fluorescein becoming the dominant emitting fluorophore. Methods for preparing proteins and peptides containing fluorescein and tetramethylrhodamine are well known in the art (see, for example, Matsumoto et al., *Bioorganic & Medicinal Chemistry Letters* 10:1857-1861 (2000)).

A donor fluorophore useful in a substrate of the invention also can be, for example, EDANS ($\lambda_{Ab}$ 340 nM, $\lambda_{Em}$ 490 nm), which can be combined with an acceptor such as DABCYL. Where DABCYL and EDANS are combined in a clostridial toxin substrate of the invention, energy is transferred from the EDANS donor fluorophore to the DABCYL acceptor in the intact substrate, resulting in quenching of EDANS emission fluorescence. Upon cleavage at the toxin cleavage site, fluorescence of the cleaved EDANS product is increased and can be restored, for example, to the free donor fluorophore level. Efficient fluorescence quenching in the intact substrate occurs as a result of favorable energetic overlap of the EDANS emission spectrum and the DABCYL absorbance spectrum, and the relatively long excited state lifetime of the EDANS donor fluorophore (Wang et al., *Tetrahedron Lett.* 31:6493-6496 (1991); Holskin et al., *Anal. Biochem.* 226: 148-155 (1995); and Wang et al., *Anal. Biochem.* 210:351-359 (1993)).

Dansyl (DNS or 5-dimethylaminonaphthalene-1-sulfonyl) also can be a useful as a donor fluorophore or acceptor in a substrate of the invention. In one embodiment, a clostridial toxin substrate of the invention contains dansyl as the donor fluorophore; a dansyl donor can be combined, for example, with a nitrophenyl residue acceptor such as Phe(pNO$_2$), which acts as a quencher when in proximity to the dansyl donor fluorophore. Substrates containing a dansyl donor fluorophore, for example, in combination with a nitrophenyl residue can be prepared as described, for example, in Florentin et al., *Anal. Biochem.* 141:62-69 (1984) or Goudreau et al., Anal. Biochem. 219:87-95 (1994). In another embodiment, a clostridial toxin substrate contains dansyl as the acceptor. A dansyl acceptor can act as a quencher when combined, for example, with a donor fluorophore such as Trp ($\lambda_{ex}$ 290 nm, $\lambda_{em}$ 360 nm). In a substrate containing Trp and dansyl, Trp fluorescence can be quenched 60% by energy transfer to the dansyl group, and this quenching can be significantly reduced or abolished in the presence of toxin protease activity at the toxin cleavage site (see, for example, Geoghegan et al., *FEBS Letters* 262:119-122 (1990)).

It is understood that donor-acceptor pairs having well-separated emission maxima can be useful in the substrates and methods of the invention; well-separated emission maxima allow altered acceptor emission to be detected without donor emission contamination. A donor fluorophore, or acceptor, or both, can emit, for example, in the far-red, for example, greater than 650 nm. Such far-red emitting donor fluorophores and acceptors include cyanine dyes such as Cy5, Cy5.5 and Cy7 (Selvin, supra, 2000). In one embodiment, the invention provides a clostridial toxin substrate containing Cy3 and Cy5 as the donor fluorophore-acceptor pair; Cy3 emits maximally as 570 nm and Cy5 emits maximally at 670 nm. Such cyanine dyes can be prepared by straightforward synthesis, as described, for example, in Gruber et al., *Bioconj. Chem.* 11:161-166 (2000).

A donor fluorophore useful in a clostridial toxin substrate of the invention also can be, for example, a lanthanide atom, also known as a rare-earth element. Lanthanides such as terbium (Tb), europium (Eu), dysprosium (Dy) and samarium (Sm) have sharply spiked wavelengths, millisecond lifetimes following an excitation pulse, are unpolarized, and have high quantum yields. A lanthanide donor fluorophore such as a terbium or europium chelate can be combined with a variety of acceptors including organic dye acceptor. A Eu-chelate donor fluorophore can be combined, for example, with allophycocyanin (APC), and a Tb-chelate donor fluorophore can be combined, for example, with tetramethylrhodamine. Background fluorescence due to direct excitation is eliminated temporally; the lifetimes of organic acceptors generally are in the nanosecond range, while the sensitized emission follows the lifetime of the donor fluorophore and is on the order of microseconds to milliseconds (see Selvin, supra, 2000). Thus, determination of resonance energy transfer can be initiated relatively late following excitation, after non-specific interfering fluorescence has faded away. Lanthanide chelates are well known in the art and are commercially available, for example, from EG&G® Wallac (Turku, Finland).

A donor fluorophore useful in the invention also can be the well known fluorophore (7-methoxycoumarin-4-yl)acetyl (Mca), which can be combined with an acceptor such as the quencher 2,4-dinitrophenyl (Dnp). See, for example, Kakiuchi et al., *J. Virol. Methods* 80:77-84 (1999). When Mca is combined with the appropriate quencher such as Dnp in a clostridial toxin substrate of the invention, increased donor emission fluorescence from Mca ($\lambda_{Em}$ 393 nm) is detected upon cleavage at the clostridial toxin cleavage site and is indicative of toxin protease activity.

A donor fluorophore useful in a clostridial toxin substrate of the invention also can be, for example, a 2-aminobenzoyl (Abz) group, which can be combined, if desired, with a quencher such as 2,4-dinitrophenyl (Dnp). In an intact clostridial toxin substrate, the Dnp group quenches, by resonance energy transfer, the fluorescence of the Abz group; proteolytic cleavage of the substrate relieves quenching and results in an increase in fluorescence proportional to the concentration of the released Abz fragment. A clostridial toxin substrate containing, for example, Abz at the amino-terminus and a Dnp-derivatized residue such as lysine can be prepared by routine methods as described, for example, in Le Bonniec et al., *Biochemistry* 35:7114-7122 (1996)).

A donor fluorophore or acceptor useful in a clostridial toxin substrate of the invention also can be an Alexa Fluor® dye, commercially available from Molecular Probes (Eugene, Oreg.). Alexa Fluor® dyes useful in the invention include, for example, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660 and Alexa Fluor® 680.

A donor fluorophore or acceptor useful in the invention also can be a genetically encoded dye such as green fluorescence protein (GFP), blue fluorescence protein (BFP), cyan fluorescence protein (CFP), yellow fluorescence protein (YFP) or red fluorescence protein such as dsRed (BD Biosciences Clontech; Palo Alto, Calif.). Such genetically encoded donor fluorophores and acceptors are well known in the art as described, for example, in Selvin, supra, 2000, and Mahajan et al., *Chemistry and Biology* 6:401-409 (1999). For example, CFP has an excitation maxima at 433 nm and an emission maxima at 476 nm, and can be used as a donor fluorophore in combination with YFP as an acceptor (emission maxima at 527 nm). If desired, BFP can be used as a donor fluorophore in combination with GFP as the acceptor, or CFP can be used as the donor fluorophore in combination with YFP as the acceptor. Additional genetically encoded donor fluorophores and acceptors including *Aequorea* related fluorescent proteins are well known in the art, as described, for example, in U.S. Pat. No. 5,981,200. It is understood that genetically encoded dyes such as GFP, BFP, CFP or YFP can form FRET pairs with each other, or can be combined with other appropriate donor fluorophores or acceptors. In one embodiment, the invention provides a clostridial toxin substrate in which the donor fluorophore and acceptor both are genetically encoded. The desired toxin recognition sequence can be engineered such that the cleavage site is between the chosen donor fluorophore/acceptor pair, and the substrate expressed, for example, in bacteria and purified.

In another embodiment, the invention provides a clostridial toxin substrate containing an acceptor which is a fluorophore with a long fluorescent lifetime of at least a microsecond. Such an acceptor, which allows a time-resolved measurement of the fluorescence emission since the fluorescence lifetimes of impurities are generally in the nanosecond timescale, can enhance the signal to noise ratio. A useful donor fluorophore/acceptor pair for time-resolved fluorescence can be, for example, a europium cryptate donor fluorophore such as Eu-trisbipyridine cryptate (TBP-$EU^{3+}$, $\lambda_{Ex}$ 337 nm) combined with the 105 kDa phycobiliprotein acceptor fluorophore, allophycocyanin (Sittampalam et al., *Curr. Opin. Chem. Biol.* 1:384-391 (1997)). The Eu-trisbipyridine cryptate has two bipyridyl groups that harvest light and channel it to the caged $EU^{3+}$; this donor fluorophore has a long fluorescence lifetime and nonradiatively transfers energy to allophycocyanin when in close proximity to the acceptor, exhibiting greater than 50% transfer efficiency at a donor fluorophore-acceptor distance of 9.5 nm. Both TBP-$EU^{3+}$ and allophycocyanin and their spectroscopic characteristics are very stable in biological media, and allophycocyanin emits ($\lambda_{Em}$=665 nm) with the long lifetime of the donor, allowing time-resolved detection (Kolb et al., *J. Biomol. Screening* 1:203-210 (1996)). Methods of preparing substrates containing such donor fluorophore-acceptor pairs are well known in the art as described, for example, in Kolb et al., supra, 1996, and Sittampalam et al., supra, 1997.

In a further embodiment, the invention relies on a non-fluorescent acceptor, sometimes designated a "true quencher." A non-fluorescent acceptor can be useful, for example, in eliminating background fluorescence resulting from direct (nonsensitized) acceptor excitation. A variety of non-fluorescent acceptors are known in the art including, for example, DABCYL and QSY® 7 dyes (see Molecular Probes, supra, 1996).

A clostridial toxin substrate of the invention contains a clostridial toxin cleavage site which is positioned between a donor fluorophore and an acceptor. In one embodiment, the donor fluorophore is positioned amino-terminal of the cleavage site while the acceptor is positioned carboxy-terminal of the cleavage site. In another embodiment, the donor fluorophore is positioned carboxy-terminal of the cleavage site while the acceptor is positioned amino-terminal of the cleavage site.

One skilled in the art understands that there are several considerations in selecting and positioning a donor fluorophore and acceptor in a clostridial toxin substrate of the invention. The donor fluorophore and acceptor generally are positioned to minimize interference with substrate binding to, or proteolysis by, the clostridial toxin. Thus, a donor fluorophore and acceptor can be selected and positioned, for example, so as to minimize the disruption of bonded and non-bonded interactions that are important for binding, and to minimize steric hindrance. In addition, the spatial distance between the acceptor and donor fluorophore generally is limited to achieve efficient energy transfer from the donor fluorophore to the acceptor.

As discussed above, efficiency of energy transfer from donor fluorophore to acceptor is dependent, in part, on the spatial separation of the donor fluorophore and acceptor molecules. As the distance between the donor fluorophore and acceptor increases, there is less energy transfer to the acceptor, and the donor fluorescence signal therefore increases, even prior to cleavage. The overall increase in fluorescence yield of the donor fluorophore, upon cleavage of the substrate, is dependent upon many factors, including the separation distance between the donor fluorophore and acceptor in the substrate, the spectral overlap between donor fluorophore and acceptor, and the concentration of substrate used in an assay. One skilled in the art understands that, as the concentration of substrate increases, intermolecular quenching of the donor, even after proteolytic cleavage, can become a factor. This phenomenon is denoted the "inner filter effect" (see below).

The Förster distance, which is the separation between a donor fluorophore and an acceptor for 50% energy transfer, represents a spatial separation between donor fluorophore and acceptor that provides a good sensitivity. For peptide substrates, adjacent residues are separated by a distance of approximately 3.6 Å in the most extended conformation. For example, the calculated Förster distance for a fluorescein/tetramethylrhodamine pair is 55 Å, which would represent a spatial separation between fluorescein and tetramethylrhodamine of about 15 residues in the most extended conformation. Because peptides and peptidomimetics in solution rarely have a fully extended conformation, donor fluorophores and acceptors can be more widely separated than expected based on a calculation performed using 3.6 Å per residue and still remain within the Förster distance.

Förster theory is based on very weak interactions between donor fluorophore and acceptor; spectroscopic properties such as absorption of one fluorophore should not be altered in the presence of the other, defining the shortest distance range over which the theory is valid. It is understood that, for many donor fluorophore-acceptor pairs, Förster theory is valid when donor fluorophores and acceptors are separated by about 10 Å to 100 Å. However, for particular donor fluorophore-acceptor pairs, Förster theory is valid below 10 Å as determined by subpicosecond techniques (Kaschke and Ernsting, *Ultrafast Phenomenon in Spectroscopy* (Klose and Wilhelmi (Eds.)) Springer-Verlag, Berlin 1990.

Thus, in one embodiment, the invention provides a clostridial toxin substrate in which a donor fluorophore is separated from an acceptor by a distance of at most 100 Å. In other embodiments, the invention provides a clostridial toxin substrate in which a donor fluorophore is separated from an acceptor by a distance of at most 90 Å, 80 Å, 70 Å, 60 Å, 50 Å, 40 Å, 30 Å or 20 Å. In further embodiments, the invention provides a clostridial toxin substrate in which a donor fluorophore is separated from an acceptor by a distance of 10 Å to 100 Å, 10 Å to 80 Å, 10 Å to 60 Å, 10 Å to 40 Å, 10 Å to 20 Å, 20 Å to 100 Å, 20 Å to 80 Å, 20 Å to 60 Å, 20 Å to 40 Å, 40 Å to 100 Å, 40 Å to 40 Å or 40 Å to 60 Å.

One skilled in the art understands that a clostridial toxin substrate of the invention can be designed to optimize the efficiency of FRET as well as the ability to detect protease activity. One skilled in the art understands that a donor fluorophore can be selected, if desired, with a high quantum yield, and acceptor can be selected, if desired, with a high extinction coefficient to maximize the Förster distance. One skilled in the art further understands that fluorescence arising from direct excitation of an acceptor can be difficult to distinguish from fluorescence resulting from resonance energy transfer. Thus, it is recognized that a donor fluorophore and acceptor can be selected which have relatively little overlap of their excitation spectra such that the donor can be excited at a wavelength that does not result in direct excitation of the acceptor. It further is recognized that a clostridial toxin substrate of the invention can be designed so that the emission spectra of the donor fluorophore and acceptor overlap relatively little such that the two emissions can be readily distinguished. If desired, an acceptor having a high fluorescence quantum yield can be selected; such an acceptor is preferred if acceptor fluorescence emission is to be detected as the sole indicator of clostridial toxin protease activity, or as part of an emission ratio (see below).

It is understood that the donor fluorophore, acceptor, or both, can be located within the active site cavity of botulinum or tetanus toxin holoenzyme. One skilled in the art understands that, if desired, a clostridial toxin substrate can be designed such that, when bound by toxin, the donor fluorophore, acceptor, or both, is excluded from the active site cavity of toxin holoenzyme. Thus, in one embodiment, the invention provides a botulinum toxin substrate or tetanus toxin substrate in which, when bound by toxin, the donor fluorophore, acceptor, or both, is excluded from the active site cavity of clostridial toxin holoenzyme. The invention provides, for example, a BoNT/A, BoNT/B, BoNT/C1, BoNT/D, BoNT/E, BoNT/F or BoNT/G substrate in which, when bound by toxin, the donor fluorophore, acceptor, or both, is excluded from the active site cavity of toxin holoenzyme. In one embodiment, the invention provides a BoNT/A substrate containing at least six residues of human SNAP-25, where the six residues include $Gln_{197}$-$Arg_{198}$, in which the donor fluorophore, acceptor, or both, are not positioned between residues $Arg_{191}$ to $Met_{202}$, which can be within the active site cavity of BoNT/A holoenzyme. In another embodiment, the invention provides a BoNT/B substrate containing at least six residues of VAMP-2, where the six residues include $Gln_{76}$-$Phe_{77}$, in which the donor fluorophore, acceptor, or both, are not positioned between residues $Leu_{70}$ to $Ala_{81}$ of VAMP-2, which are within the active site cavity of BoNT/B holoenzyme.

In a complex of a VAMP substrate and the light chain of BoNT/B (LC/B), nearly all VAMP residues with side chains containing hydrogen bond acceptors or donors were hydrogen bonded with the LC/B. Thus, it is understood that a clostridial toxin substrate of the invention can be prepared, if desired, in which the potential for hydrogen bonding, for example, by Ser, Thr, Tyr, Asp, Glu, Asn or Gln residues is not diminished in the clostridial toxin substrate as compared to a native protein sensitive to cleavage by the toxin. Thus, in particular embodiments, the present invention provides a clostridial toxin substrate in which the potential for hydrogen-bonding is not diminished in the clostridial toxin substrate as compared to a native protein sensitive to cleavage by the corresponding botulinum or tetanus toxin.

It is understood that, in addition to a donor fluorophore, acceptor and clostridial toxin recognition sequence, a clostridial toxin substrate of the invention can include, if desired, one or more additional components. As an example, a flexible spacer sequence such as GGGGS (SEQ ID NO: 84) can be included in a clostridial toxin substrate of the invention. A substrate further also can include, without limitation, one or more of the following: an affinity tag such as HIS6, biotin, or an epitope such as FLAG, hemagluttinin (HA), c-myc, or AU1; an immunoglobulin hinge region; an N-hydroxysuccinimide linker; a peptide or peptidomimetic hairpin turn; or a hydrophilic sequence, or another component or sequence that promotes the solubility or stability of the clostridial toxin substrate.

Methods for modifying proteins, peptides and peptidomimetics to contain a donor fluorophore or acceptor are well known in the art (Fairclough and Cantor, *Methods Enzymol.* 48:347-379 (1978); Glaser et al., *Chemical Modification of Proteins* Elsevier Biochemical Press, Amsterdam (1975); Haugland, *Excited States of Biopolymers* (Steiner Ed.) pp. 29-58, Plenum Press, New York (1983); Means and Feeney, *Bioconjugate Chem.* 1:2-12 (1990); Matthews et al., *Methods Enzymol.* 208:468-496 (1991); Lundblad, *Chemical Reagents for Protein Modification* 2nd Ed., CRC Press, Boca Raton, Fla. (1991); Haugland, supra, 1996). A variety of groups can be used to couple a donor fluorophore or acceptor, for example, to a peptide or peptidomimetic containing a clostridial toxin recognition sequence. A thiol group, for example, can be used to couple a donor fluorophore or acceptor to the desired position in a peptide or peptidomimetic to produce a clostridial toxin substrate of the invention. Haloacetyl and maleimide labeling reagents also can be used to couple donor fluorophores or acceptors in preparing a substrate of the invention (see, for example, Wu and Brand, supra, 1994.

Donor fluorophores and acceptors including proteins such as GFP and allophycocyanin (APC) can be attached to a clostridial toxin recognition sequence by a variety of means. A donor fluorophore or acceptor can be attached by chemical means via a cross-linker moiety. Cross-linkers are well known in the art, including homo- or hetero-bifunctional cross-linkers such as BMH and SPDP. Where the donor fluorophore or acceptor is a protein, well known chemical methods for specifically linking molecules to the amino- or carboxy-terminus of a protein can be employed. See, for example, "Chemical Approaches to Protein Engineering" in *Protein Engineering—A Practical Approach* Rees et al. (Eds) Oxford University Press, 1992.

One skilled in the art understands that contaminating substrates containing only the donor fluorophore can result in high fluorescence background. Such background can be reduced or prevented, for example, by using a relative excess of acceptor to donor fluorophore in preparation of the clostridial toxin substrate.

The present invention also provides kits for determining clostridial toxin protease activity in a sample. The kit contains a clostridial toxin substrate of the invention in a vial or other container. The kit generally also includes instructions for use. In one embodiment, a kit of the invention further includes as a positive control a known amount of the botulinum or tetanus toxin capable of cleaving the clostridial toxin substrate included in the kit. In another embodiment, the kit contains a clostridial toxin substrate of the invention and further includes one or both cleavage products as a positive controls. In a particular embodiment, the kit contains a clostridial toxin substrate of the invention and the corresponding cleavage product that includes the donor fluorophore as a positive control. A kit of the invention optionally can include a container with buffer suitable for clostridial toxin protease activity. A described further herein below, the methods of the invention can be practiced with a combination of clostridial toxin substrates. Thus, in one embodiment, the invention provides a kit for determining clostridial toxin protease activity that includes at least two clostridial toxin substrates of the invention.

The present invention also provides clostridial toxin targets useful for detecting clostridial toxin protease activity. A clostridial toxin target is a polypeptide, peptide or peptidomimetic which contains a donor fluorophore; an acceptor; and a clostridial toxin recognition sequence that includes a cleavage site, where the cleavage site intervenes between the donor fluorophore and the acceptor and where, under the appropriate conditions, energy transfer is exhibited between the donor fluorophore and the acceptor. Energy can be transferred, for example, via collisional energy transfer and does not require that the acceptor have an absorbance spectrum which overlaps the emission spectrum of the donor fluorophore. Such a clostridial toxin target can include, for example, a botulinum toxin recognition sequence. Any of the clostridial toxin recognition sequences disclosed herein are useful in a substrate of the invention also can be useful in a clostridial toxin target of the invention. Selection and positioning of donor fluorophores and acceptors such that collisional energy transfer is exhibited is well known in the art, as described, for example, in Gershkkovich and Kholodovych, *J. Biochem. Biophys. Methods* 33:135-162 (1996).

The present invention also provides methods of determining clostridial toxin protease activity. Such methods are valuable, in part, because they are amenable to rapid screening and do not require separation of cleaved products from uncleaved substrate. Furthermore, the methods of the invention are applicable to crude samples as well as highly purified dichain toxins and further are applicable to clostridial toxin light chains, as described further below. The methods of the invention include the following steps: (a) treating a sample, under conditions suitable for clostridial toxin protease activity, with a clostridial toxin substrate that contains a donor fluorophore, an acceptor having an absorbance spectrum overlapping the emission spectrum of the donor fluorophore, and a clostridial toxin recognition sequence containing a cleavage site, where the cleavage site intervenes between the donor fluorophore and the acceptor and where, under the appropriate conditions, resonance energy transfer is exhibited between the donor fluorophore and the acceptor; (b) exciting the donor fluorophore; and (c) determining resonance energy transfer of the treated substrate relative to a control substrate, where a difference in resonance energy transfer of the treated substrate as compared to the control substrate is indicative of clostridial toxin protease activity. A method of the invention can be practiced with an acceptor which is a fluorophore, or with a non-fluorescent acceptor.

A method of the invention can be used to determine protease activity of any clostridial toxin. In one embodiment, a method of the invention relies on a BoNT/A substrate to determine BoNT/A protease activity. A BoNT/A substrate useful in a method of the invention can be any of the BoNT/A substrates disclosed herein, for example, a BoNT/A substrate containing at least six consecutive residues of SNAP-25, where the six consecutive residues include Gln-Arg. In another embodiment, a method of the invention relies on a BoNT/B substrate to determine BoNT/B protease activity. A BoNT/B substrate useful in a method of the invention can be any of the BoNT/B substrates disclosed herein, for example, a BoNT/B substrate containing at least six consecutive residues of VAMP, where the six consecutive residues include Gln-Phe. A method of the invention also can utilize a BoNT/C1 substrate to determine BoNT/C1 protease activity. A BoNT/C1 substrate useful in a method of the invention can be any of the BoNT/C1 substrates disclosed herein, for example, a BoNT/C1 substrate containing at least six consecutive residues of syntaxin, where the six consecutive residues include Lys-Ala, or containing at least six consecutive residues of SNAP-25, where the six consecutive residues include Arg-Ala.

In another embodiment, a method of the invention relies on a BoNT/D substrate to determine BoNT/D protease activity. A BoNT/D substrate useful in a method of the invention can be any of the BoNT/D substrates disclosed herein, for example, a BoNT/D substrate containing at least six consecutive residues of VAMP, where the six consecutive residues include Lys-Leu. In a further embodiment, a method of the invention relies on a BoNT/E substrate to determine BoNT/E protease activity. A BoNT/E substrate useful in a method of the invention can be any of the BoNT/E substrates disclosed herein, for example, a BoNT/E substrate containing at least six consecutive residues of SNAP-25, where the six consecutive residues include Arg-Ile. In yet a further embodiment, a method of the invention relies on a BoNT/F substrate to determine BoNT/F protease activity. A BoNT/F substrate useful in a method of the invention can be any of the BoNT/F substrates disclosed herein, for example, a BoNT/F substrate containing at least six consecutive residues of VAMP, where the six consecutive residues include Gln-Lys.

A method of the invention also can utilize a BoNT/G substrate to determine BoNT/G protease activity. A BoNT/G substrate useful in a method of the invention can be any of the BoNT/G substrates disclosed herein, for example, a BoNT/G substrate containing at least six consecutive residues of VAMP, where the six consecutive residues include Ala-Ala. A method of the invention also can be useful to determine TeNT protease activity and, in this case, relies on a TeNT substrate. Any of the TeNT substrates disclosed herein can be useful in a method of the invention, for example, a TeNT substrate containing at least six consecutive residues of VAMP, where the six consecutive residues include Gln-Phe.

A variety of samples are useful in the methods of the invention. Such samples include, but are not limited to, crude cell lysates; isolated clostridial toxins; isolated clostridial toxin light chains; formulated clostridial toxin products such as BOTOX®; and foodstuffs, including raw, cooked, partially cooked and processed foods and beverages.

In a method of the invention, resonance energy transfer can be determined by a variety of means. In one embodiment, the step of determining resonance energy transfer includes detecting donor fluorescence intensity of the treated substrate, where increased donor fluorescence intensity of the treated substrate as compared to the control substrate is indicative of clostridial toxin protease activity. In another embodiment, the step of determining resonance energy transfer includes detecting acceptor fluorescence intensity of the treated substrate, where decreased acceptor fluorescence intensity of the treated substrate as compared to the control substrate is indicative of clostridial toxin protease activity. In a further embodiment, the step of determining resonance energy transfer includes detecting the acceptor emission maximum and the donor fluorophore emission maximum, where a shift in emission maxima from near an acceptor emission maximum to near a donor fluorophore emission maximum is indicative of clostridial toxin protease activity. In an additional embodiment, the step of determining resonance energy transfer includes detecting the ratio of fluorescence amplitudes near an acceptor emission maximum to fluorescence amplitudes near a donor fluorophore emission maximum, where a decreased ratio in the treated sample as compared to the control sample is indicative of clostridial toxin protease activity. In yet a further embodiment, the step of determining resonance energy transfer is practiced by detecting the excited state lifetime of the donor fluorophore in the treated substrate, where an increased donor fluorophore excited state lifetime in the treated substrate as compared to the control substrate is indicative of clostridial toxin protease activity.

As discussed further below, a variety of conditions suitable for clostridial toxin protease activity are useful in a method of the invention. For example, conditions suitable for clostridial toxin protease activity can be provided such that at least 10% of the substrate is cleaved. Similarly, conditions suitable for clostridial toxin protease activity can be provided such that at least 20%, 30%, 40%, 50%, 60%, 70%, 80%, 90% or 95% of the clostridial toxin substrate is cleaved, or such that 100% of the clostridial toxin substrate is cleaved. In one embodiment, the conditions suitable for clostridial toxin protease activity are selected such that the assay is linear. In another embodiment, conditions suitable for clostridial toxin protease activity are provided such that at least 90% of the clostridial toxin substrate is cleaved. In a further embodiment, conditions suitable for clostridial toxin protease activity are provided such that at most 25% of the clostridial toxin substrate is cleaved. In yet further embodiments, conditions suitable for clostridial toxin protease activity are provided such that at most 20%, at most 15%, at most 10% or at most 5% of the clostridial toxin substrate is cleaved.

As used herein, the term "sample" means any biological matter that contains or potentially contains an active clostridial toxin, or light chain or proteolytically active fragment thereof. Thus, the term sample encompasses but is not limited to purified or partially purified clostridial toxin; recombinant single chain or dichain toxin with a naturally or non-naturally occurring sequence; chimeric toxin containing structural elements from multiple clostridial toxin species or subtypes; recombinant toxin light chain with a naturally occurring or non-naturally occurring sequence; bulk toxin; formulated product; cells or crude, fractionated or partially purified cell lysates, for example, engineered to include a recombinant nucleic acid encoding a clostridial toxin or light chain thereof, including bacterial, baculoviral and yeast lysates; raw, cooked, partially cooked or processed foods; beverages; animal feed; soil samples; water samples; pond sediments; lotions; cosmetics; and clinical formulations. It further is understood that the term sample includes tissue samples, including, without limitation, mammalian samples, primate samples and human samples, and encompassing samples such as intestinal samples, for example, infant intestinal samples, and samples obtained from a wound. Thus, it is understood that a method of the invention can be useful, without limitation, to assay for clostridial toxin protease activity in a food or beverage sample; to assay a sample from a human or animal, for example, exposed to a clostridial toxin or having one or more symptoms of a clostridial toxin; to follow activity during production and purification of clostridial toxin, and to assay formulated clostridial toxin products, including pharmaceuticals and cosmetics.

One skilled in the art understands that the methods of the invention are suitable for assaying any protein or molecule with clostridial toxin protease activity and do not rely, for example, on the ability of the clostridial toxin to bind to a neuronal cell or its ability to be internalized or translocated across the membrane. Thus, the methods of the invention are suitable for assaying for proteolytic activity of a clostridial toxin light chain, alone, and, although useful for assaying single or dichain heterotoxin, do not require the presence of the heavy chain. It further is understood that the methods of the invention are applicable to non-neuronal clostridial toxins including native and recombinant clostridial toxins, for example, clostridial toxins engineered to target pancreatic acinar cells.

In the methods of the invention, a sample is treated with a clostridial toxin substrate under conditions suitable for clostridial toxin protease activity. Exemplary conditions suitable for clostridial toxin protease activity are well known in the art, and further can be determined by routine methods. See, for example, Hallis et al., *J. Clin. Microbiol.* 34:1934-1938 (1996); Ekong et al., *Microbiol.* 143:3337-3347 (1997); Shone et al., WO 95/33850; Schmidt and Bostian, supra, 1995; Schmidt and Bostian, supra, 1997; Schmidt et al., supra, 1998; and Schmidt and Bostian, U.S. Pat. No. 5,965,699. It is understood that conditions suitable for clostridial toxin protease activity can depend, in part, on the specific clostridial toxin type or subtype being assayed and the purity of the toxin preparation. Conditions suitable for clostridial toxin protease activity generally include a buffer, such as HEPES, Tris or sodium phosphate, typically in the range of pH 5.5 to 9.5, for example, in the range of pH 6.0 to 9.0, pH 6.5 to 8.5 or pH 7.0 to 8.0. Conditions suitable for clostridial toxin protease activity also can include, if desired, dithiothreitol, -mercaptoethanol or another reducing agent, for example, where a dichain toxin is being assayed (Ekong et al., supra, 1997). In one embodiment, the conditions include DTT in the range of 0.01 mM to 50 mM; in other embodiments, the conditions include DTT in the range of 0.1 mM to 20 mM, 1 to 20 mM, or 5 to 10 mM. If desired, an isolated clostridial toxin or sample can be pre-incubated with a reducing agent, for example, with 10 mM dithiothreitol (DTT) for about 30 minutes prior to addition of clostridial toxin substrate.

Clostridial toxins are zinc metalloproteases, and a source of zinc, such as zinc chloride or zinc acetate, typically in the range of 1 to 500 μM, for example, 5 to 10 μM can be included, if desired, as part of the conditions suitable for clostridial toxin protease activity. One skilled in the art understands that zinc chelators such as EDTA generally are excluded from a buffer for assaying clostridial toxin protease activity.

Conditions suitable for clostridial toxin protease activity also can include, if desired, bovine serum albumin (BSA). When included, BSA typically is provided in the range of 0.1 mg/ml to 10 mg/ml. In one embodiment, BSA is included at a concentration of 1 mg/ml. See, for example, Schmidt and Bostian, supra, 1997.

The amount of clostridial toxin substrate can be varied in a method of the invention. Peptide substrate concentrations useful in a method of the invention include concentrations, for example, in the range of 5 µM to 3.0 mM. A peptide substrate can be supplied at a concentration, for example, of 5 µM to 500 µM, 5 µM to 50 µM, 50 µM to 3.0 mM, 0.5 mM to 3.0 mM, 0.5 mM to 2.0 mM, or 0.5 mM to 1.0 mM. The skilled artisan understands that the concentration of clostridial toxin substrate or the amount of sample can be limited, if desired, such that the assay is linear. At increasingly high concentrations of substrate or toxin, linearity of the assay is lost due to the "inner filter effect," which involves intermolecular energy transfer. Thus, in one embodiment, a method of the invention relies on a clostridial toxin substrate concentration which is limited such that intermolecular quenching does not occur. In another embodiment, a method of the invention relies on a clostridial toxin substrate concentration of less than 100 µM. In further embodiments, a method of the invention relies on a clostridial toxin substrate concentration of less than 50 µM or less than 25 µM. If desired, a linear assay also can be performed by mixing clostridial toxin substrate with corresponding, "unlabeled" substrate which lacks the donor fluorophore and acceptor of the clostridial toxin substrate. The appropriate dilution can be determined, for example, by preparing serial dilutions of clostridial toxin substrate in the corresponding unlabeled substrate.

The concentration of purified or partially purified clostridial toxin assayed in a method of the invention generally is in the range of about 0.0001 to 5000 ng/ml toxin, for example, about 0.001 to 5000 ng/ml, 0.01 to 5000 ng/ml, 0.1 to 5000 ng/ml, 1 to 5000 ng/ml, or 10 to 5000 ng/ml toxin, which can be, for example, purified recombinant light chain or dichain toxin or formulated clostridial toxin product containing human serum albumin and excipients. Generally, the amount of purified toxin used in a method of the invention is in the range of 0.1 pg to 10 µg. It is understood that purified, partially purified or crude samples can be diluted to within a convenient range for assaying for clostridial toxin protease activity against a standard curve. Similarly, one skilled in the art understands that a sample can be diluted, if desired, such that the assay for toxin protease activity is linear.

Conditions suitable for clostridial toxin protease activity also generally include, for example, temperatures in the range of about 20° C. to about 45° C., for example, in the range of 25° C. to 40° C., or the range of 35° C. to 39° C. Assay volumes often are in the range of about 5 to about 200 µl, for example, in the range of about 10 µl to 100 µl or about 0.5 µl to 100 µl, although nanoliter reaction volumes also can be used with the methods of the invention. Assay volumes also can be, for example, in the range of 100 µl to 2.0 ml or in the range of 0.5 ml to 1.0 ml.

Assay times can be varied as appropriate by the skilled artisan and generally depend, in part, on the concentration, purity and activity of the clostridial toxin. In particular embodiments, at least 10%, 20%, 30%, 40%, 50%, 60%, 70%, 80%, 90%, 95% or 100% of the clostridial toxin substrate is cleaved. In further embodiments, the protease reaction is stopped before more than 5%, 10%, 15%, 20%, 25% or 50% of the clostridial toxin substrate is cleaved. Protease reactions can be terminated, for example, by addition of $H_2SO_4$ as in Example I, addition of about 0.5 to 1.0 sodium borate, pH 9.0 to 9.5, or addition of zinc chelators. One skilled in the art understands that protease reactions can be terminated prior to exciting the donor fluorophore or determining energy transfer.

As an example, conditions suitable for BoNT/A protease activity can be incubation at 37° C. in a buffer such as 30 mM HEPES (pH 7.3) containing a reducing agent such as 5 mM dithiothreitol; a source of zinc such as 25 µM zinc chloride; and 1 µg/ml toxin (approximately 7 nM; Schmidt and Bostian, supra, 1997). BSA in the range of 0.1 mg/ml to 10 mg/ml, for example, 1 mg/ml BSA, also can be included when a sample is treated with a BoNT/A or other clostridial toxin substrate (Schmidt and Bostian, supra, 1997). If desired, BoNT/A, particularly dichain BoNT/A, can be pre-incubated with dithiothreitol, for example, for 30 minutes before addition of substrate. As another example, conditions suitable for clostridial toxin protease activity such as BoNT/A protease activity can be incubation at 37° C. for 30 minutes in a buffer containing 50 mM HEPES (pH 7.4), 1% fetal bovine serum, 10 µM $ZnCl_2$ and 10 mM DTT with 10 µM substrate (see Example I). As a further example, conditions suitable for clostridial toxin protease activity, for example BoNT/B activity, can be incubation in 50 mM HEPES, pH 7.4, with 10 µM zinc chloride, 1% fetal bovine serum and 10 mM dithiothreitol, with incubation for 90 minutes at 37° C. (Shone and Roberts, *Eur. J. Biochem.* 225:263-270 (1994); Hallis et al., supra, 1996); or can be, for example, incubation in 40 mM sodium phosphate, pH 7.4, with 10 mM dithiothreitol, optionally including 0.2% (v/v) Triton X-100, with incubation for 2 hours at 37° C. (Shone et al., supra, 1993). Conditions suitable for tetanus toxin protease activity or other clostridial toxin protease activity can be, for example, incubation in 20 mM HEPES, pH 7.2, and 100 mM NaCl for 2 hours at 37° C. with 25 µM peptide substrate (Cornille et al., supra, 1994).

In a method of the invention for determining clostridial toxin protease activity, a sample is treated with a clostridial toxin substrate that contains a first donor fluorophore, a first acceptor having an absorbance spectrum which overlaps the emission spectrum of the donor fluorophore, and a first clostridial toxin recognition sequence containing a cleavage site, where the cleavage site intervenes between the donor fluorophore and the acceptor and where, under the appropriate conditions, resonance energy transfer is exhibited between the donor fluorophore and the acceptor. If desired, a second clostridial toxin substrate can be included; this second substrate contains a second donor fluorophore and second acceptor having an absorbance spectrum which overlaps the emission spectrum of the second donor fluorophore, and a second clostridial toxin recognition sequence that is cleaved by a different clostridial toxin than the toxin that cleaves the first clostridial toxin recognition sequence. The donor fluorophore-acceptor pair in the second substrate can be the same or different from the donor fluorophore-acceptor pair in the first substrate. In this way, a single sample can be assayed for the presence of multiple clostridial toxins.

It is understood that one can assay for any combination of clostridial toxins, for example, two, three, four, five, six, seven, eight, nine, ten or more clostridial toxins. One can assay, for example, any combination of two, three, four, five, six, seven or eight of TeNT, BoNT/A, BoNT/B, BoNT/C1, BoNT/D, BoNT/E, BoNT/F and BoNT/G. For example, seven substrates, each containing fluorescein and tetramethylrhodamine flanking a BoNT/A, BoNT/B, BoNT/C1, BoNT/D, BoNT/E, BoNT/F or BoNT/G recognition sequence can be treated with a sample under conditions suitable for botulinum toxin protease activity before exciting the donor fluorescein at an absorption wavelength of about 488 nm and determining energy transfer. A shift in the emission maximum of the acceptor, tetramethylrhodamine (585 nm) to that of fluorescein (520 nm) is indicative of protease activity of at least one botulinum toxin. Such an assay can be useful, for example, for assaying food samples or tissue samples for the presence of any clostridial toxin and can be combined, if desired, with one or more subsequent assays for individual clostridial toxins or specific combinations of clostridial toxins.

In another embodiment, a single sample is assayed for two or more different clostridial toxins using two or more different clostridial toxin substrates with each substrate containing a different donor fluorophore-acceptor pair. The use of multiple substrates can be useful for extending the dynamic range of the assay, as described, for example, in U.S. Pat. No. 6,180,340. As an example of the use of multiple clostridial toxin substrates, a single sample can be assayed for BoNT/A and BoNT/B protease activity using a first clostridial toxin substrate containing the donor fluorophore fluorescein and the acceptor tetramethylrhodamine with an intervening BoNT/A recognition sequence, and a second clostridial toxin substrate containing the donor fluorophore EDANS and the acceptor DABCYL with an intervening BoNT/B recognition sequence. The first donor fluorophore, fluorescein, is excited at about 488 nm, and energy transfer is determined, with increased first donor fluorescence intensity at about 520 nm indicative of BoNT/A protease activity. The second donor fluorophore, EDANS, is excited at an absorption wavelength of about 340 nm, with increased second donor fluorescence intensity (490 nm) indicative of BoNT/B protease activity. Similarly, where two or more different donor fluorophores are to be used together to assay a single sample, one can combine, for example, any combination or all of the following lanthanides: terbium, dysprosium, europium and samarium (EG&G® Wallac). These lanthanides have spectra that are clearly distinguishable on the basis of decay time and wavelength. Those skilled in the art understand that the first donor fluorophore can be excited before, at the same time, or after excitation of the second donor fluorophore, and that energy transfer of the first substrate can be determined before, at the same time, or after determining energy transfer of the second substrate.

Multiple substrates also can be used in the methods of the invention to extend the range of the assay. In one embodiment, at least two clostridial substrate are used together at different dilutions; the substrates have donor fluorophore-acceptor pairs and, therefore, are separately detectable, but have recognition sequences for the same clostridial toxin. In another embodiment, otherwise identical clostridial toxin substrates with different donor fluorophore-acceptor pairs are used together at different dilutions to extend the range of the assay.

The methods of the invention involve exciting the donor fluorophore contained in the clostridial toxin substrate. One skilled in the art understands that a donor fluorophore generally is excited at or near the optimal absorption wavelength (excitation wavelength) of the donor fluorophore. Where the donor fluorophore is fluorescein, the donor can be excited, for example, at or near the optimal absorption wavelength of 488 nm.

Proteolysis of the clostridial toxin substrate, and hence clostridial toxin protease activity, can be detected by a variety of means, for example, by detecting an increased donor fluorescence intensity; a decreased acceptor fluorescence intensity; a shift in emission maxima from near the acceptor emission maximum to near the donor fluorophore emission maximum; a decreased ratio of fluorescence amplitudes near the acceptor emission maximum to the fluorescence amplitudes near the donor fluorophore emission maximum; or an increased donor fluorophore excited state lifetime. It is understood that the relevant fluorescence intensities or excited state lifetimes are detected at the appropriate selected wavelength or range of wavelengths. For example, where donor fluorescence intensity is detected, the appropriate selected wavelength at or near the emission maxima of the donor fluorophore, or a range of wavelengths encompassing or near to the emission maxima of the donor fluorophore.

It is recognized that changes in the absolute amount of substrate, excitation intensity, and turbidity or other background absorbance in the sample at the excitation wavelength effect the fluorescence intensities of donor and acceptor fluorophores roughly in parallel. Thus, it is understood that a ratio of emission intensities is independent of the absolute amount of substrate, excitation intensity, or turbidity or other background absorbance, and can be a useful indicator of clostridial toxin protease activity. Similarly, one skilled in the art understands that the excitation state lifetime of a donor fluorophore is independent of the absolute amount of substrate, excitation intensity, or turbidity or other background absorbance and can be useful in a method of the invention.

In one embodiment, donor fluorescence intensity is detected, with increased donor fluorescence intensity indicative of clostridial toxin protease activity. Such increased intensity can be, for example, at least two-fold, three-fold, five-fold, ten-fold, twenty-fold or more relative to fluorescence intensity at the same wavelength of the same clostridial toxin substrate not contacted with sample.

For detection of donor fluorescence intensity, excitation is set at the wavelength of donor fluorophore absorption, and the emission of the donor fluorophore is monitored. The emission wavelength of the donor fluorophore generally is selected such that little or no contribution from acceptor fluorescence is observed. The presence of acceptor quenches donor fluorescence. Energy transfer efficiency, E, is calculated from $E=1-I_{DA}/I_D$, where $I_{DA}$ and $I_D$ are donor intensities in the presence and absence of acceptor. Both are normalized to the same donor fluorophore concentration. If desired, time resolved measurements, for which donor fluorophore concentration is not required, can be performed, $E=1-\{T_{DA}\}/T_D$, where $\{T_{DA}\}$ and $\{T_D\}$ are amplitude-averaged lifetimes of donor fluorophore in the presence and absence of acceptor.

In one embodiment, a shift in emission maxima from near the acceptor emission maximum to near the donor fluorophore emission maximum is detected as a determination of resonance energy transfer. Where a tetramethylrhodamine acceptor is combined with the donor fluorophore fluorescein, one can detect a shift from predominantly red emission to predominantly green emission as an indicator of decreased resonance energy transfer and, therefore, of clostridial toxin protease activity. It is understood that the observed shift in emission maxima generally will not be a complete shift but that only part of the emission intensity will be shifted to near the donor fluorophore emission maximum.

In the methods of the invention, resonance energy transfer of the treated substrate is determined relative to a control substrate. Such a control substrate generally can be, for example, the same clostridial toxin substrate which is not treated with any sample, or which is treated with a defined sample containing one or more clostridial toxin. One skilled in the art understands that a variety of control substrates are useful in the methods of the invention and that a control substrate can be a positive control substrate or a negative control substrate. A control substrate can be, for example, a negative control such as a similar or identical substrate that is contacted with a similar sample that does not contain active clostridial toxin, or that is not contacted with any sample. A control substrate also can be, for example, a positive control such as the two purified cleavage products that result from clostridial toxin proteolysis of the clostridial toxin substrate.

A control substrate can be the donor fluorophore-containing cleavage product, the acceptor-containing cleavage product, or a combination of both.

The methods of the invention for determining clostridial toxin protease activity involve determining resonance energy transfer of a clostridial toxin substrate treated with a sample relative to a control substrate and can be practiced as "fixed-time" assays or as continuous time assays. Thus, in one embodiment, the FRET determination is repeated at one or more later time intervals. Fluorescence resonance energy transfer can be determined, for example, at two or more, five or more, ten or more, or twenty or more different intervals. Fluorescence intensities and other indicators of FRET also can be detected continuously by well known methods (see, for example, Wang et al., supra, 1993; Holskin et al., supra, 1995; and Kakiuchi et al., supra, 1999).

In a method of the invention, fluorescence of a treated substrate is determined using a fluorimeter. In general, excitation radiation from an excitation source having a first wavelength passes through excitation optics. The excitation optics cause the excitation radiation to excite the substrate. In response, fluorophores in the substrate emit radiation which has a wavelength that is different from the excitation wavelength. Collection optics then collect the emission; if desired, the device includes a temperature controller to maintain the clostridial toxin substrate at a specific temperature while being scanned. If desired, a multi-axis translation stage moves a microtiter plate containing a plurality of samples in order to position different wells to be exposed. It is understood that the multi-axis translation stage, temperature controller, auto-focusing feature, and electronics associated with imaging and data collection can be managed by the appropriate digital computer.

Thus, the methods of the invention can be automated and, furthermore, can be configured in a high-throughput or ultra high-throughput format using, for example, 96-well, 384-well or 1536-well plates. As one example, fluorescence emission can be detected using Molecular Devices FLIPR® instrumentation system (Molecular Devices; Sunnyvale, Calif.), which is designed for 96-well plate assays (Schroeder et al., *J. Biomol. Screening* 1:75-80 (1996)). FLIPR utilizes a water-cooled 488 nm argon ion laser (5 watt) or a xenon arc lamp and a semiconfocal optimal system with a charge-coupled device (CCD) camera to illuminate and image the entire plate. The FPM-2 96-well plate reader (Folley Consulting and Research; Round Lake, Ill.) also can be useful in detecting fluorescence emission in the methods of the invention. One skilled in the art understands that these and other automated systems with the appropriate spectroscopic compatibility such as the ECLIPSE cuvette reader (Varian-Cary; Walnut Creek, Calif.), the SPECTRA$_{max}$ GEMINI XS (Molecular Devices) and other systems from, for example, from Perkin Elmer can be useful in the methods of the invention.

The following examples are intended to illustrate but not limit the present invention.

EXAMPLE I

Analysis of BoNT/A Activity Using Fluorescence Resonance Energy Transfer

This example describes the use of a FRET assay to analyze proteolytic activity of a botulinum toxin.

The FRET substrate X1-Asp-Ser-Asn-Lys-Thr-Arg-Ile-Asp-Glu-Ala-Asn-Gln-Arg-Ala-Thr-Lys-Met-Leu-Z2-NH$_2$ (SEQ ID NO: 85) was synthesized by Alpha Diagnostics International (San Antonio, Tex.). This substrate contains a recognition sequence for BoNT/A flanked by a fluorescein-modified lysine residue ("X1") and a tetramethylrhodamine-modified lysine residue ("Z2") followed by a carboxy-terminal amide. Following proteolysis by botulinum toxin serotype A, the cleavage products X1-Asp-Ser-Asn-Lys-Thr-Arg-Ile-Asp-Glu-Ala-Asn-Gln (SEQ ID NO: 86) and Arg-Ala-Thr-Lys-Met-Leu-Z2-NH$_2$ (SEQ ID NO: 87) are produced.

Additional FRET substrates also are synthesized: X1-Asp-Ser-Asn-Lys-Thr-Arg-Ile-Asp-Glu-Ala-Asn-Gln-Arg-Ala-Thr-Lys-Met-Leu-Gly-Ser-Gly-Z2-NH$_2$ (SEQ ID NO: 88); X1-Ala-Asp-Ser-Asn-Lys-Thr-Arg-Ile-Asp-Glu-Ala-Asn-Gln-Arg-Ala-Thr-Lys-Met-Leu-Z2-NH$_2$ (SEQ ID NO: 89); X1-Ala-Asp-Ser-Asn-Lys-Thr-Arg-Ile-Asp-Glu-Ala-Asn-Gln-Arg-Ala-Thr-Lys-Met-Leu-Gly-Ser-Gly-Z2-NH$_2$ (SEQ ID NO: 90); X1-Thr-Arg-Ile-Asp-Glu-Ala-Asn-Gln-Arg-Ala-Thr-Lys-Met-Leu-Z2-NH$_2$ (SEQ ID NO: 91); X1-Thr-Arg-Ile-Asp-Glu-Ala-Asn-Gln-Arg-Ala-Thr-Lys-Met-Leu-Gly-Ser-Gly-Z2-NH$_2$ (SEQ ID NO: 92); X1-Met-Glu-Lys-Thr-Arg-Ile-Asp-Glu-Ala-Asn-Gln-Arg-Ala-Thr-Lys-Met-Leu-Gly-Ser-Gly-Z2-NH$_2$ (SEQ ID NO: 93), in each of which X1 is a fluorescein-modified lysine residue and Z2 is a tetramethylrhodamine-modified lysine residue; X3-Thr-Arg-Ile-Asp-Glu-Ala-Asn-Gln-Arg-Ala-Thr-Lys-Met-Leu-Z4-NH$_2$ (SEQ ID NO: 94), in which X3 is a DABCYL modified lysine residue and Z4 is a EDANS modified glutamate residue; and X3-Thr-Arg-Ile-Asp-Glu-Ala-Asn-Gln-Arg-Ala-Thr-Lys-Met-Leu-Gly-Ser-Gly-Z5-NH$_2$ (SEQ ID NO: 95), in which X3 is a DABCYL modified lysine residue and Z5 is a EDANS modified lysine residue.

Purified BoNT/A light chain (LC/A) or cellular extract containing LC/A is diluted in assay buffer (0.05 M HEPES (pH 7.4); 1% FBS; 10 µM ZnCl$_2$; and 10 mM DTT). Dichain BoNT/A is incubated with 10 mM dithiothreitol (DTT) for about 30 minutes prior to analysis. Reactions contain various concentrations of LC/A, dichain toxin or formulated BOTOX® product, from 0.1 ng to 10 µg. Toxin is assayed as follows: FRET substrate is added to a final concentration of 10 µM in a final volume of 100 µL assay buffer. The reaction is incubated at 37° C. for 30 minutes, and is subsequently terminated by addition of 50 µL 2M H$_2$SO$_4$.

Fluorescence is measured in a fluorimeter microplate reader (Molecular Devices SPECTRA$_{max}$ GEMINI XS) with $\lambda_{ex}$=488 nM, $\lambda_{Em}$=520 nM and $\lambda_{em}$=585 nm. A reduction of at least about 5% in the $\lambda_{em}$=585 nm is indicative of BoNT/A protease activity. An increase of about 5% in the $\lambda_{em}$=520 nm also is indicative of BoNT/A protease activity of the dichain or light chain botulinum toxin.

Kinetic assays are performed as follows. Several reactions containing the same amount of LC/A or dichain toxin are initiated in the buffer and under the conditions described above. Different reactions are then stopped at two or five minute intervals, and fluorescence detected as described above.

These results demonstrate that botulinum toxin proteolytic activity can be assayed with an intramolecularly quenched FRET substrate.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A botulinum toxin substrate, comprising
   (a) a donor fluorophore;
   (b) an acceptor having an absorbance spectrum overlapping the emission spectrum of said donor fluorophore; and
   (c) BoNT/A recognition sequence comprising a BoNT/A $P_5$-$P_4$-$P_3$-$P_2$-$P_1$-$P_1'$-$P_2'$-$P_3'$-$P_4'$-$P_5'$ cleavage site sequence, said BoNT/A $P_5$-$P_4$-$P_3$-$P_2$-$P_1$-$P_1'$-$P_2'$-$P_3'$-$P_4'$-$P_5'$ cleavage site sequence intervening between said donor fluorophore and said acceptor;
   wherein either of said donor fluorophore, said acceptor, or both said donor fluorophore and said acceptor are genetically encoded; and
   wherein, under the appropriate conditions, resonance energy transfer is exhibited between said donor fluorophore and said acceptor.

2. The substrate of claim 1, wherein said donor fluorophore is genetically encoded.

3. The substrate of claim 1, wherein said acceptor is genetically encoded.

4. The substrate of claim 1, wherein said donor fluorophore and said acceptor are genetically encoded.

5. The substrate of either claim 2 or 4, wherein said donor fluorophore is selected from the group consisting of blue fluorescent protein, cyan fluorescent protein, green fluorescent protein, yellow fluorescent protein and red fluorescent protein.

6. The substrate of either claim 3 or 4, wherein said acceptor is a fluorophore.

7. The substrate of claim 6, wherein said acceptor fluorophore is selected from the group consisting of blue fluorescent protein, cyan fluorescent protein, green fluorescent protein, yellow fluorescent protein and red fluorescent protein.

8. The substrate of either claim 3 or 4, wherein said acceptor is a non fluorescent acceptor.

9. The substrate of claim 8, wherein said non fluorescent acceptor is a heme protein.

10. The substrate of claim 1, wherein said BoNT/A $P_5$-$P_4$-$P_3$-$P_2$-$P_1$-$P_1'$-$P_2'$-$P_3'$-$P_4'$-$P_5'$ cleavage site sequence comprises at least six consecutive residues of a SNAP-25, said six consecutive residues comprising Gln-Arg.

11. The substrate of claim 10, wherein said BoNT/A $P_5$-$P_4$-$P_3$-$P_2$-$P_1$-$P_1'$-$P_2'$-$P_3'$-$P_4'$-$P_5'$ cleavage site sequence comprises at least six consecutive residues of SEQ ID NO: 2, said six consecutive residues comprising $Gln_{197}$-$Arg_{198}$.

12. The substrate of claim 10, wherein said BoNT/A $P_5$-$P_4$-$P_3$-$P_2$-$P_1$-$P_1'$-$P_2'$-$P_3'$-$P_4'$-$P_5'$ cleavage site sequence comprises SEQ ID NO: 1.

13. The substrate of claim 1, wherein said botulinum toxin recognition sequence comprises the amino acid sequence selected from the group consisting of SEQ ID NO: 27, SEQ ID NO: 28, SEQ ID NO: 29, SEQ ID NO: 30, SEQ ID NO: 31, SEQ ID NO: 32, amino acid residues 137 to 206 of SEQ ID NO: 2, amino acid residues 134 to 206 of SEQ ID NO: 2 and SEQ ID NO: 2.

14. The substrate of claim 1, wherein said donor fluorophore and said acceptor are separated by at most 10 residues.

15. The substrate of claim 1, wherein said donor fluorophore and said acceptor are separated by at most 20 residues.

16. The substrate of claim 1, wherein said donor fluorophore and said acceptor are separated by at most 30 residues.

17. The substrate of claim 1, wherein said donor fluorophore and said acceptor are separated by at most 40 residues.

18. The substrate of claim 1, wherein said substrate further comprises a BoNT/E recognition sequence comprising a BoNT/E $P_5$-$P_4$-$P_3$-$P_2$-$P_1$-$P_1'$-$P_2'$-$P_3'$-$P_4'$-$P_5'$ cleavage site sequence, said BoNT/E $P_5$-$P_4$-$P_3$-$P_2$-$P_1$-$P_1'$-$P_2'$-$P_3'$-$P_4'$-$P_5'$ cleavage site sequence intervening between said donor fluorophore and said acceptor.

19. The substrate of claims 18, wherein said BoNT/E $P_5$-$P_4$-$P_3$-$P_2$-$P_1$-$P_1'$-$P_2'$-$P_3'$-$P_4'$-$P_5'$ cleavage site sequence comprises at least six consecutive residues of a SNAP-25, said six consecutive residues comprising Arg-Ile.

20. The substrate of claims 19, wherein said BoNT/E $P_5$-$P_4$-$P_3$-$P_2$-$P_1$-$P_1'$-$P_2'$-$P_3'$-$P_4'$-$P_5'$ cleavage site sequence comprises at least six consecutive residues of SEQ ID NO: 2, said six consecutive residues comprising $Arg_{180}$-$Ile_{181}$.

21. The substrate of claims 19, wherein said BoNT/E $P_5$-$P_4$-$P_3$-$P_2$-$P_1$-$P_1'$-$P_2'$-$P_3'$-$P_4'$-$P_5'$ cleavage site sequence comprises SEQ ID NO: 8.

22. The substrate of claim 4, wherein said donor fluorophore is a blue fluorescent protein, said acceptor fluorophore is a green fluorescent protein and said botulinum toxin recognition sequence comprises SEQ ID NO: 29.

23. The substrate of claim 4, wherein said donor fluorophore is a blue fluorescent protein, said acceptor fluorophore is a green fluorescent protein and said botulinum toxin recognition sequence comprises amino acids 137-206 of SEQ ID NO: 2.

24. The substrate of claim 4, wherein said donor fluorophore is a blue fluorescent protein, said acceptor fluorophore is a green fluorescent protein and said botulinum toxin recognition sequence comprises amino acids 134-206 of SEQ ID NO: 2.

25. The substrate of claim 4, wherein said donor fluorophore is a blue fluorescent protein, said acceptor fluorophore is a green fluorescent protein and said botulinum toxin recognition sequence comprises SEQ ID NO: 2.

26. The substrate of claim 4, wherein said donor fluorophore is a green fluorescent protein, said acceptor fluorophore is a red fluorescent protein and said botulinum toxin recognition sequence comprises SEQ ID NO: 29.

27. The substrate of claim 4, wherein said donor fluorophore is a green fluorescent protein, said acceptor fluorophore is a red fluorescent protein and said botulinum toxin recognition sequence comprises amino acids 137-206 of SEQ ID NO: 2.

28. The substrate of claim 4, wherein said donor fluorophore is a green fluorescent protein, said acceptor fluorophore is a red fluorescent protein and said botulinum toxin recognition sequence comprises amino acids 134-206 of SEQ ID NO: 2.

29. The substrate of claim 4, wherein said donor fluorophore is a green fluorescent protein, said acceptor fluorophore is a red fluorescent protein and said botulinum toxin recognition sequence comprises SEQ ID NO: 2.

30. The substrate of claim 4, wherein said donor fluorophore is a cyan fluorescent protein, said acceptor fluorophore is a yellow fluorescent protein and said botulinum toxin recognition sequence comprises SEQ ID NO: 29.

31. The substrate of claim 4, wherein said donor fluorophore is a cyan fluorescent protein, said acceptor fluorophore is a yellow fluorescent protein and said botulinum toxin recognition sequence comprises amino acids 137-206 of SEQ ID NO: 2.

32. The substrate of claim 4, wherein said donor fluorophore is a cyan fluorescent protein, said acceptor fluorophore is a yellow fluorescent protein and said botulinum toxin recognition sequence comprises amino acids 134-206 of SEQ ID NO: 2.

33. The substrate of claim 4, wherein said donor fluorophore is a cyan fluorescent protein, said acceptor fluorophore is a yellow fluorescent protein and said botulinum toxin recognition sequence comprises SEQ ID NO: 2.

* * * * *

UNITED STATES PATENT AND TRADEMARK OFFICE
CERTIFICATE OF CORRECTION

PATENT NO. : 7,709,608 B2  Page 1 of 2
APPLICATION NO. : 11/609226
DATED : May 4, 2010
INVENTOR(S) : Lance E. Steward et al.

It is certified that error appears in the above-identified patent and that said Letters Patent is hereby corrected as shown below:

Title Page; item (56); on page 2, under "Other Publications", column 2, line 36, delete "Electrostatis" and insert -- Electrostatics --, therefor.

Title Page; item (56); on page 2, under "Other Publications", column 2, line 49, delete "Biochimical" and insert -- Biochemical --, therefor.

In column 1, line 36, delete "laringeal dysphonia" and insert -- laryngeal dystonia --, therefor.

In column 2, line 18-19, delete "BoNT A" and insert -- BoNT/A --, therefor.

In column 17, line 31, delete "5 sec$^{-}$" and insert -- 5 sec$^{-1}$ --, therefor.

In column 18, line 3, delete "methano" and insert -- methyl --, therefor.

In column 19, line 61, delete "are" and insert -- are: --, therefor.

In column 29, line 32-33, delete "BoNT A" and insert -- BoNT/A --, therefor.

In column 34, under "Table 6" line 5, delete "QSY ® 7" and insert -- QSY7 ® --, therefor.

In column 34, under "Table 6" line 7, delete "Napthalene" and insert -- Naphthalene --, therefor.

In column 37, under "Table 6" line 16, delete "dintrophneyl" and insert -- dintrophenyl --, therefor.

In column 37, under "Table 6" line 20, delete "N-acETYLIMIDAZOLE;" and insert -- N-acetylimidazole; --, therefor.

In column 37, under "Table 6" line 23, delete "thiosemicarazide" and insert -- thiosemicarbazide --, therefor.

In column 37, under "Table 6" line 24, delete "difluro" and insert -- difluoro --, therefor.

Signed and Sealed this

Tenth Day of August, 2010

David J. Kappos
*Director of the United States Patent and Trademark Office*

In column 37, under "Table 6" line 27, delete "napthlene" and insert -- napthalene --, therefor.

In column 37, under "Table 6" line 28, delete "napthlene" and insert -- napthalene --, therefor.

In column 37, under "Table 6" line 37, delete "napthoxyacetic" and insert -- naphthoxyacetic --, therefor.

In column 39, line 11, after "indacene" and insert -- ) --, therefor.

In column 39, line 15, after "indacene" and insert -- ) --, therefor.

In column 39, line 17, after "indacene" and insert -- ) --, therefor.

In column 44, line 26, delete "hemagluttinin" and insert -- hemagglutinin --, therefor.

In column 53, line 18, delete "fluorimeter" and insert -- fluorometer --, therefor.

In column 54, line 43, delete "fluorimeter" and insert -- fluorometer --, therefor.

In column 112, line 41-43, in Claim 31, delete "fluorescent protein, said acceptor fluorophore is a yellow fluorescent protein and said botulinum toxin recognition sequence comprises amino acids 137-206 of SEQ ID NO: 2." and insert the same on Col. 112, Line 40, after "cyan" as a continuation of the paragraph.